US012760004B2

(12) United States Patent
Carzaniga et al.

(10) Patent No.: US 12,760,004 B2
(45) Date of Patent: Oct. 13, 2026

(54) PYRROLIDINE DERIVATIVES AS DDRs INHIBITORS

(71) Applicant: CHIESI FARMACEUTICI S.P.A., Parma (IT)

(72) Inventors: Laura Carzaniga, Parma (IT); Fabio Rancati, Parma (IT); Andrea Rizzi, Parma (IT); Eleonora Ghidini, Parma (IT); Nicolò Iotti, Parma (IT); Roberta Mazzucato, Parma (IT); Stefano Levanto, Parma (IT); Ben Paul Whittaker, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 377 days.

(21) Appl. No.: 18/702,454

(22) PCT Filed: Oct. 17, 2022

(86) PCT No.: PCT/EP2022/078767

§ 371 (c)(1),
(2) Date: Apr. 18, 2024

(87) PCT Pub. No.: WO2023/066834

PCT Pub. Date: Apr. 27, 2023

(65) Prior Publication Data

US 2024/0425482 A1 Dec. 26, 2024

(30) Foreign Application Priority Data

Oct. 19, 2021 (EP) .................................... 21203367

(51) Int. Cl.

| | |
|---|---|
| ***C07D 401/14*** | (2006.01) |
| ***A61K 31/4545*** | (2006.01) |
| ***A61K 31/496*** | (2006.01) |
| ***A61K 31/497*** | (2006.01) |
| ***A61K 31/506*** | (2006.01) |
| ***A61K 31/5377*** | (2006.01) |
| ***C07D 413/14*** | (2006.01) |
| ***C07D 487/10*** | (2006.01) |

(52) U.S. Cl.

CPC ........ *C07D 401/14* (2013.01); *A61K 31/4545* (2013.01); *A61K 31/496* (2013.01); *A61K 31/497* (2013.01); *A61K 31/506* (2013.01); *A61K 31/5377* (2013.01); *C07D 413/14* (2013.01); *C07D 487/10* (2013.01)

(58) Field of Classification Search

None

See application file for complete search history.

(56) References Cited

FOREIGN PATENT DOCUMENTS

| | | | |
|---|---|---|---|
| RU | 2708395 | C2 | 7/2017 |
| WO | WO-2021043245 | A1 | 3/2021 |

OTHER PUBLICATIONS

Ahmed Elkamhawy et al, "The Journey of DDR1 and DDR2 Kinase Inhibitors as Rising Stars in the Fight against Cancer", International Journal of Molecular Sciences, XP55867412A, 22, 6535, 2021, pp. 1-27.
Atsushi Yoshimori et al, "Design and Synthesis of DDR1 Inhibitors with a Desired Pharmacophore Using Deep Generative Models", ChemMedChem, 16, XP55867413A, 2021, pp. 955-958.
Daniel E. Jeffries, "Discovery of VU6015929: A Selective Discoidin Domain Receptor 1/2 (DDR1/2) Inhibitor to Explore the Role of DDR1 in Antifibrotic Therapy", ACS Medicinal Chemistry Letters, Nov. 2020, XP55779178A, pp. 29-33.
Extended European Search Report issued Feb. 22, 2022 in Patent Application No. 21203367.4, 10 pages.
International Search Report and Written Opinion issued Feb. 9, 2023 in PCT/EP2022/078767, 15 pages.
Jing Guo et al, "A patent review of discoidin domain receptor 1 (DDR1) modulators (2014-present)", Expert Opinion on Therapeutic Patents, XP55827937A, vol. 30, No. 5, 2020, pp. 341-350.
Mingshan Gao et al, "Discovery and Optimization of 3-(2-(Pyrazolo[1,5-alpyrimidin-6-yl)-ethynyl)benzamides as Novel Selective and Orally Bioavailable Discoidin Domain Receptor 1 (DDR1) Inhibitors", Journal of Medicinal Chemistry, 56, XP55542037A. 2013. pp. 3281-3295.
Zhen Wang et al, "Design, Synthesis, and Biological Evaluation of 3-(Imidazo[1,2-a]pyrazin-3-ylethynyl)-4-isopropyl-N-[3-((4-methylpiperazin-1-yl)methyl)-5-(trifluoromethyl)phenyl)benzami de as a Dual Inhibitor of Discoidin Domain Receptors 1 and 2", Journal of Medicinal Chemistry, XP93002828A, 61, 2018, pp. 7977-7990.
Zhen Wang et al, "Tetrahydroisoquinoline-7-carboxamide Derivatives as New Selective Discoidin Domain Receptor 1 (DDR1) Inhibitors", ACS Medicinal Chemistry Letters, 8, XP55553533A, 2017, pp. 327-332.

(Continued)

*Primary Examiner* — Samantha L Shterengarts
(74) *Attorney, Agent, or Firm* — Element IP, PLC

(57) ABSTRACT

The present invention relates to compounds of formula (I) inhibiting Discoidin Domain Receptors (DDR inhibitors), methods of preparing such compounds, intermediate compounds useful in such preparations, pharmaceutical compositions containing them and therapeutic use thereof. The compounds of the invention may be useful for instance in the treatment of many disorders associated with DDR mechanisms.

(I)

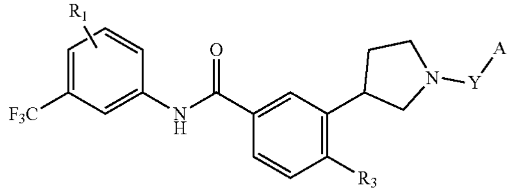

17 Claims, No Drawings

(56) References Cited

OTHER PUBLICATIONS

Elkamhawy, Ahmed, et al., “The Journey of DDRI and DDR2 Kinase Inhibitors as Rising Stars in the Fight against Cancer”, International Journal of Molecular Sciences, 2021, 22, 6535, 27 pages.

English translation of the Combined Russian Office Action and Search Report received Mar. 16, 2026, in corresponding Russian Patent Application No. 2024113309, 14 pages.

PYRROLIDINE DERIVATIVES AS DDRs INHIBITORS

FIELD OF THE INVENTION

The present invention relates to compounds inhibiting Discoidin Domain Receptors (DDR inhibitors), methods of preparing such compounds, pharmaceutical compositions containing them and therapeutic use thereof.

The compounds of the invention may be useful for instance in the treatment of many disorders associated with DDR mechanisms.

BACKGROUND OF THE INVENTION

Discoidin Domain Receptors (DDRs) are type I transmembrane receptor tyrosine kinase (RTKs). The DDR family comprises two distinct members, DDR1 and DDR2.

DDRs are unique receptors among the other members of the RTK superfamily, in that DDRs are activated by collagen whereas other members of the RTK superfamily are typically activated by soluble peptide-like growth factors (see Vogel, W. (1997) Mol. Cell 1, 13-23; Shrivastava A. Mol Cell. 1997; 1:25-34.). Moreover, DDRs are unusual RTKs also because they form ligand-independent stable dimers that are non-covalently linked (see Noordeen, N. A. (2006) J. Biol. Chem. 281, 22744-22751; Mihai C. J Mol Biol. 2009; 385:432-445).

The DDR1 subfamily is composed of five membrane-anchored isoforms, and the DDR2 subfamily is represented by a single protein. The five DDR1 isoforms all have in common the extracellular and transmembrane domains but differ in the cytoplasmic region (see Valiathan, R. R. (2012) Cancer Metastasis Rev. 31, 295-321; Alves, F. (2001) FASEB J. 15, 1321-1323).

DDR receptor family has been found involved in a series of fibrotic diseases, such as pulmonary fibrosis, and in particular idiopathic pulmonary fibrosis (IDF). The first evidence for a protective role of DDR1 deletion in lung fibrosis was generated in 2006 by the research group of Dr. Vogel (see Avivi-Green C, Am J Respir Crit Care Med 2006; 174:420-427). The authors demonstrated that DDR1-null mice were largely protected against bleomycin (BLM)-induced injury. Furthermore, myofibroblast expansion and apoptosis were much lower in these animals compared with their wild-type counterparts. Absence of inflammation in knockout mice was confirmed by lavage cell count and cytokines ELISA. These results indicated that DDR1 expression is a prerequisite for the development of lung inflammation and fibrosis.

DDR2 deficiency or downregulation reduces bleomycin-induced lung fibrosis (see Zhao H, Bian H, Bu X, Zhang S, Zhang P, Yu J, et al Mol Ther 2016; 24:1734-1744). Zhao et al, demonstrated that DDR2 plays a critical role in the induction of fibrosis and angiogenesis in the lung, in particular that DDR2 synergizes with transforming growth factor (TGF)-β to induce myofibroblast differentiation. Furthermore, they showed that treatment of injured mice with specific siRNA against DDR2 exhibited therapeutic efficacy against lung fibrosis. In a second publication, Jia et al showed that mice lacking DDR2 are protected from bleomycin-induced lung fibrosis (see Jia S, Am J Respir Cell Mol Biol 2018; 59:295-305). In addition, DDR2-null fibroblasts are significantly more prone to apoptosis than wild-type fibroblasts, supporting a paradigm in which fibroblast resistance to apoptosis is critical for progression of fibrosis.

Some compounds have been described in the literature as DDR1 or DDR2 antagonists.

Of note, antagonizing the DDR receptors may be useful for the treatment of fibrosis and diseases, disorders and conditions that result from fibrosis. Even more, antagonizing both receptors DDR1 and DDR2 may be particularly efficacious in the treatment of the above-mentioned diseases, disorders and conditions.

Several efforts have been done in the past years to develop novel DDR1 and DDR2 receptor antagonists useful for the treatment of several diseases and some of those compounds have shown efficacy also in humans. Despite the above cited prior art, there remains a potential for developing selective inhibitors of both receptors DDR1 and DDR2 useful for the treatment of diseases or conditions associated with a dysregulation of DDR receptors, in the respiratory field, in particular idiopathic pulmonary fibrosis (IPF), to be administered by the inhalation route and characterized by a good inhalatory profile, that corresponds to a good activity in the lung, a good lung retention and to a low metabolic stability in order to minimize the systemic exposure and correlated safety issues.

In this direction, we have surprisingly found a new series of compounds of general formula (I), as herein below reported, that solves the problem of providing inhibitors for receptors DDR1 and DDR2 for administration by inhalation, that are active as selective inhibitors of DDR1 and DDR2 receptors with respect to other human protein kinases. Such compounds show high potency, good inhalatory profile, low metabolic stability, low systemic exposure, improved safety and tolerability.

SUMMARY OF THE INVENTION

In a first aspect the present invention relates to a compound of formula (I)

(I)

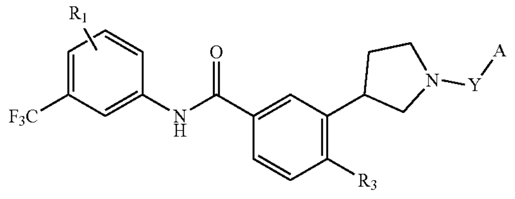

wherein

Y is absent or is —C(O)—;

$R_1$ is —$(C_1$-$C_6)$alkylene-$NR_AR_B$ or hydrogen;

$R_3$ is —$(C_1$-$C_4)$alkyl;

A is selected from the group consisting of A1, A2, A3

A1

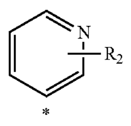

A2

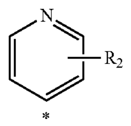

-continued

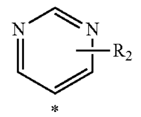

A3 and bicyclic heteroary B, wherein * indicates the point of attachment to Y and B is substituted by $R_2$; wherein $R_2$ is H or selected from the group consisting of halogen, cyano, $-NR_AR_B$, $-C(O)NR_AR_B$, $-C(O)NR_C-(C_1-C_6)$alkylene-$NR_AR_B$, $-C(O)NR_C-(C_1-C_6)$alkylene-$OR_A$, $-NR_AC(O)R_B$, $-OR_A$, $-NR_C-(C_1-C_6)$alkylene-$OR_A$, $-NR_C-(C_1-C_6)$alkylene-$NR_AR_B$, $-C(O)NR_A$-heterocycloalkyl, heterocycloalkyl, $-NR_A$-heteroaryl, $-(C_1-C_6)$alkylene-heterocycloalkyl, $-(C_1-C_6)$alkylene-$OR_A$, $-O-(C_1-C_6)$alkylene-$NR_AR_B$, $-O-(C_1-C_6)$alkylene-$OR_A$, $-O-(C_1-C_6)$alkylene-heterocycloalkyl, $-(C_1-C_6)$haloalkyl and $-(C_1-C_6)$alkyl;

$R_A$, $R_B$ and $R_C$ are independently $-(C_1-C_6)$alkyl or hydrogen;

or $R_A$ and $R_B$ taken together with the nitrogen they are attached to may form a heterocycloalkyl;

and wherein each heterocycloalkyl or heteroaryl of $R_2$ is substituted by one or more, preferably 1 to 3, substituents independently selected from the group consisting of hydrogen, halogen, $-(C_1-C_6)$alkyl, $-(C_1-C_6)$haloalkyl, $-(C_1-C_6)$alkylene-$OR_A$, $-OR_A$, $-O-(C_1-C_6)$alkylene-$NR_AR_B$ and $-O-(C_1-C_6)$alkylene-$OR_A$;

and pharmaceutically acceptable salts thereof.

In a second aspect, the invention refers to a pharmaceutical composition comprising a compound of formula (I) and pharmaceutically acceptable salts thereof in a mixture with one or more pharmaceutically acceptable carrier or excipient.

In a third aspect, the invention refers to a compound of formula (I) and pharmaceutically acceptable salts or to a pharmaceutical composition comprising a compound of formula (I) and pharmaceutically acceptable salts thereof for use as a medicament.

In a further aspect, the invention refers to a compound of formula (I) and pharmaceutically acceptable salts thereof or to a pharmaceutical composition comprising a compound of formula (I) and pharmaceutically acceptable salts thereof for use in preventing and/or treating a disease, disorder or condition associated with dysregulation of DDR.

In a further aspect, the invention refers to a compound of formula (I) and pharmaceutically acceptable salts thereof or to a pharmaceutical composition comprising a compound of formula (I) and pharmaceutically acceptable salts thereof for use in the prevention and/or treatment of fibrosis and/or diseases, disorders, or conditions that involve fibrosis.

In a further aspect, the invention refers to a compound of formula (I) and pharmaceutically acceptable salts thereof or to a pharmaceutical composition comprising a compound of formula (I) and pharmaceutically acceptable salts thereof for use in the prevention and/or treatment of idiopathic pulmonary fibrosis (IPF).

DETAILED DESCRIPTION OF THE INVENTION

Definitions

Unless otherwise specified, the compounds of formula (I) of the present invention are intended to include stereoisomers, tautomers, solvates and pharmaceutically acceptable salts thereof.

Unless otherwise specified, the compounds of formula (I) of the present invention are intended to include the compounds of formula (I)', (Ia), (Ia)', (Iaa), (Iaa)', (Iab), (Iab)', (Ib), (Ib)', (Ic), (Ic)', (Ica), (Ica)', (Id), (Id)' and (Ie).

The term “pharmaceutically acceptable salts”, as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals, such as potassium, sodium, calcium or magnesium.

The salts obtained by reacting the main compound, functioning as a base, with an inorganic or organic acid comprise, for example, salts of hydrochloric acid, hydrobromic acid, sulfuric acid, phosphoric acid, methanesulfonic acid, camphorsulfonic acid, acetic acid, oxalic acid, maleic acid, fumaric acid, succinic acid and citric acid.

The term “stereoisomer” refers to isomers of identical constitution that differ in the arrangement of their atoms in space. Enantiomers and diastereomers are examples of stereoisomers.

The term “enantiomer” refers to one of a pair of molecular species that are mirror images of each other and are not superimposable.

The term “racemate” or “racemic mixture” refers to a composition composed of equimolar quantities of two enantiomeric species, wherein the composition is devoid of optical activity.

The term “halogen” or “halogen atoms” or “halo” as used herein includes fluorine, chlorine, bromine and iodine atom.

The term “$(C_x-C_y)$alkyl”, wherein x and y are integers, refers to a straight or branched chain alkyl group having from x to y carbon atoms. Thus, when x is 1 and y is 4, for example, the term comprises methyl, ethyl, n-propyl, isopropyl, n-butyl, isobutyl, sec-butyl, and tert-butyl.

The term “$(C_x-C_y)$haloalkyl”, wherein x and y are integers, refers to a straight or branched chain alkyl group having from x to y carbon atoms, comprising at least one halogen substituent. Thus, when x is 1 and y is 6, for example, the term comprises, for instance, $CF_3$, $CHF_2$ and $C(CH_3)_2CF_3$.

The term “$(C_x-C_y)$alkylene”, wherein x and y are integers, refers to a bivalent saturated aliphatic chain derived from an alkane, having from x to y carbon atoms, by removal of two hydrogen atoms from different carbon atoms; e.g. methylenyl.

The term “heterocycloalkyl” refers to a saturated or partly unsaturated mono-, bi- or spirocyclic ring system of 3 to 12 ring atoms comprising one or more heteroatoms selected from N, S or O. An example of heterocycloalkyl is piperazinyl.

The term “spirocyclic ring system” refers to a saturated or partly unsaturated bi-cyclic ring system of 5 to 12 ring atoms, comprising one or more, for instance 1 to 3, heteroatoms selected from N, S and O, wherein the two rings have only one common carbon atom. Examples of spiro-cyclic ring systems include spiro[3.5]nonanyl, spiro[2.3]hexanyl, spiro[2.4]heptanyl, 2-azaspiro[3.3]heptanyl, 7-azaspiro[3.5]nonanyl, 2-oxa-6-azaspiro[3.3]heptanyl, 2-oxa-6-azaspiro[3.4]octanyl and 2-azaspiro[3.5]nonanyl.

The term "heteroaryl" refers to a mono- or bi-cyclic aromatic ring system, comprising a number of ring atoms from 5 to 10 and comprising from 1 to 4, or 1 to 3, or 1 to 2, heteroatoms independently selected from N, S and O, and includes groups having two such monocyclic rings, or one such monocyclic ring and one monocyclic aryl ring, such as a phenyl ring, which are fused through a common bond or linked by a single bond.

The heteroaryl ring system comprises pyrazolyl, furanyl, tiophenyl, oxazolyl, isoxazolyl, isothiazolyl, thiazolyl, imidazolyl, benzofuranyl, 1H-benzo[d]imidazolyl, 1H-indazolyl, benzothiophenyl, benzo[c]thiophenyl, quinazolinyl, pteridinyl, 1H-pyrazolo[5,1-c][1,2,4]triazolyl, pyrrolizinyl, indolizinyl, benzothiazolyl, pyrazolo[5,1-b]thiazolyl, 1H-imidazo[1,2-b]pyrazolyl, 1H-pyrazolo[3,4-b]pyridinyl, 1,6-dihydropyrrolo[2,3-b]pyrrolyl, 1,4-dihydropyrrolo[3,2-b]pyrrolyl, 4H-thieno[3,2-b]pyrrolyl, isobenzofuranyl, 1,2,4-triazolyl, 1,2,5 oxadiazolyl, 1,2,3 oxadiazolyl, 1,2,5 thiadiazolyl, 1,2,3 thiadiazolyl, tetrazolyl, 6H-furo[2,3-b]pyrrolyl, 6H-thieno[2,3-b]pyrrolyl, 4H-furo[3,2-b]pyrrolyl, benzo[d]isothiazolyl, thiazolo[4,5-b]pyridinyl, 1,3,5-triazinyl, 1,2,3,4-thiatriazolyl, 1,2,3,4-oxatriazolyl, 1,2,3,4-tetrazinyl, 1,2,4,5-tetrazinyl, 1,2,3,5-tetrazinyl, 1H-imidazo[4,5-b]pyridinyl, 7H-purinyl, 1H-pyrrolyl, 1-methyl-1H-pyrrolyl, 1-methyl-1H-1,2,4-triazolyl, 1-methyl-1H-tetrazolyl, pyridinyl, pyrimidinyl, pyrazinyl, pyridazinyl, imidazo[1,2-b]pyridazinyl, pyrazolo[1,5-a]pyrazinyl, imidazo[1,2-a]pyrazinyl, imidazo[1,2-a]pyrazinyl, imidazo[1,2-a]pyridinyl, pyrazolo[1,5-a]pyridinyl, pyrazolo[1,5-a]pyrimidinyl and 1H-pyrrolo[2,3-b]pyridinyl.

When referring to substituents, a dash ("-") that is not between two letters, words, or symbols is meant to represent the point of attachment for such substituents.

Any composite term, like for instance "—NH—($C_1$-$C_6$) alkylene-$OR_A$", should be intended as conventionally construed by the groups from which it derives; in this example by a $OR_A$ group, a ($C_1$-$C_6$)alkylene and a —NH— group, which are linked together in the indicated sequence, and wherein the group in the sequence bearing a final dash "-", the —NH— in this example, is the point of attachment to the residual part of the compound of formula (I).

The carbonyl group is herein preferably represented as —C(O)— as an alternative to the other common representations such as —CO—, —(CO)— or —C(=O)—.

Whenever basic amino groups are present in the compounds of formula (I), physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups, corresponding physiological cations may be present as well, for instance including alkaline or alkaline earth metal ions.

The term "Ki" indicates the dissociation constant for the enzyme-inhibitor complex, expressed in molar units. It is an indicator of the binding affinity between inhibitor and DDR1 or DDR2 receptors.

As above indicated, the present invention refers to a series of compounds represented by the general formula (I) as herein below described in details, which are endowed with an inhhibitory activity on receptors DDR1 and DDR2. Antagonizing receptors DDR1 and DDR2 can be particularly effective in the treatment of those diseases where the DDR receptors play a role, such as fibrosis and any other disease, disorder and condition related to fibrosis.

Indeed, as detailed in the experimental part below, the compounds of formula (I) of the present invention are able to act as inhibitors of both DDR1 and DDR2 receptors in a substantive and effective way. In particular, Table 5 below shows that for the compounds of the present invention, the inhibitory activity against either DDR1 and DDR2 receptors is lower than 60 nM in the binding (expressed as Ki). This confirms that the compounds of formula (I) are able to inhibit the two isoforms of DDR receptor mainly involved in fibrosis and diseases resulting from fibrosis. Accordingly, the compounds of formula (I) can be used in the treatment of fibrosis, in particular pulmonary fibrosis, when DDR1 and DDR2 are involved.

As indicated in the experimental part, comparative compounds section, in particular in Table 6, conversely to comparative Compound C1, characterized by having an aziridinyl in place of a pyrrolidinyl ring, the presence of a pyrrolidinyl ring in the compounds of the present invention unexpectedly and remarkably determines a relevant increase in the inhibitory activity on the DDR1 and DDR2 receptors.

Furthermore, as indicated in the same experimental part section, the reported data demonstrate that, conversely to comparative Compound C2, characterized by a —$CH_2$— linker between the pyrrolidinyl ring and group A, the absence of such linker in the compounds of the present invention unexpectedly and noteworthy determines a relevant increase in the inhibitory activity on the DDR1 and DDR2 receptors.

Advantageously, the compounds of the present invention are endowed by a very high potency and could be administered in human at a lower dosage respect to the compounds of the prior art, thus reducing the adverse events that typically occur administering higher dosages of drug.

In addition to being notably potent with respect to their inhibitory activity on both receptors DDR1 and DDR2, the compounds of the present invention are also characterized by being selective inhibitors of DDR1 and DDR2 receptors with respect to other human protein kinases, by a good inhalatory profile, that permits to act effectively on the lung compartment and have, at the same time, a low metabolic stability, that allows to minimize the drawbacks associated with the systemic exposure, such as safety and tolerability issues.

Therefore, the compounds of the present invention may be particularly appreciated when looking at suitable and efficacious compounds useful for the treatment of fibrosis, in particular idiopathic pulmonary fibrosis, administered by the inhalation route and characterized by a good inhalatory profile, that corresponds to a good activity on the lung, a good lung retention and a low metabolic stability, that minimizes the systemic exposure and correlated safety issues.

Thus, in one aspect the present invention relates to a compound of general formula (I)

(I)

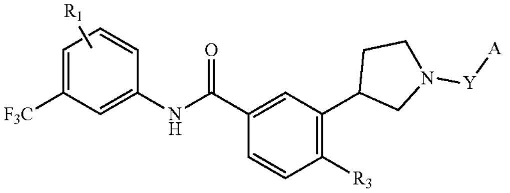

wherein

Y is absent or is —C(O)—;

$R_1$ is —($C_1$-$C_6$)alkylene-$NR_AR_B$ or hydrogen;

$R_3$ is —($C_1$-$C_4$)alkyl, preferably methyl;

A is selected from the group consisting of A1, A2, A3

A1

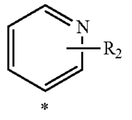

A2

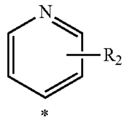

A3

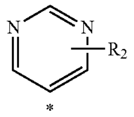

and bicyclic heteroaryl B, wherein * indicates the point of attachment to Y and B is substituted by $R_2$; wherein $R_2$ is H or selected from the group consisting of halogen, cyano, —$NR_AR_B$, —C(O)$NR_AR_B$, —C(O)$NR_C$—($C_1$-$C_6$)alkylene-$NR_AR_B$, —C(O)$NR_C$—($C_1$-$C_6$)alkylene-$OR_A$, —$NR_A$C(O)$R_B$, —$OR_A$, —$NR_C$—($C_1$-$C_6$)alkylene-$OR_A$, —$NR_C$—($C_1$-$C_6$)alkylene-$NR_AR_B$, —C(O)$NR_A$-heterocycloalkyl, heterocycloalkyl, —$NR_A$-heteroaryl, —($C_1$-$C_6$)alkylene-heterocycloalkyl, —($C_1$-$C_6$)alkylene-$OR_A$, —O—($C_1$-$C_6$)alkylene-$NR_AR_B$, —O—($C_1$-$C_6$)alkylene-$OR_A$, —O—($C_1$-$C_6$)alkylene-heterocycloalkyl, —($C_1$-$C_6$)haloalkyl and —($C_1$-$C_6$)alkyl;

$R_A$, $R_B$ and $R_C$ are independently —($C_1$-$C_6$)alkyl or hydrogen;

or $R_A$ and $R_B$ taken together with the nitrogen they are attached to may form a heterocycloalkyl;

and wherein each heterocycloalkyl or heteroaryl of $R_2$ is substituted by one or more, preferably 1 to 3, substituents independently selected from the group consisting of hydrogen, halogen, —($C_1$-$C_6$)alkyl, —($C_1$-$C_6$)haloalkyl, —($C_1$-$C_6$)alkylene-$OR_A$, —$OR_A$, —O—($C_1$-$C_6$)alkylene-$NR_AR_B$ and —O—($C_1$-$C_6$)alkylene-$OR_A$;

and pharmaceutically acceptable salts thereof.

All the listed meanings of each of the variable moieties Y, A, $R_1$, $R_2$, $R_3$, $R_A$, $R_B$ and $R_C$ of the compound of formula (I) of the invention have to be intended as alternatives and may be combined with each other in embodiments which are included in the scope of the invention.

Preferred halogens, as such and in —($C_1$-$C_6$)haloalkyl substituents, are fluorine and bromine, wherein fluorine is more preferred.

In preferred embodiments of the invention, —($C_1$-$C_6$) alkylene- chains are —($C_1$-$C_3$)alkylene- chains.

In preferred embodiments of the invention, —($C_1$-$C_6$) alkyl substituents are —($C_1$-$C_4$)alkyl substituents.

$R_1$ and $R_2$ are single substituents of the $CF_3$-substituted phenyl and of A, respectively, wherein $R_1$ and $R_2$ can be attached to any available position. Preferred positions for substituent $R_1$ is para- or meta- to the —NH—C(O)— substituent. Preferred positions for substituent $R_2$ are outlined in the embodiments of the invention as described further below.

In a preferred embodiment, the present invention relates to a compound of general formula (I) wherein $R_1$ is hydrogen and $R_3$ is methyl, represented by formula (I)'

(I)'

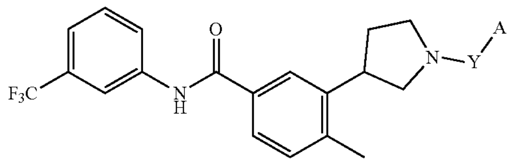

wherein

Y is absent or is —C(O)—;

A is selected from the group consisting of A1, A2 and A3

A1

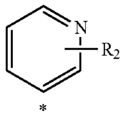

A2

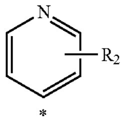

A3

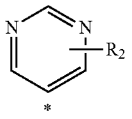

wherein * indicates the point of attachment to Y; and wherein $R_2$ is H or selected from the group consisting of halogen atoms, cyano, —C(O)$NH_2$, —C(O)NH—($C_1$-$C_6$)alkyl, —C(O)NH—($C_1$-$C_6$)alkylene-$NR_AR_B$, —C(O)NH—($C_1$-$C_6$)alkylene-$OR_A$, —NHC(O)$R_B$, —O—($C_1$-$C_6$) alkyl, —NH—($C_1$-$C_6$)alkylene-$OR_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more —($C_1$-$C_6$) alkyl;

$R_A$ is —($C_1$-$C_6$)alkyl;

$R_B$ is —($C_1$-$C_6$)alkyl;

and pharmaceutically acceptable salts thereof.

In a preferred embodiment, the present invention relates to a compound of formula (I) wherein Y is absent.

In another preferred embodiment, the present invention relates to a compound of formula (I) wherein Y is absent and A is A1

A1

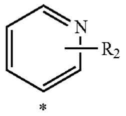

represented by formula (Ia)

(Ia)

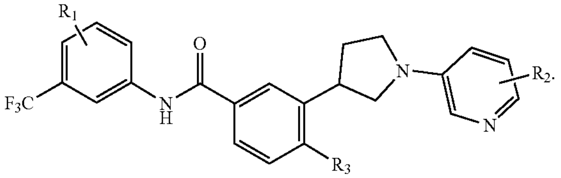

In a more preferred embodiment, the present invention relates to a compound of formula (Ia) wherein $R_1$ is hydrogen and $R_3$ is methyl, represented by formula (Ia)'

(Ia)'

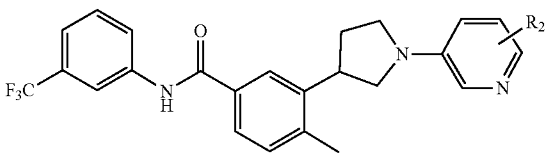

wherein $R_2$ is H or selected from the group consisting of halogen atoms, cyano, —C(O)NH$_2$, —C(O)NH—($C_1$-$C_6$)alkyl, —C(O)NH—($C_1$-$C_6$)alkylene-NR$_A$R$_B$, —C(O)NH—($C_1$-$C_6$)alkylene-OR$_A$, —NHC(O)R$_B$—, —O—($C_1$-$C_6$)alkyl, —NH—($C_1$-$C_6$)alkylene-OR$_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more ($C_1$-$C_6$) alkyl;

$R_A$ is —($C_1$-$C_6$)alkyl;

$R_B$ is —($C_1$-$C_6$)alkyl;

and pharmaceutically acceptable salts thereof.

In another preferred embodiment, the present invention relates to a compound of general formula (I) wherein Y is absent and A is Ala Ala

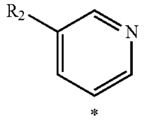

represented by formula (Iaa)

(Iaa)

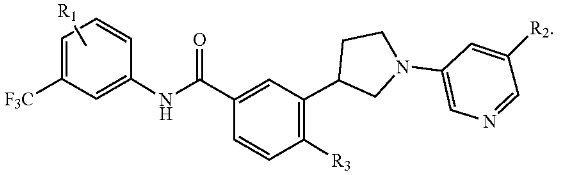

In a more preferred embodiment, the present invention relates to a compound of formula (Iaa) wherein $R_1$ is hydrogen and $R_3$ is methyl, represented by formula (Iaa)'

(Iaa)'

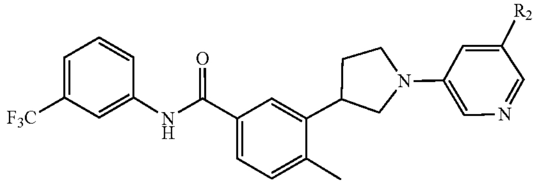

wherein $R_2$ is H or selected from the group consisting of halogen atoms, cyano, —C(O)NH$_2$, —C(O)NH—($C_1$-$C_6$)alkyl, —C(O)NH—($C_1$-$C_6$)alkylene-NR$_A$R$_B$, —C(O)NH—($C_1$-$C_6$)alkylene-OR$_A$, —NHC(O)R$_B$, —O—($C_1$-$C_6$) alkyl, —NH—($C_1$-$C_6$)alkylene-OR$_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more ($C_1$-$C_6$) alkyl;

$R_A$ is —($C_1$-$C_6$)alkyl;

$R_B$ is —($C_1$-$C_6$)alkyl;

and pharmaceutically acceptable salts thereof.

In a further preferred embodiment, the present invention refers to a compound of formula (Iaa) or (Iaa)', wherein $R_2$ is H or is selected from the group consisting of methoxy, cyano, bromo, 2-morpholinoethoxy, (4-methylpiperazin-1-yl)ethoxy, morpholinyl, 2-(dimethylamino)ethylcarbamoyl, N-methylcarbamoyl, carbamoyl, morpholinomethyl and 4-methylpiperazin-1-yl. Other preferred embodiments of the present invention are compounds of formula (Iaa) wherein $R_2$ is H or is selected from the group consisting of 2-(dimethylamino)ethoxy, 2-methoxyethylcarbamoyl, acetamido and 1-methyl-1H-3-pyrazolyl.

Most preferably, the invention refers to at least one of the compounds of Formula (Iaa) listed in Table 1 below and pharmaceutically acceptable salts thereof. These compounds are particularly active on receptors DDR1 and DDR2, as shown in Table 5.

TABLE 1

List of compounds of Formula (Iaa)

| Example No. | Structure | Chemical Name |
| --- | --- | --- |
| 2 | 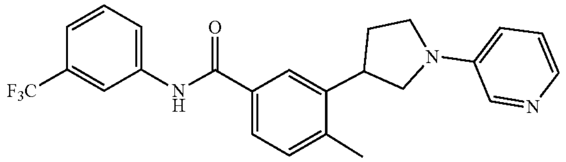 [SMILES: Cc1ccc(C(=O)Nc2cccc(C(F)(F)F)c2)cc1C1CCN(c2cccnc2)C1] | 4-methyl-3-(1-(pyridin-3-yl)pyrrolidin-3-yl)-N-(3-(trifluoromethyl)phenyl)benzamide |

TABLE 1-continued

| List of compounds of Formula (Iaa) | | |
|---|---|---|
| Example No. | Structure | Chemical Name |
| 3 | 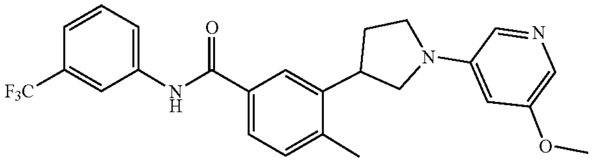 [SMILES: COc1cncc(N2CCC(c3cc(C(=O)Nc4cccc(C(F)(F)F)c4)ccc3C)C2)c1] | 3-(1-(5-methoxypyridin-3-yl)pyrrolidin-3-yl)-4-methyl-N-(3-(trifluoromethyl)phenyl)benzamide |
| 4 | 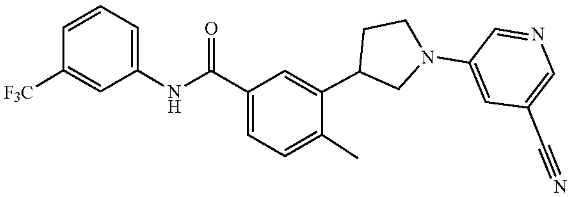 [SMILES: Cc1ccc(C(=O)Nc2cccc(C(F)(F)F)c2)cc1C1CCN(c2cncc(C#N)c2)C1] | 3-(1-(5-cyanopyridin-3-yl)pyrrolidin-3-yl)-4-methyl-N-(3-(trifluoromethyl)phenyl)benzamide |
| 5 | 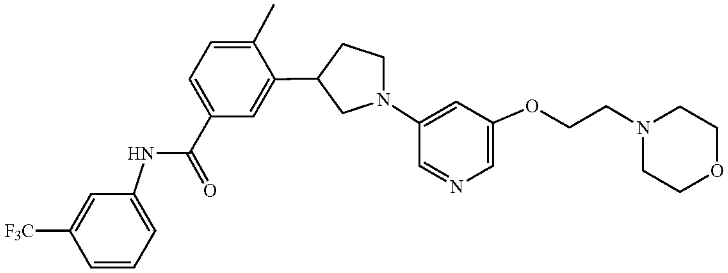 [SMILES: Cc1ccc(C(=O)Nc2cccc(C(F)(F)F)c2)cc1C1CCN(c2cncc(OCCN3CCOCC3)c2)C1] | 4-methyl-3-(1-(5-(2-morpholinoethoxy)pyridin-3-yl)pyrrolidin-3-yl)-N-(3-(trifluoromethyl)phenyl)benzamide |
| 6 | 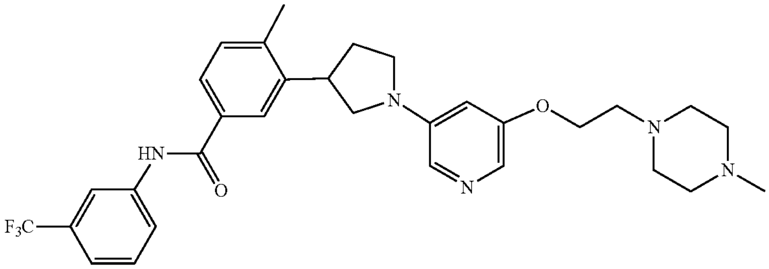 [SMILES: Cc1ccc(C(=O)Nc2cccc(C(F)(F)F)c2)cc1C1CCN(c2cncc(OCCN3CCN(C)CC3)c2)C1] | 4-methyl-3-(1-(5-(2-(4-methylpiperazin-1-yl)ethoxy)pyridin-3-yl)pyrrolidin-3-yl)-N-(3-(trifluoromethyl)phenyl)benzamide |
| 7 | 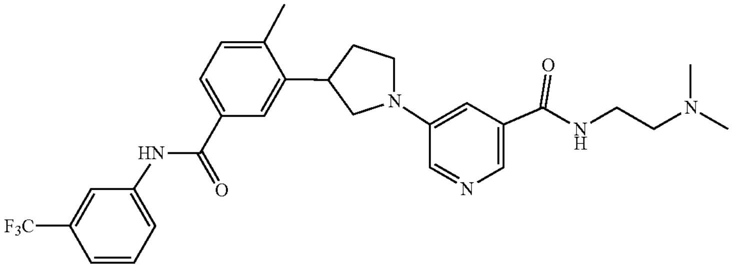 [SMILES: Cc1ccc(C(=O)Nc2cccc(C(F)(F)F)c2)cc1C1CCN(c2cncc(C(=O)NCCN(C)C)c2)C1] | N-(2-(dimethylamino)ethyl)-5-(3-(2-methyl-5-((3-(trifluoromethyl)phenyl)carbamoyl)phenyl)pyrrolidin-1-yl)nicotinamide |
| 8 | 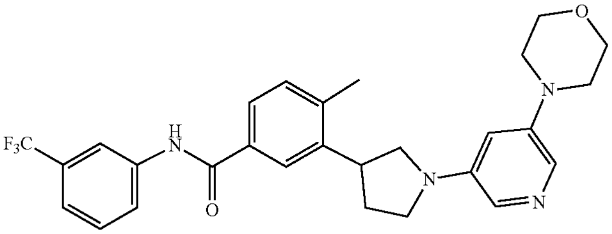 [SMILES: Cc1ccc(C(=O)Nc2cccc(C(F)(F)F)c2)cc1C1CCN(c2cncc(N3CCOCC3)c2)C1] | 4-methyl-3-(1-(5-morpholinopyridin-3-yl)pyrrolidin-3-yl)-N-(3-(trifluoromethyl)phenyl)benzamide |

TABLE 1-continued

| List of compounds of Formula (Iaa) | | |
|---|---|---|
| Example No. | Structure | Chemical Name |
| 9 | 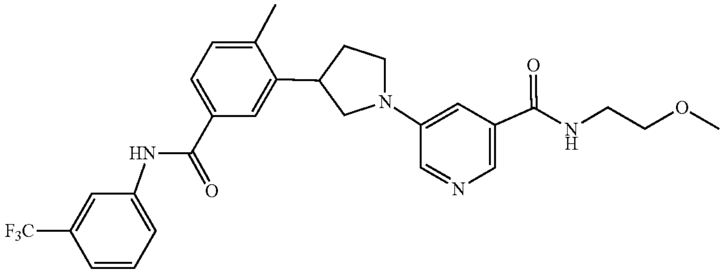 [SMILES: COCCNC(=O)c1cncc(N2CCC(c3cc(C(=O)Nc4cccc(C(F)(F)F)c4)ccc3C)C2)c1] | N-(2-methoxyethyl)-5-(3-(2-methyl-5-((3-(trifluoromethyl)phenyl)carbamoyl)phenyl)pyrrolidin-1-yl)nicotinamide |
| 10 | 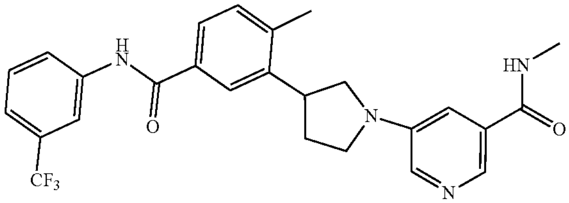 [SMILES: CNC(=O)c1cncc(N2CCC(c3cc(C(=O)Nc4cccc(C(F)(F)F)c4)ccc3C)C2)c1] | N-methyl-5-(3-(2-methyl-5-((3-(trifluoromethyl)phenyl)carbamoyl)phenyl)pyrrolidin-1-yl)nicotinamide |
| 11 | 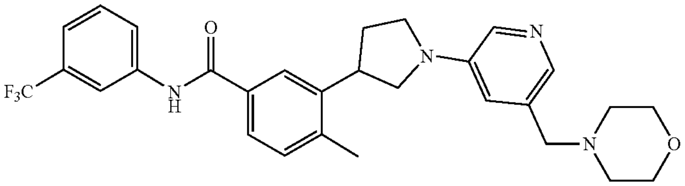 [SMILES: Cc1ccc(C(=O)Nc2cccc(C(F)(F)F)c2)cc1C1CCN(c2cncc(CN3CCOCC3)c2)C1] | 4-methyl-3-(1-(5-(morpholinomethyl)pyridin-3-yl)pyrrolidin-3-yl)-N-(3-(trifluoromethyl)phenyl)benzamide |
| 12 | 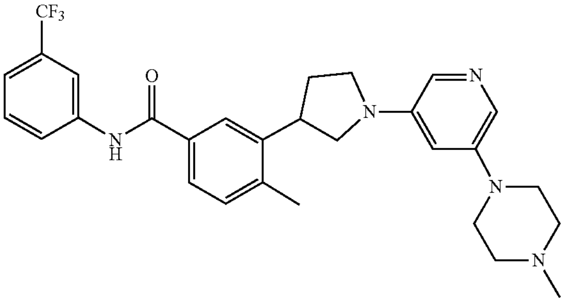 [SMILES: Cc1ccc(C(=O)Nc2cccc(C(F)(F)F)c2)cc1C1CCN(c2cncc(N3CCN(C)CC3)c2)C1] | 4-methyl-3-(1-(5-(4-methylpiperazin-1-yl)pyridin-3-yl)pyrrolidin-3-yl)-N-(3-(trifluoromethyl)phenyl)benzamide |
| 13 | 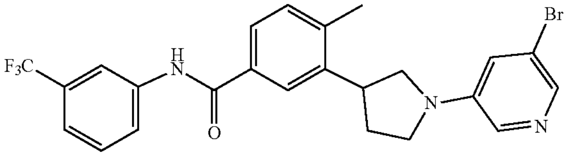 [SMILES: Cc1ccc(C(=O)Nc2cccc(C(F)(F)F)c2)cc1C1CCN(c2cncc(Br)c2)C1] | 3-(1-(5-bromopyridin-3-yl)pyrrolidin-3-yl)-4-methyl-N-(3-(trifluoromethyl)phenyl)benzamide |
| 15 | 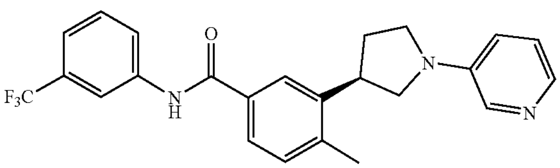 [SMILES: Cc1ccc(C(=O)Nc2cccc(C(F)(F)F)c2)cc1[C@H]1CCN(c2cccnc2)C1] | (R)-4-methyl-3-(1-(pyridin-3-yl)pyrrolidin-3-yl)-N-(3-(trifluoromethyl)phenyl)benzamide |
| 16 | 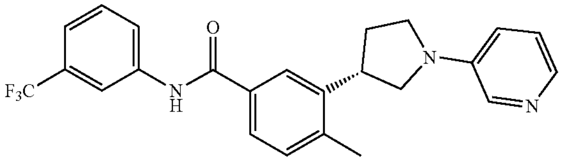 [SMILES: Cc1ccc(C(=O)Nc2cccc(C(F)(F)F)c2)cc1[C@@H]1CCN(c2cccnc2)C1] | (S)-4-methyl-3-(1-(pyridin-3-yl)pyrrolidin-3-yl)-N-(3-(trifluoromethyl)phenyl)benzamide |

TABLE 1-continued

| List of compounds of Formula (Iaa) | | |
|---|---|---|
| Example No. | Structure | Chemical Name |
| 17 | 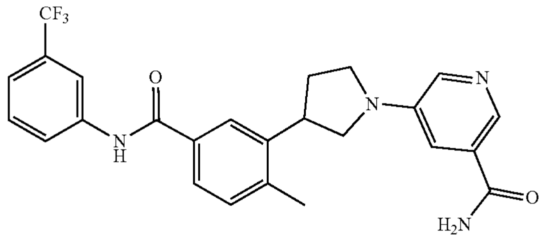 [SMILES: Cc1ccc(C(=O)Nc2cccc(C(F)(F)F)c2)cc1C1CCN(c2cncc(C(N)=O)c2)C1] | 5-(3-(2-methyl-5-((3-(trifluoromethyl)phenyl) carbamoyl)phenyl)pyrrolidin-1-yl)nicotinamide |
| 18 | 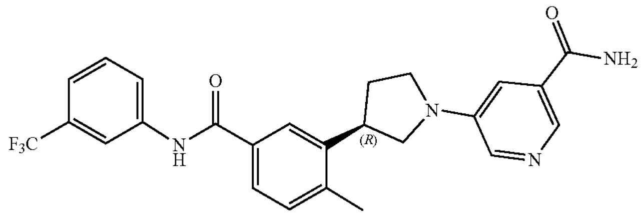 | (R)-5-(3-(2-methyl-5-((3-(trifluoromethyl) phenyl)carbamoyl)phenyl) pyrrolidin-1-yl)nicotinamide |
| 19 | 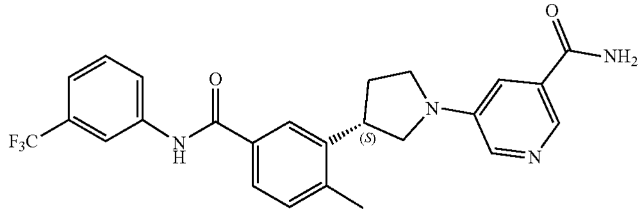 | (S)-5-(3-(2-methyl-5-((3-(trifluoromethyl) phenyl)carbamoyl)phenyl) pyrrolidin-1-yl)nicotinamide |
| 21 | 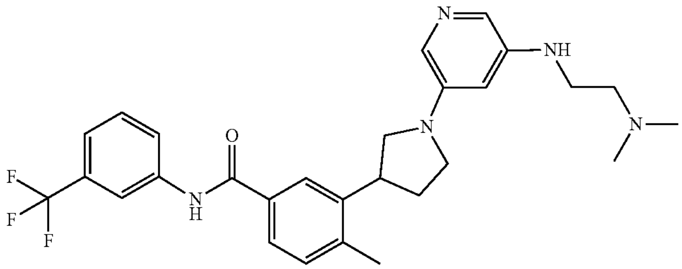 [SMILES: Cc1ccc(C(=O)Nc2cccc(C(F)(F)F)c2)cc1C1CCN(c2cncc(NCCN(C)C)c2)C1] | 3-(1-(5-((2-(dimethylamino)ethyl) amino)pyridin-3-yl)pyrrolidin-3-yl)-4-methyl-N-(3-(trifluoromethyl)phenyl) benzamide |
| 22 | 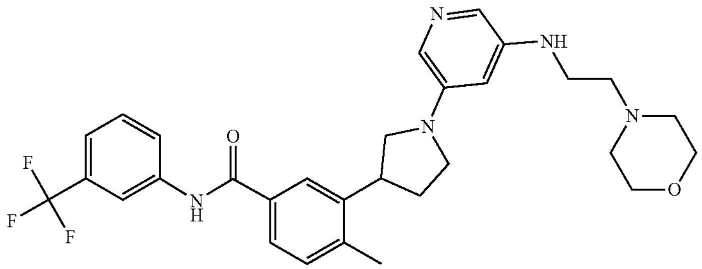 [SMILES: Cc1ccc(C(=O)Nc2cccc(C(F)(F)F)c2)cc1C1CCN(c2cncc(NCCN3CCOCC3)c2)C1] | 4-methyl-3-(1-(5-((2-morpholinoethyl)amino) pyridin-3-yl)pyrrolidin-3-yl)-N-(3-(trifluoromethyl)phenyl) benzamide |
| 23 | 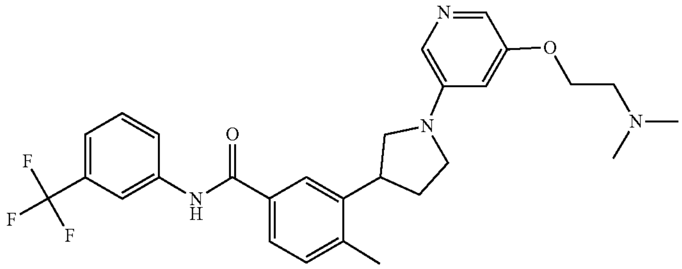 [SMILES: Cc1ccc(C(=O)Nc2cccc(C(F)(F)F)c2)cc1C1CCN(c2cncc(OCCN(C)C)c2)C1] | 3-(1-(5-(2-(dimethylamino)ethoxy) pyridin-3-yl)pyrrolidin-3-yl)-4-methyl-N-(3-(trifluoromethyl)phenyl) benzamide |

TABLE 1-continued
| List of compounds of Formula (Iaa) | | |
|---|---|---|
| Example No. | Structure | Chemical Name |
| 26 | 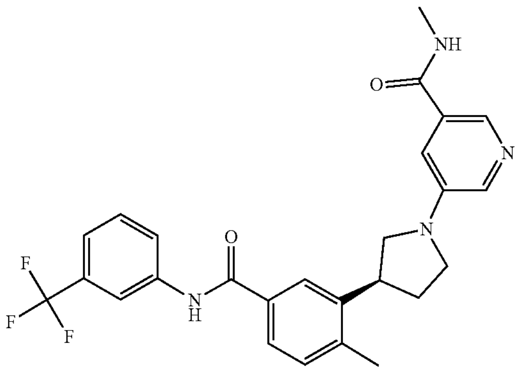 [SMILES: CNC(=O)c1cncc(N2CC[C@@H](c3cc(C(=O)Nc4cccc(C(F)(F)F)c4)ccc3C)C2)c1] | (S)-N-methyl-5-(3-(2-methyl-5-((3-(trifluoromethyl)phenyl)carbamoyl)phenyl)pyrrolidin-1-yl)nicotinamide |
| 28 | 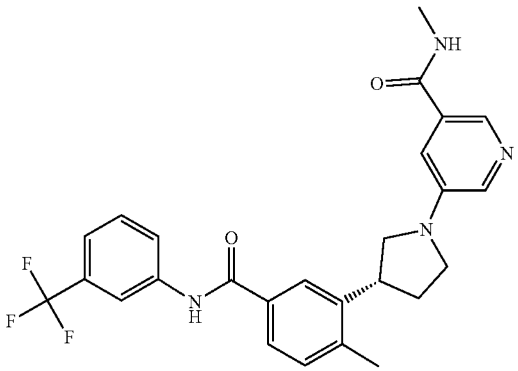 [SMILES: CNC(=O)c1cncc(N2CC[C@H](c3cc(C(=O)Nc4cccc(C(F)(F)F)c4)ccc3C)C2)c1] | (R)-N-methyl-5-(3-(2-methyl-5-((3-(trifluoromethyl)phenyl)carbamoyl)phenyl)pyrrolidin-1-yl)nicotinamide |
| 30 | 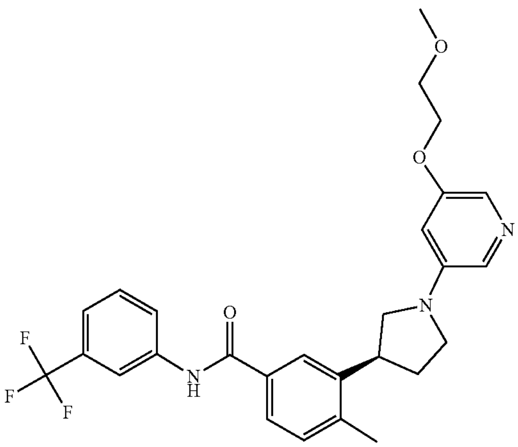 | (S)-3-(1-(5-(2-methoxyethoxy)pyridin-3-yl)pyrrolidin-3-yl)-4-methyl-N-(3-(trifluoromethyl)phenyl)benzamide |

TABLE 1-continued

| List of compounds of Formula (Iaa) | | |
|---|---|---|
| Example No. | Structure | Chemical Name |
| 31 | 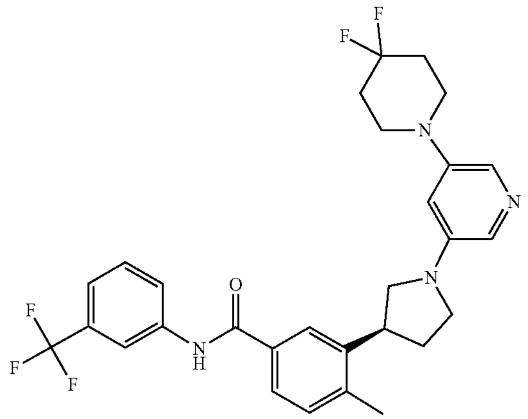 [SMILES: Cc1ccc(C(=O)Nc2cccc(C(F)(F)F)c2)cc1[C@@H]1CCN(c2cncc(N3CCC(F)(F)CC3)c2)C1] | (S)-3-(1-(5-(4,4-difluoropiperidin-1-yl)pyridin-3-yl)pyrrolidin-3-yl)-4-methyl-N-(3-(trifluoromethyl)phenyl) benzamide |
| 32 | 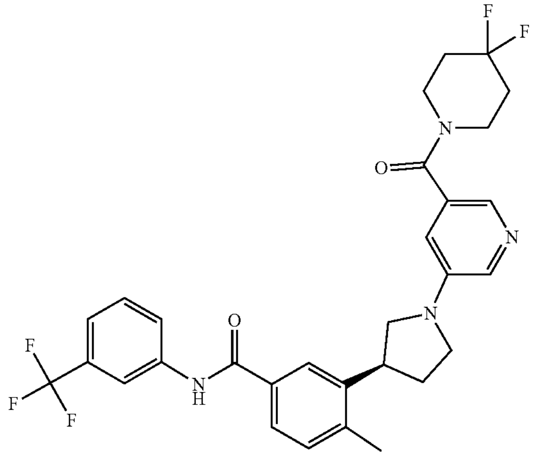 [SMILES: Cc1ccc(C(=O)Nc2cccc(C(F)(F)F)c2)cc1[C@@H]1CCN(c2cncc(C(=O)N3CCC(F)(F)CC3)c2)C1] | (S)-3-(1-(5-(4,4-difluoropiperidine-1-carbonyl)pyridin-3-yl)pyrrolidin-3-yl)-4-methyl-N-(3-(trifluoromethyl)phenyl) benzamide |
| 33 | 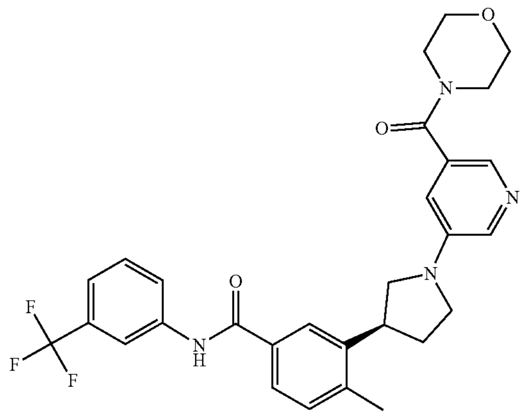 [SMILES: Cc1ccc(C(=O)Nc2cccc(C(F)(F)F)c2)cc1[C@@H]1CCN(c2cncc(C(=O)N3CCOCC3)c2)C1] | (S)-4-methyl-3-(1-(5-(morpholine-4-carbonyl)pyridin-3-yl)pyrrolidin-3-yl)-N-(3-(trifluoromethyl)phenyl) benzamide |

TABLE 1-continued

| List of compounds of Formula (Iaa) | | |
|---|---|---|
| Example No. | Structure | Chemical Name |
| 34 | 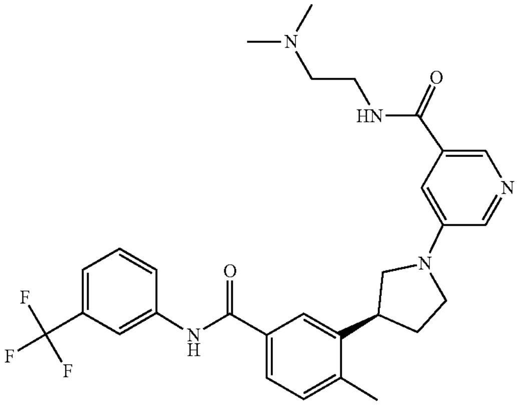 [SMILES: Cc1ccc(C(=O)Nc2cccc(C(F)(F)F)c2)cc1[C@@H]1CCN(c2cncc(C(=O)NCCN(C)C)c2)C1] | (S)-N-(2-(dimethylamino)ethyl)-5-(3-(2-methyl-5-((3-(trifluoromethyl)phenyl)carbamoyl)phenyl)pyrrolidin-1-yl)nicotinamide |
| 35 | 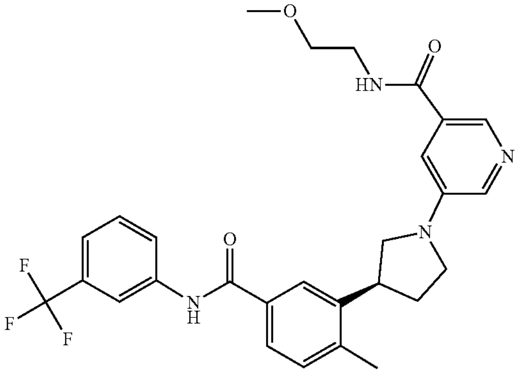 [SMILES: COCCNC(=O)c1cncc(N2CC[C@@H](c3cc(C(=O)Nc4cccc(C(F)(F)F)c4)ccc3C)C2)c1] | (S)-N-(2-methoxyethyl)-5-(3-(2-methyl-5-((3-(trifluoromethyl)phenyl)carbamoyl)phenyl)pyrrolidin-1-yl)nicotinamide |
| 36 | 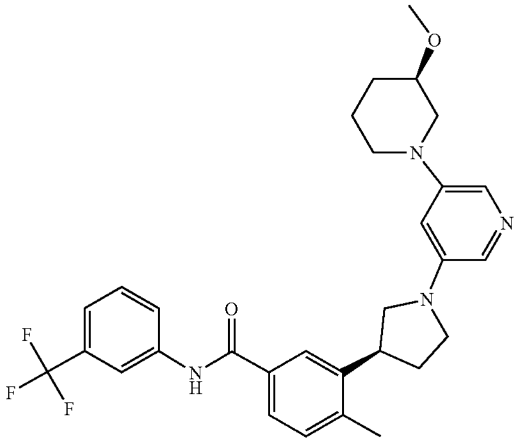 [SMILES: CO[C@@H]1CCCN(c2cncc(N3CC[C@@H](c4cc(C(=O)Nc5cccc(C(F)(F)F)c5)ccc4C)C3)c2)C1] | 3-((S)-1-(5-((R)-3-methoxypiperidin-1-yl)pyridin-3-yl)pyrrolidin-3-yl)-4-methyl-N-(3-(trifluoromethyl)phenyl)benzamide |

TABLE 1-continued

| List of compounds of Formula (Iaa) | | |
|---|---|---|
| Example No. | Structure | Chemical Name |
| 37 | 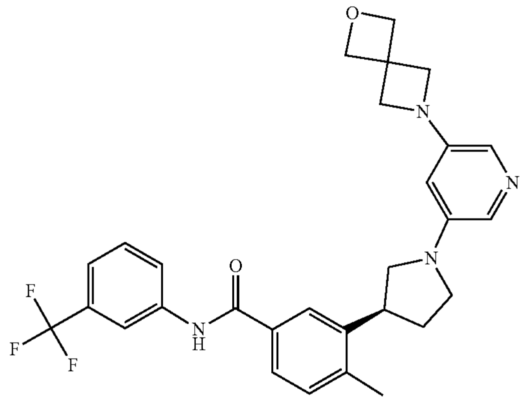 [SMILES: Cc1ccc(C(=O)Nc2cccc(C(F)(F)F)c2)cc1[C@@H]1CCN(c2cncc(N3CC4(COC4)C3)c2)C1] | (S)-3-(1-(5-(2-oxa-6-azaspiro[3.3]heptan-6-yl)pyridin-3-yl)pyrrolidin-3-yl)-4-methyl-N-(3-(trifluoromethyl)phenyl) benzamide |
| 38 | 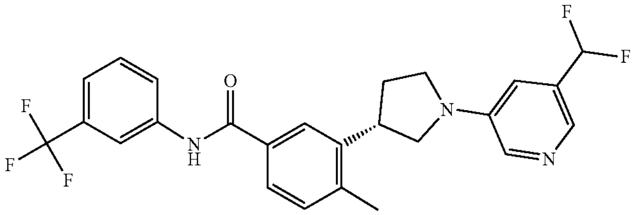 [SMILES: Cc1ccc(C(=O)Nc2cccc(C(F)(F)F)c2)cc1[C@@H]1CCN(c2cncc(C(F)F)c2)C1] | (S)-3-(1-(5-(difluoromethyl)pyridin-3-yl)pyrrolidin-3-yl)-4-methyl-N-(3-(trifluoromethyl)phenyl) benzamide |
| 39 | 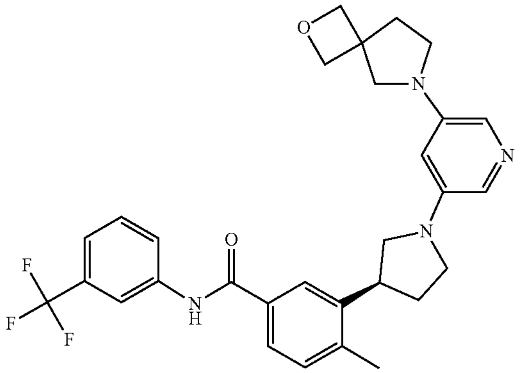 [SMILES: Cc1ccc(C(=O)Nc2cccc(C(F)(F)F)c2)cc1[C@@H]1CCN(c2cncc(N3CCC4(COC4)C3)c2)C1] | (S)-3-(1-(5-(2-oxa-6-azaspiro[3.4]octan-6-yl)pyridin-3-yl)pyrrolidin-3-yl)-4-methyl-N-(3-(trifluoromethyl)phenyl) benzamide |
| 40 | 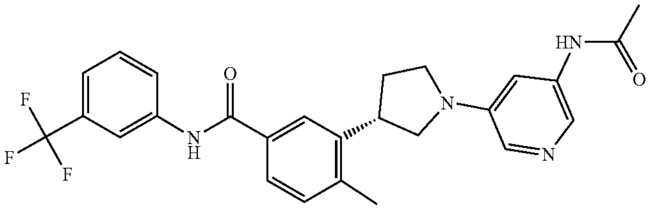 [SMILES: CC(=O)Nc1cncc(N2CC[C@@H](c3cc(C(=O)Nc4cccc(C(F)(F)F)c4)ccc3C)C2)c1] | (S)-3-(1-(5-acetamidopyridin-3-yl)pyrrolidin-3-yl)-4-methyl-N-(3-(trifluoromethyl)phenyl) benzamide |

TABLE 1-continued

| List of compounds of Formula (Iaa) | | |
|---|---|---|
| Example No. | Structure | Chemical Name |
| 45 | 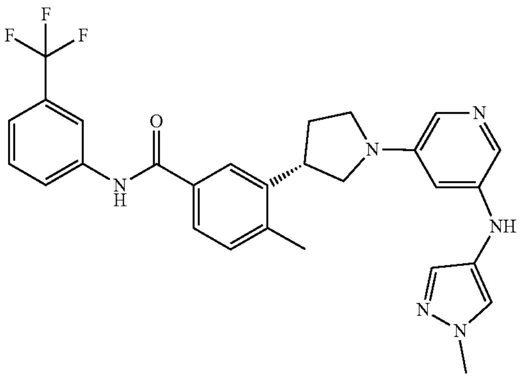 [SMILES: Cc1ccc(C(=O)Nc2cccc(C(F)(F)F)c2)cc1[C@@H]1CCN(c2cncc(Nc3cnn(C)c3)c2)C1] | (S)-4-methyl-3-(1-(5-((1-methyl-1H-pyrazol-4-yl)amino)pyridin-3-yl)pyrrolidin-3-yl)-N-(3-(trifluoromethyl)phenyl) benzamide |
| 46 | 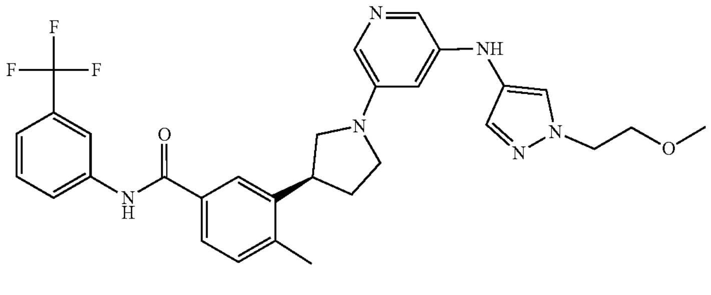 [SMILES: COCCn1cc(Nc2cncc(N3CC[C@@H](c4cc(C(=O)Nc5cccc(C(F)(F)F)c5)ccc4C)C3)c2)cn1] | (S)-3-(1-(5-((1-(2-methoxyethyl)-1H-pyrazol-4-yl)amino)pyridin-3-yl)pyrrolidin-3-yl)-4-methyl-N-(3-(trifluoromethyl)phenyl) benzamide |
| 52 | 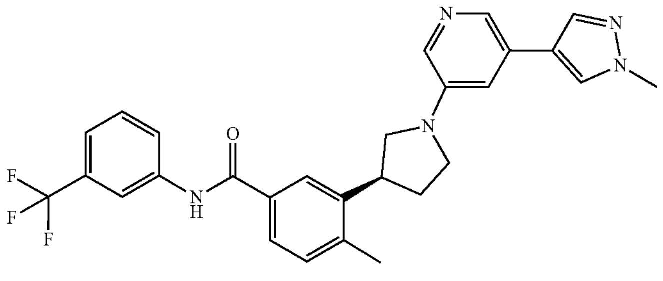 [SMILES: Cc1ccc(C(=O)Nc2cccc(C(F)(F)F)c2)cc1[C@@H]1CCN(c2cncc(-c3cnn(C)c3)c2)C1] | (S)-4-methyl-3-(1-(5-(1-methyl-1H-pyrazol-4-yl)pyridin-3-yl)pyrrolidin-3-yl)-N-(3-(trifluoromethyl)phenyl) benzamide |
| 56 | 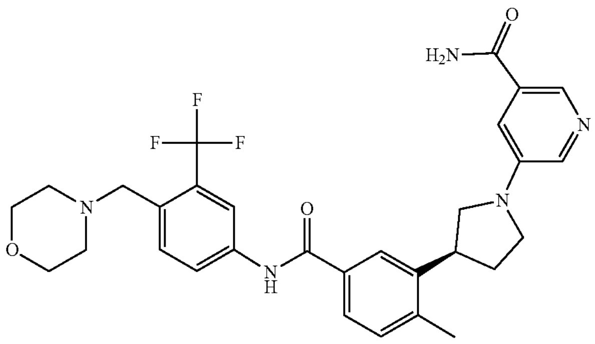 [SMILES: Cc1ccc(C(=O)Nc2ccc(CN3CCOCC3)c(C(F)(F)F)c2)cc1[C@@H]1CCN(c2cncc(C(N)=O)c2)C1] | (S)-5-(3-(2-methyl-5-((4-(morpholinomethyl)-3-(trifluoro methyl)phenyl)carbamoyl) phenyl)pyrrolidin-1-yl)nicotinamide |

TABLE 1-continued

List of compounds of Formula (Iaa)

| Example No. | Structure | Chemical Name |
| --- | --- | --- |
| 57 | 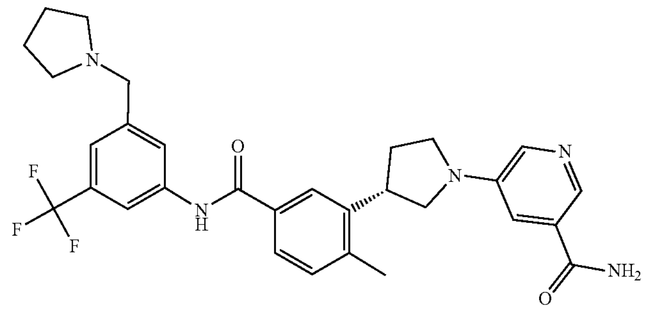 [SMILES: Cc1ccc(C(=O)Nc2cc(CN3CCCC3)cc(C(F)(F)F)c2)cc1[C@@H]1CCN(c2cncc(C(N)=O)c2)C1] | (S)-5-(3-(2-methyl-5-((3-(pyrrolidin-1-ylmethyl)-5-(trifluoromethyl)phenyl)carbamoyl)phenyl)pyrrolidin-1-yl)nicotinamide |
| 58 | 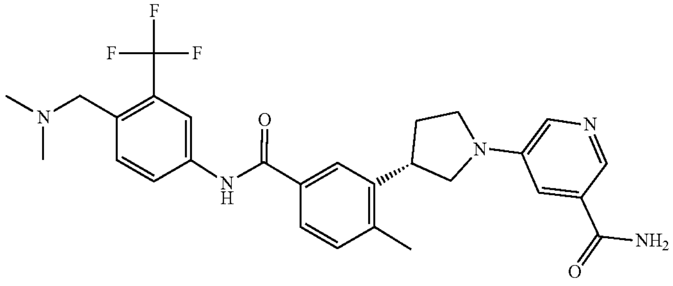 [SMILES: Cc1ccc(C(=O)Nc2ccc(CN(C)C)c(C(F)(F)F)c2)cc1[C@@H]1CCN(c2cncc(C(N)=O)c2)C1] | (S)-5-(3-(5-((4-((dimethylamino)methyl)-3-(trifluoromethyl)phenyl)carbamoyl)-2-methylphenyl)pyrrolidin-1-yl)nicotinamide |

In another preferred embodiment, the present invention relates to a compound of general formula (I) wherein Y is absent and A is Alb

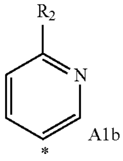

Alb represented by formula (Iab)

(Iab)

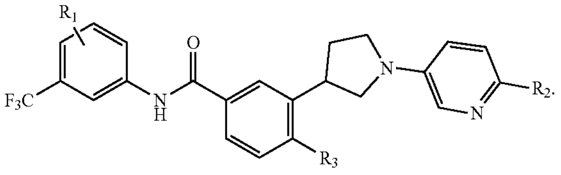

In a more preferred embodiment, the present invention relates to a compound of formula (Iab) wherein $R_1$ is hydrogen and $R_3$ is methyl, represented by formula (Iab)'

(Iab)'

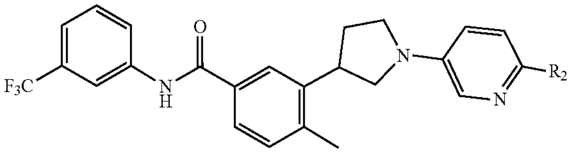

wherein $R_2$ is H or selected from the group consisting of halogen atoms, cyano, —C(O)$NH_2$, —C(O)NH—($C_1$-$C_6$)alkyl, —C(O)NH—($C_1$-$C_6$)alkylene-$NR_AR_B$, —C(O)NH—($C_1$-$C_6$)alkylene-$OR_A$, —NHC(O)$R_B$, —O—($C_1$-$C_6$) alkyl, —NH—($C_1$-$C_6$)alkylene-$OR_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more ($C_1$-$C_6$) alkyl;

$R_A$ is —($C_1$-$C_6$)alkyl;

$R_B$ is —($C_1$-$C_6$)alkyl;

and pharmaceutically acceptable salts thereof.

Most preferably, the invention refers to at least one of the compounds of Formula (Iab) listed in Table 1' below and pharmaceutically acceptable salts thereof. These compounds are particularly active on receptors DDR1 and DDR2, as shown in Table 5.

TABLE 1'

List of compounds of Formula (Iab)

| Example No. | Structure | Chemical Name |
|---|---|---|
| 44 | 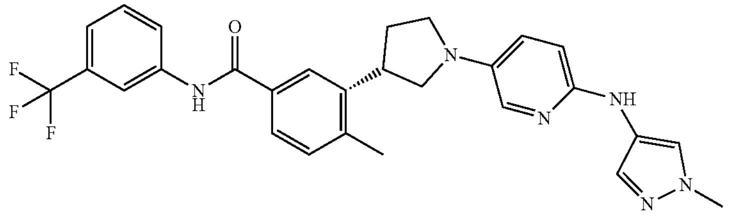 | (S)-4-methyl-3-(1-(6-((1-methyl-1H-pyrazol-4-yl)amino)pyridin-3-yl)pyrrolidin-3-yl)-N-(3-(trifluoromethyl) phenyl)benzamide |
| 47 | 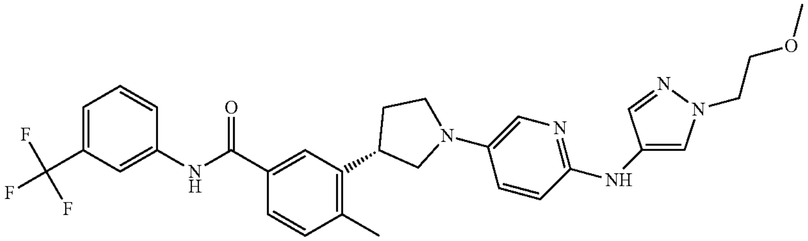 [SMILES: COCCn1cc(Nc2ccc(N3CC[C@@H](c4cc(C(=O)Nc5cccc(C(F)(F)F)c5)ccc4C)C3)cn2)cn1] | (S)-3-(1-(6-((1-(2-methoxyethyl)-1H-pyrazol-4-yl)amino)pyridin-3-yl)pyrrolidin-3-yl)-4-methyl-N-(3-(trifluoromethyl) phenyl)benzamide |
| 50 | 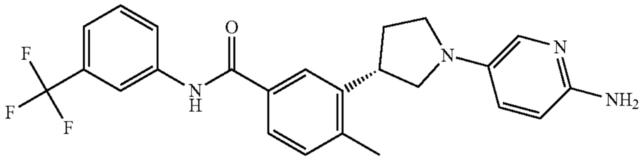 [SMILES: Cc1ccc(C(=O)Nc2cccc(C(F)(F)F)c2)cc1[C@@H]1CCN(c2ccc(N)nc2)C1] | (S)-3-(1-(6-aminopyridin-3-yl)pyrrolidin-3-yl)-4-methyl-N-(3-(trifluoromethyl) phenyl)benzamide |
| 61 | 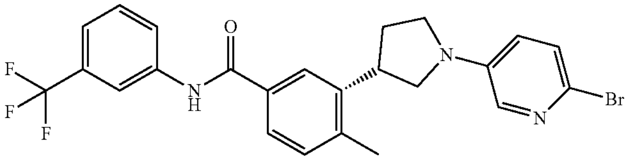 | (S)-3-(1-(6-bromopyridin-3-yl)pyrrolidin-3-yl)-4-methyl-N-(3-(trifluoromethyl) phenyl)benzamide |

In another preferred embodiment the present invention refers to a compound of formula (I) wherein Y is —C(O)— and A is A1

A1

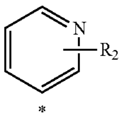

represented by formula (Ib)

(Ib)

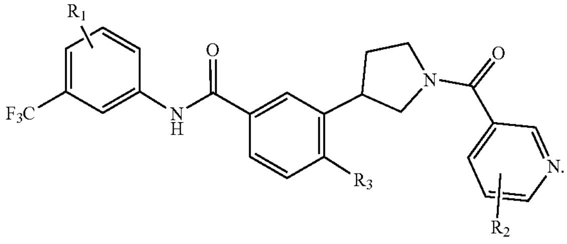

In a more preferred embodiment, the present invention relates to a compound of formula (Ib) wherein $R_1$ is hydrogen and $R_3$ is methyl, represented by formula (Ib)'

(Ib)'

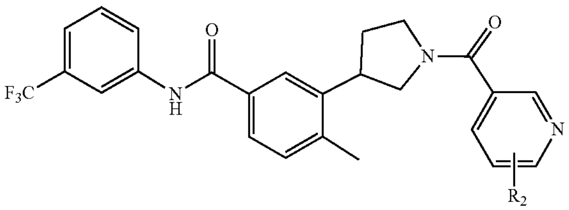

wherein $R_2$ is H or selected from the group consisting of halogen atoms, cyano, —C(O)$NH_2$, —C(O)NH—($C_1$-$C_6$)alkyl, —C(O)NH—($C_1$-$C_6$)alkylene-$NR_AR_B$, —C(O)NH—($C_1$-$C_6$)alkylene-$OR_A$, —NHC(O)$R_B$, —O—($C_1$-$C_6$) alkyl, —NH—($C_1$-$C_6$)alkylene-$OR_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more —($C_1$-$C_6$) alkyl;

$R_A$ is —$(C_1-C_6)$alkyl;

$R_B$ is —$(C_1-C_6)$alkyl;

and pharmaceutically acceptable salts thereof.

Most preferably, the invention refers to a compound of Formula (Ib) listed in Table 2 below and pharmaceutically acceptable salts thereof. This compound is particularly active on receptors DDR1 and DDR2, as shown in Table 5.

$(C_1-C_6)$alkylene-$OR_A$, —$NHC(O)R_B$, —O—$(C_1-C_6)$alkyl, —NH—$(C_1-C_6)$alkylene-$OR_A$, —C(O)NH—heterocycloalkyl, heterocycloalkyl, —$(C_1-C_6)$alkylene-heterocycloalkyl and —O—$(C_1-C_6)$alkylene-heterocycloalkyl, wherein each of said heterocycloalkyl is optionally substituted by one or more —$(C_1-C_6)$alkyl;

TABLE 2

| List of compounds of Formula (Ib) | | |
|---|---|---|
| Example No. | Structure | Chemical Name |
| 14 | 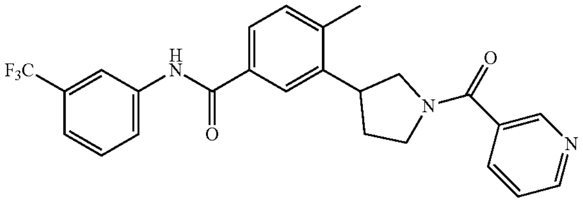 [SMILES: Cc1ccc(C(=O)Nc2cccc(C(F)(F)F)c2)cc1C1CCN(C(=O)c2cccnc2)C1] | 4-methyl-3-(1-nicotinoylpyrrolidin-3-yl)-N-(3-(trifluoromethyl)phenyl)benzamide |

In another preferred embodiment the present invention refers to a compound of formula (I) wherein Y is absent and A is A2

A2

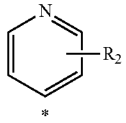

represented by formula (Ic)

(Ic)

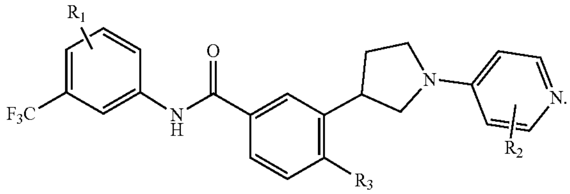

In a more preferred embodiment, the present invention relates to a compound of formula (Ic) wherein $R_1$ is hydrogen and $R_3$ is methyl, represented by formula (Ic)'

(Ic)'

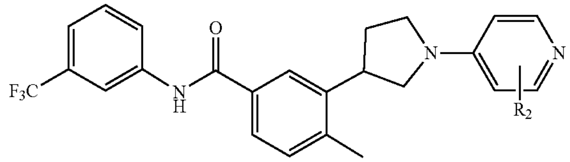

wherein $R_2$ is H or selected from the group consisting of halogen atoms, cyano, —$C(O)NH_2$, —C(O)NH—$(C_1-C_6)$alkyl, —C(O)NH—$(C_1-C_6)$alkylene-$NR_AR_B$, —C(O)NH—

$R_A$ is —$(C_1-C_6)$alkyl;

$R_B$ is —$(C_1-C_6)$alkyl;

and pharmaceutically acceptable salts thereof.

In another preferred embodiment the present invention refers to a compound of formula (Ic) wherein A is A2a A2a

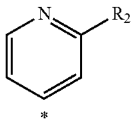

represented by formula (Ica)

(Ica)

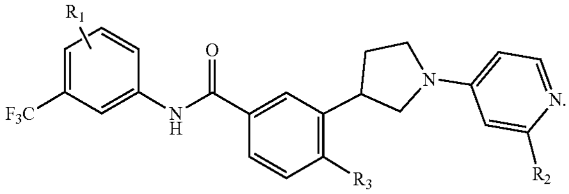

In a more preferred embodiment, the present invention relates to a compound of formula (Ica) wherein $R_1$ is hydrogen and $R_3$ is methyl, represented by formula (Ica)'

(Ica)'

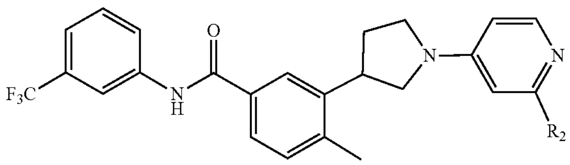

wherein $R_2$ is H or selected from the group consisting of halogen atoms, cyano, —$C(O)NH_2$, —C(O)NH—$(C_1-C_6)$alkyl, —C(O)NH—$(C_1-C_6)$alkylene-$NR_AR_B$, —C(O)NH—

($C_1$-$C_6$)alkylene-$OR_A$, —NHC(O)$R_B$, —O—($C_1$-$C_6$)alkyl, —NH—($C_1$-$C_6$)alkylene-$OR_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more —($C_1$-$C_6$)alkyl;

$R_A$ is —($C_1$-$C_6$)alkyl;

$R_B$ is —($C_1$-$C_6$)alkyl;

and pharmaceutically acceptable salts thereof.

In an even more preferred embodiment the present invention refers to a compound of formula (Ica) or (Ica)', wherein $R_2$ is H, N-methylcarbamoyl, carbamoyl, cyano or acetamido.

Most preferably, the invention refers to at least one of the compounds of Formula (Ica) listed in Table 3 below and pharmaceutically acceptable salts thereof. These compounds are particularly active on receptors DDR1 and DDR2, as shown in Table 5.

TABLE 3

List of compounds of Formula (Ica)

| Example No. | Structure | Chemical Name |
|---|---|---|
| 1 | 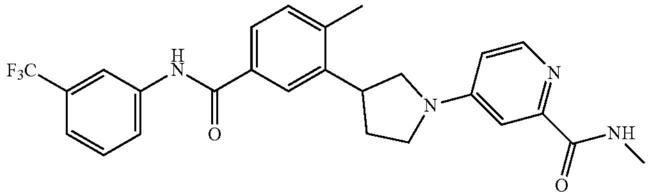 [SMILES: CNC(=O)c1cc(N2CCC(c3cc(C(=O)Nc4cccc(C(F)(F)F)c4)ccc3C)C2)ccn1] | N-methyl-4-(3-(2-methyl-5-((3-(trifluoromethyl)phenyl)carbamoyl)phenyl)pyrrolidin-1-yl)picolinamide |
| 24 | 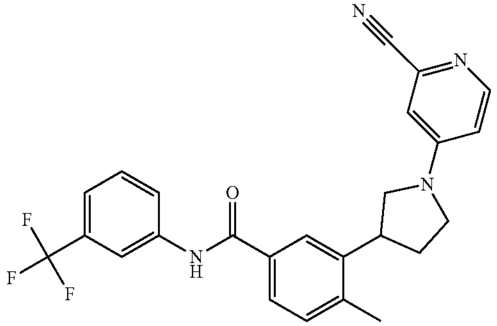 [SMILES: Cc1ccc(C(=O)Nc2cccc(C(F)(F)F)c2)cc1C1CCN(c2ccnc(C#N)c2)C1] | 3-(1-(2-cyanopyridin-4-yl)pyrrolidin-3-yl)-4-methyl-N-(3-(trifluoromethyl)phenyl)benzamide |
| 25 | 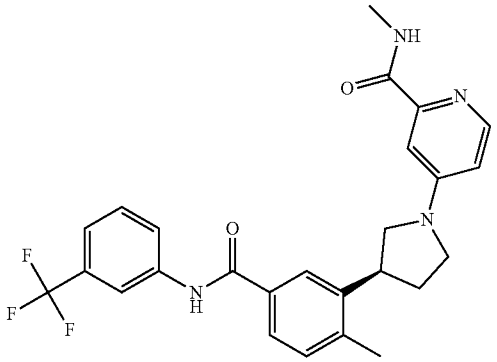 [SMILES: CNC(=O)c1cc(N2CC[C@@H](c3cc(C(=O)Nc4cccc(C(F)(F)F)c4)ccc3C)C2)ccn1] | (S)-N-methyl-4-(3-(2-methyl-5-((3-(trifluoromethyl)phenyl)carbamoyl)phenyl)pyrrolidin-1-yl)picolinamide |
| 27 | 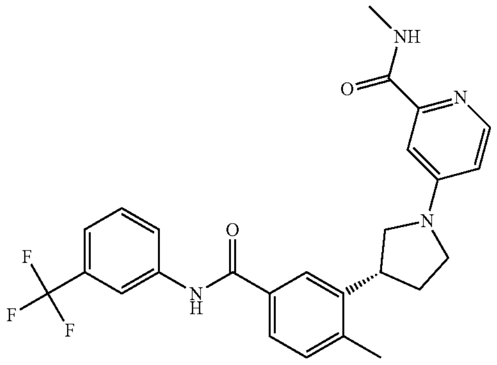 [SMILES: CNC(=O)c1cc(N2CC[C@H](c3cc(C(=O)Nc4cccc(C(F)(F)F)c4)ccc3C)C2)ccn1] | (R)-N-methyl-4-(3-(2-methyl-5-((3-(trifluoromethyl)phenyl)carbamoyl)phenyl)pyrrolidin-1-yl)picolinamide |

TABLE 3-continued

List of compounds of Formula (Ica)

| Example No. | Structure | Chemical Name |
|---|---|---|
| 41 | 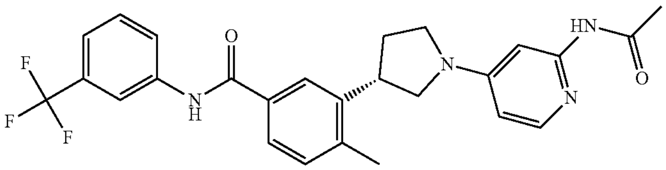 [SMILES: CC(=O)Nc1cc(N2CC[C@@H](c3cc(C(=O)Nc4cccc(C(F)(F)F)c4)ccc3C)C2)ccn1] | (S)-3-(1-(2-acetamidopyridin-4-yl)pyrrolidin-3-yl)-4-methyl-N-(3-(trifluoromethyl)phenyl) benzamide |
| 53 | 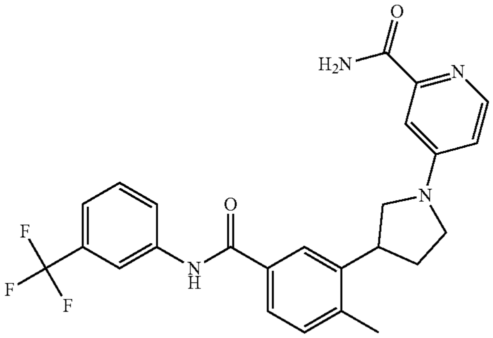 [SMILES: Cc1ccc(C(=O)Nc2cccc(C(F)(F)F)c2)cc1C1CCN(c2ccnc(C(N)=O)c2)C1] | 4-(3-(2-methyl-5-((3-(trifluoromethyl)phenyl) carbamoyl)phenyl)pyrrolidin-1-yl)picolinamide |
| 54 | 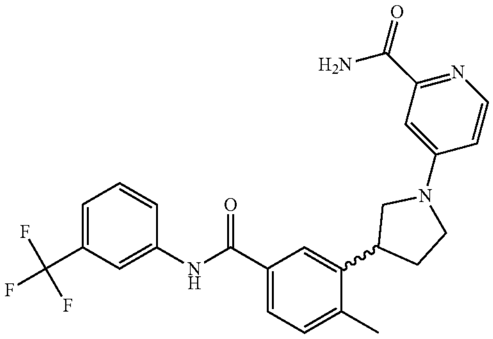 [SMILES: Cc1ccc(C(=O)Nc2cccc(C(F)(F)F)c2)cc1C1CCN(c2ccnc(C(N)=O)c2)C1] | 4-(3-(2-methyl-5-((3-(trifluoromethyl)phenyl) carbamoyl)phenyl)pyrrolidin-1-yl)picolinamide First eluting |
| 55 | 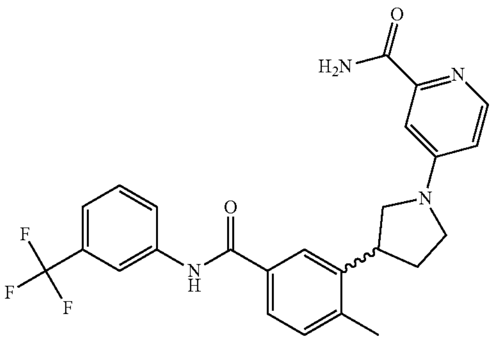 [SMILES: Cc1ccc(C(=O)Nc2cccc(C(F)(F)F)c2)cc1C1CCN(c2ccnc(C(N)=O)c2)C1] | 4-(3-(2-methyl-5-((3-(trifluoromethyl)phenyl) carbamoyl)phenyl)pyrrolidin-1-yl)picolinamide Second eluting |

In another preferred embodiment the present invention refers to a compound of formula (I) wherein Y is absent and A is A3

A3

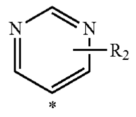

represented by formula (Id)

(Id)

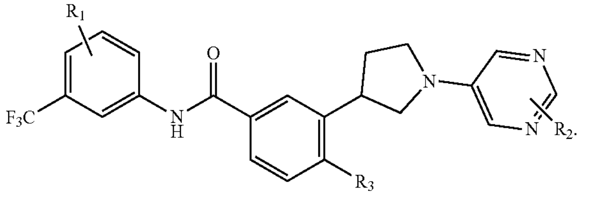

In a more preferred embodiment, the present invention relates to a compound of formula (Id) wherein $R_1$ is hydrogen and $R_3$ is methyl, represented by formula (Id)'

(Id)'

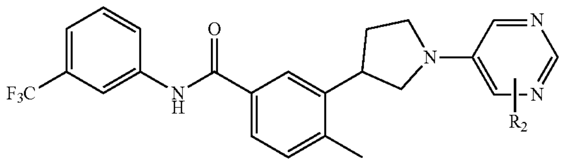

wherein $R_2$ is H or selected from the group consisting of halogen atoms, cyano, —C(O)$NH_2$, —C(O)NH—($C_1$-$C_6$)alkyl, —C(O)NH—($C_1$-$C_6$)alkylene-$NR_AR_B$, —C(O)NH—($C_1$-$C_6$)alkylene-$OR_A$, —NHC(O)$R_B$, —O—($C_1$-$C_6$)alkyl, —NH—($C_1$-$C_6$)alkylene-$OR_A$, —C(O)NH—heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more —($C_1$-$C_6$) alkyl;

$R_A$ is —($C_1$-$C_6$)alkyl;

$R_B$ is —($C_1$-$C_6$)alkyl;

and pharmaceutically acceptable salts thereof.

Most preferably, the invention refers to at least one of the compounds of Formula (Id) listed in Table 4 below and pharmaceutically acceptable salts thereof. These compounds are particularly active on receptors DDR1 and DDR2, as shown in Table 5.

TABLE 4

List of compounds of Formula (Id)

| Example No. | Structure | Chemical Name |
|---|---|---|
| 20 | 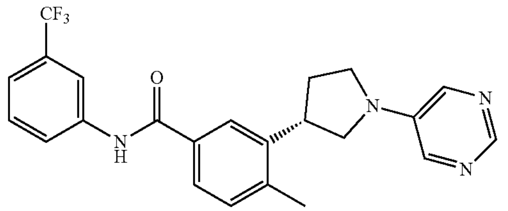 [SMILES: Cc1ccc(C(=O)Nc2cccc(C(F)(F)F)c2)cc1[C@@H]1CCN(c2cncnc2)C1] | (S)-4-methyl-3-(1-(pyrimidin-5-yl)pyrrolidin-3-yl)-N-(3-(trifluoromethyl)phenyl)benzamide |
| 48 | 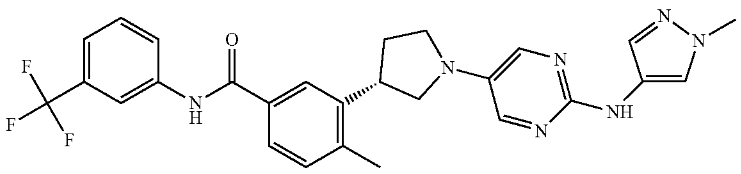 [SMILES: Cc1ccc(C(=O)Nc2cccc(C(F)(F)F)c2)cc1[C@@H]1CCN(c2cnc(Nc3cnn(C)c3)nc2)C1] | (S)-4-methyl-3-(1-(2-((1-methyl-1H-pyrazol-4-yl)amino)pyrimidin-5-yl)pyrrolidin-3-yl)-N-(3-(trifluoromethyl)phenyl)benzamide |
| 49 | 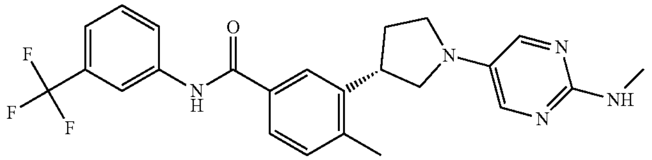 [SMILES: CNc1ncc(N2CC[C@@H](c3cc(C(=O)Nc4cccc(C(F)(F)F)c4)ccc3C)C2)cn1] | (S)-4-methyl-3-(1-(2-(methylamino)pyrimidin-5-yl)pyrrolidin-3-yl)-N-(3-(trifluoromethyl)phenyl)benzamide |
| 51 | 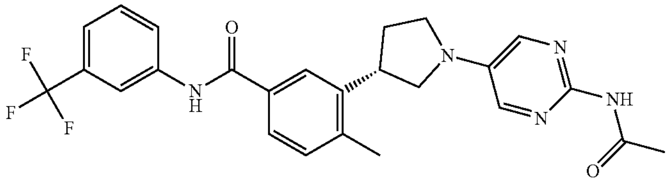 [SMILES: CC(=O)Nc1ncc(N2CC[C@@H](c3cc(C(=O)Nc4cccc(C(F)(F)F)c4)ccc3C)C2)cn1] | (S)-3-(1-(2-acetamidopyrimidin-5-yl)pyrrolidin-3-yl)-4-methyl-N-(3-(trifluoromethyl)phenyl)benzamide |

In another preferred embodiment the present invention refers to a compound of formula (I) wherein Y is absent and A is bicyclic heteroaryl substituted by $R_2$, as defined above, referred to as a compound of formula (Ie).

More preferably, the invention refers to at least one of the compounds of Formula (Ie) listed in Table 4a below and pharmaceutically acceptable salts thereof. These compounds are particularly active on receptors DDR1 and DDR2, as shown in Table 5.

TABLE 4a

List of compounds of Formula (Ie)

| Example No. | Structure | Chemical Name |
|---|---|---|
| 42 | 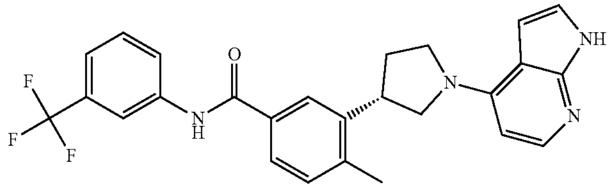 [SMILES: Cc1ccc(C(=O)Nc2cccc(C(F)(F)F)c2)cc1[C@@H]1CCN(c2ccnc3[nH]ccc23)C1] | (S)-3-(1-(1H-pyrrolo[2,3-b]pyridin-4-yl)pyrrolidin-3-yl)-4-methyl-N-(3-(trifluoromethyl)phenyl) benzamide |
| 43 | 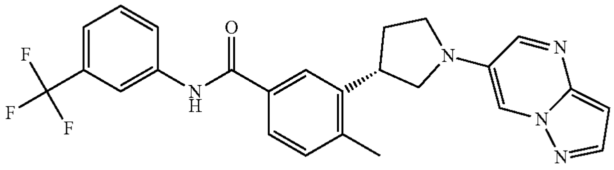 [SMILES: Cc1ccc(C(=O)Nc2cccc(C(F)(F)F)c2)cc1[C@@H]1CCN(c2cnc3ccnn3c2)C1] | (S)-4-methyl-3-(1-(pyrazolo[1,5-a]pyrimidin-6-yl)pyrrolidin-3-yl)-N-(3-(trifluoromethyl)phenyl) benzamide |

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimal reaction conditions may vary depending on the particular reactants or solvent used, such conditions can be readily determined by those skilled in the art by routine optimization procedures. Thus, processes described below should not be viewed as limiting the scope of the synthetic methods available for the preparation of the compounds of the invention.

In some cases, generally known protective groups (PG) could be employed when needed to mask or protect sensitive or reactive moieties, in accordance to general principles of chemistry (Protective group in organic syntheses, 3rd ed. T. W. Greene, P. G. M. Wuts).

Compounds of formula (I) may be prepared according to Schemes 1 to 5 as described hereinafter providing at least one non-limiting synthetic route for the preparation of all examples.

In one embodiment of the present invention, compounds of formula (I) may be prepared as described in Scheme 1, starting from commercially available compound (II).

Scheme 1

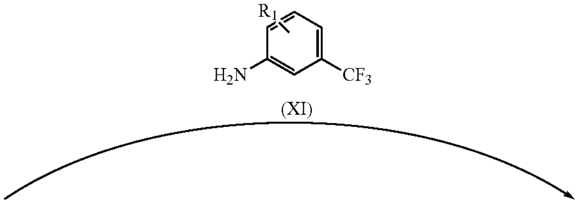

(XI)

-continued
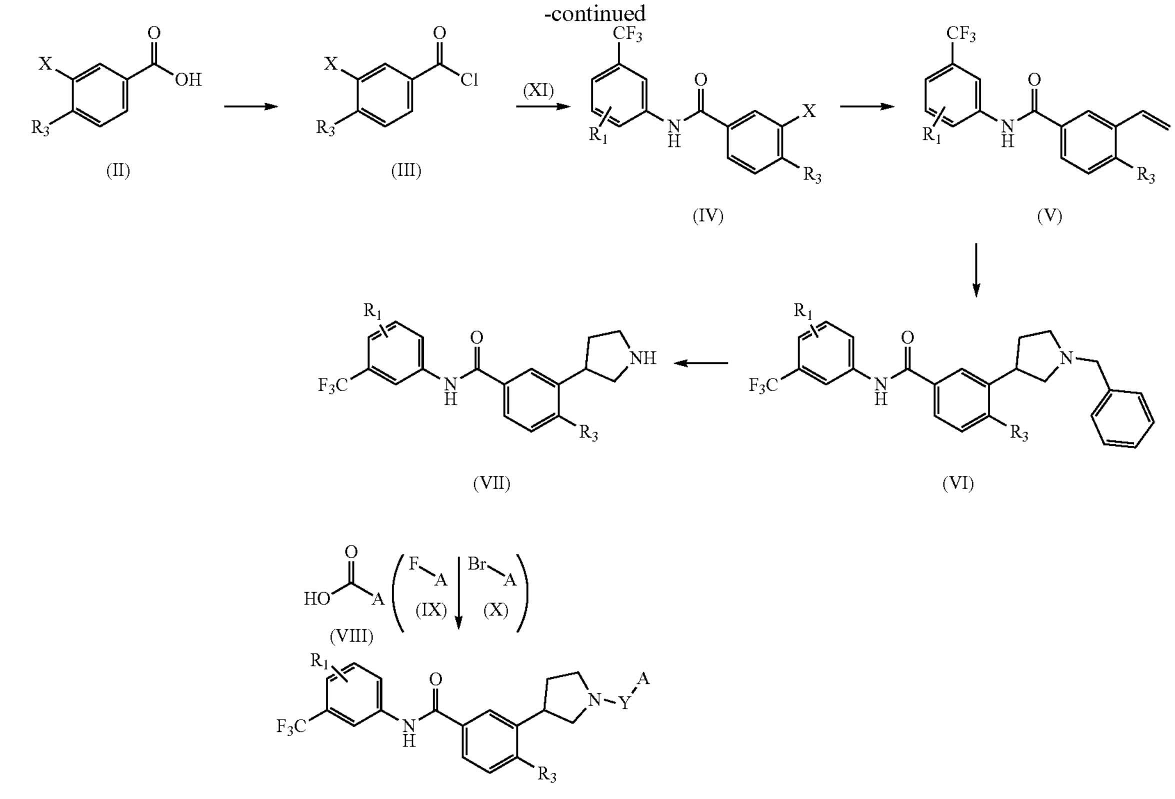
(II) (III) (IV) (V) (VI) (VII) (VIII) (IX) (X) (I)
X = I, Br
In one preferred embodiment, compounds of formula (I) wherein $R_1$ is hydrogen and $R_3$ is methyl, represented by formula (I)', as defined above, may be prepared as described in Scheme 2, starting from commercially available compound (II)'.
Scheme 2
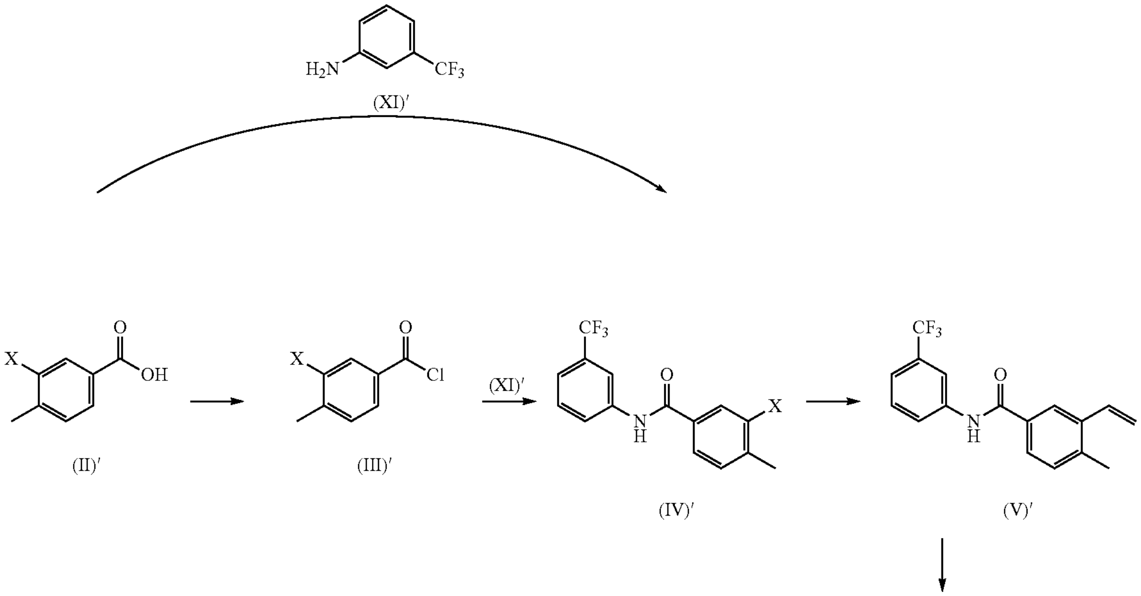
(XI)' (II)' (III)' (IV)' (V)'

-continued

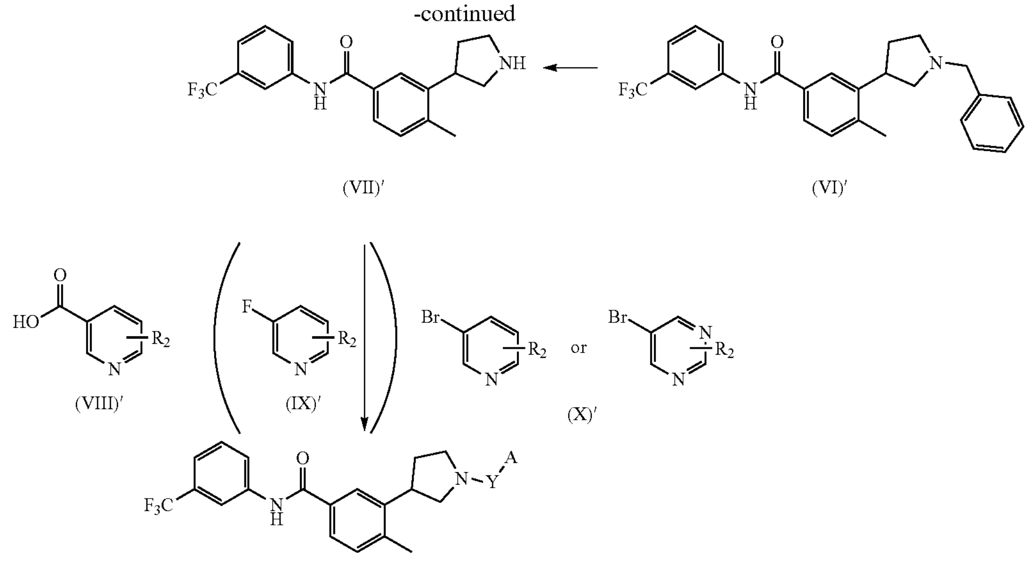

(VII)' (VI)'

(VIII)' (IX)' or (X)'

(I)'

X = I, Br

A compound of formula (IV) or (IV)' can be prepared from a compound of formula (II) or (II)', respectively, by converting it into the acyl chloride (III) or (III)' using oxalyl chloride or thionyl chloride in a suitable solvent such as DMF or DCM, and performing subsequently an amide coupling with aryl amine (XI) or (XI)' using a suitable base, such as DIPEA, in a suitable solvent, such as DCM, at RT. In a different approach, a compound of formula (IV) or (IV)' may be prepared by following a one-step synthesis starting from a compound of formula (II) or (II)', under suitable amide coupling reaction conditions. For example, a compound of formula (II) or (II)' and aryl amine (XI) or (XI)' may be reacted in the presence of an activating agent, such as HATU or TBTU, with an organic base, such as DIPEA or TEA, in a suitable organic solvent, such as DCM or DMF, and at a temperature generally around RT for a time ranging from a few hours to overnight.

A compound of formula (V) or (V)' may be obtained from a compound of formula (IV) or (IV)' through a palladium-catalyzed cross-coupling on the leaving group X, wherein X can be bromide or iodide. For example, the reaction may be carried out by reacting a compound of formula (IV) or (IV)' with potassium trifluoro(vinyl)borate following the classical Suzuki protocol, in a suitable organic solvent, such as dioxane or THF, in the presence of an inorganic base, such as $K_2PO_4$ or $Cs_2CO_3$, with an appropriate palladium catalytic system, such as $Pd_2(dppf)Cl_2$ or another palladium source/phosphine-based ligand, at high temperature (around 100° C.) for a few hours.

1,3-dipolar cycloaddition may be carried out reacting the α,β-unsaturated compound of formula (V) or (V)' with a 1,3-dipole or a suitable precursor, such as an azomethine ylide, for example N-benzyl-1-methoxy-N-((trimethylsilyl)methyl) methanamine, under acid catalysis, such as TFA, in a solvent such as dioxane. The compound of formula (VI) or (VI)' can be converted into the debenzylated compound of formula (VII) or (VII)' by reduction under hydrogen atmosphere, typically 7-10 bar, in presence of a suitable catalyst such as Pd/C in a suitable solvent, such as, but not limited to, EtOH or MeOH at a temperature ranging from RT to 60° C., for few hours.

A compound of formula (I) or (I)', wherein Y is —C(O)—, may be prepared with a one-step synthesis by starting from a compound of formula (VII) or (VII)' and a carboxylic acid compound of formula (VIII) or (VIII)', under suitable amide coupling reaction conditions in the presence of an activating agent, such as HATU or TBTU, with an organic base, such as DIPEA or TEA, in a suitable organic solvent, such as DCM or DMF, and at a temperature generally around RT for a time ranging from a few hours to overnight.

Differently, a compound of formula (VII) or (VII)' may be converted into a compound of formula (I) or (I)', wherein Y is absent, by performing a Buchwald cross-coupling reaction, using a bromide compound of formula (X) or (X)', in a suitable organic solvent, such as dioxane or toluene or DMA, in the presence of an inorganic base, such as $K_2PO_4$ or $Cs_2CO_3$, with a suitable palladium catalytic system such as $Pd(dba)_2$/RuPhos or another palladium source/phosphine-based ligand at variable temperature from 100 to 150° C., for a period ranging from few hours to overnight.

In a different approach, a compound of formula (VII) or (VII)' may be converted into a compound of formula (I) or (I)', wherein Y is absent, by performing a nucleophilic aromatic substitution using a fluoride compound of formula (IX) or (IX)', in a suitable organic solvent, such as DMSO, in the presence of an inorganic base, such as $Cs_2CO_3$ or $K_2CO_3$, at a temperature variable from 80 to 110° C., for a period ranging from few hours to overnight.

It is intended that in the present description a compound of formula (I)' is an embodiment of a compound of formula (I). Analogously, a compound of formula (II)' or (III)' or (IV)' or (V)' or (VI)' or (VII)' or (VIII)' or (IX)' or (X)' is and embodiment of a compound of formula (II) or (III) or (IV) or (V) or (VI) or (VII) or (VIII) or (IX) or (X), respectively.

A compound of formula (I) or (I)' comprises a stereogenic center, which is the carbon atom of the pyrrolidine ring linked to the phenyl moiety. A compound of formula (I) or (I)' prepared according to the approach depicted in Scheme 1 or 2, respectively, is provided as a racemic mixture. Intermediate compounds of formula (VI) or (VI)' and of formula (VII) or (VII)' are provided as racemic mixtures.

Separation of the racemic mixtures may be achieved by chiral resolution methods, such as chiral purification. Both single enantiomers of a compound of formula (I) or (I)', as well as its racemic mixture, are included in the scope of the present invention.

Scheme 3

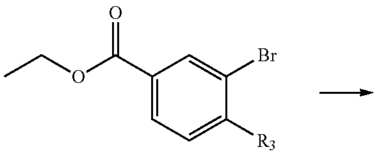

(XII)

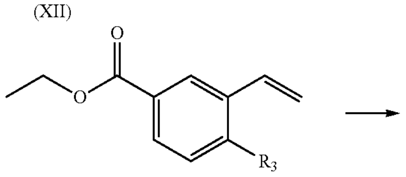

(XIII)

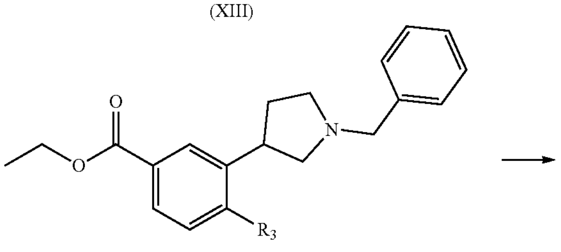

(XIV)

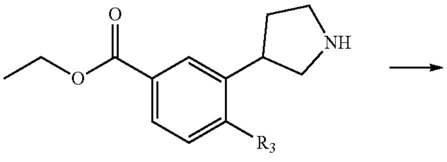

(XV)

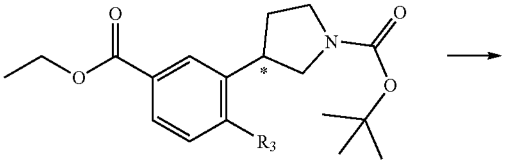

(XVI)

-continued

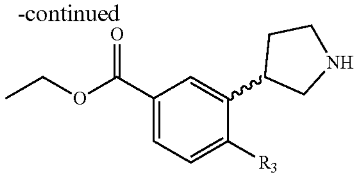

(XV)

In a different approach, as depicted in Scheme 3, intermediate compounds of formula (XV) may be obtained by starting from commercially available compounds of formula (XII). A compound of formula (XIII) may be prepared from a compound of formula (XII) through a palladium-catalyzed cross-coupling reaction. The reaction may be carried out by reacting a compound of formula (XII) with potassium trifluoro(vinyl)borate following the classical Suzuki protocol, in a suitable organic solvent, such as dioxane, in the presence of an inorganic base, such as $Cs_2CO_3$, with an appropriate palladium catalytic system, such as $Pd_2(dppf)Cl_2$, at high temperature (around 100° C.) for few hours. 1,3-dipolar cycloaddition may be carried out reacting the α,β-unsaturated compound of formula (XIII) with a 1,3-dipole or a suitable precursor, such as an azomethine ylide, for example N-benzyl-1-methoxy-N-((trimethylsilyl) methyl)methanamine, under acid catalysis, such as by TFA, in a suitable solvent, such as dioxane. The resulting compound of formula (XIV) may be converted into the debenzylated compound of formula (XV) by reduction under hydrogen atmosphere, typically 4 bar, in the presence of a suitable catalyst such as Pd/C in a suitable solvent such as, but not limited to, EtOH at a temperature ranging from RT to 60° C., for few hours. Boc-protected compound of formula (XVI) may be prepared by reacting a compound of formula (XV) with di-tert-butyl dicarbonate, under basic conditions using an organic base, such as TEA, in an appropriate solvent, such as DCM. Compounds of formula (XIV), (XV) and (XVI) are provided as racemic mixtures (depicted in the Schemes with solid bonds). The stereogenic center, which is the carbon atom of the pyrrolidine ring linked to the phenyl moiety, is indicated with a * in the compound of formula (XVI) in Scheme 3. Separation of the racemic mixture of the compounds of formula (XVI) is achieved by chiral resolution methods such as chiral purification, resulting in compounds of formula (XVI) as single enantiomers (not depicted in Scheme 3). Compounds of formula (XV) as single enantiomers (depicted in Scheme 3 with a wavy bond) may then be obtained from single enantiomers of compounds of formula (XVI) by removing the Boc protecting group in non-racemizing conditions such as acidic conditions, for instance by using an organic acid, such as TFA.

Scheme 4

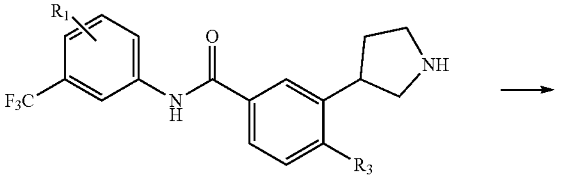

(VII)

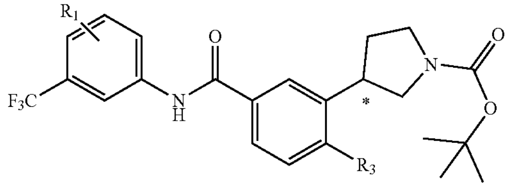

(XVII)

-continued

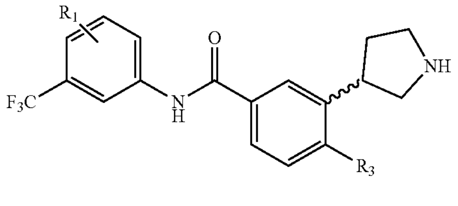

(VII)

Analogously, as depicted in Scheme 4, compounds of formula (XVII) may be prepared by reacting a compound of formula (VII) with di-tert-butyl dicarbonate, under basic conditions by using an organic base, such as TEA, in an suitable solvent, such as DCM. Compounds of formula (XVII) are provided as racemic mixtures (depicted in the Schemes with solid bonds). Separation of the racemic mixture of the compounds of formula (XVII) is achieved by chiral resolution methods such as chiral purification, resulting in compounds of formula (XVII) as single enantiomers (not depicted in Scheme 3). Compounds of formula (VII) as single enantiomers (depicted in Scheme 4 with a wavy bond) may then be obtained from single enantiomers of compounds of formula (XVII) by removing the Boc protecting group in non-racemizing conditions such as acidic conditions, for instance by using an organic acid, such as TFA.

Compounds of formula (I), or compounds of formula (I)', as single enantiomers may then be obtained by starting from single enantiomers of intermediate compounds of formula (XV) or from single enantiomers of intermediate compounds of formula (VII), obtained as described above and as depicted in Scheme 3 and Scheme 4, respectively.

Scheme 5

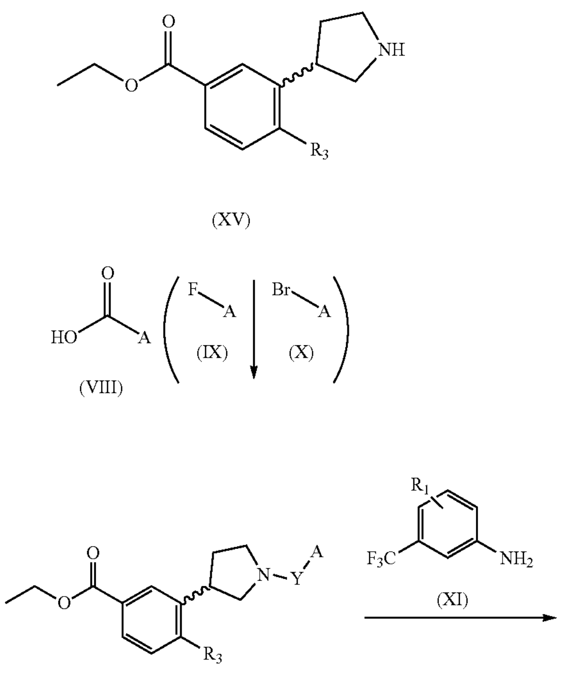

(XV)

(VIII)

(IX)

(X)

(XI)

(XVIII)

-continued

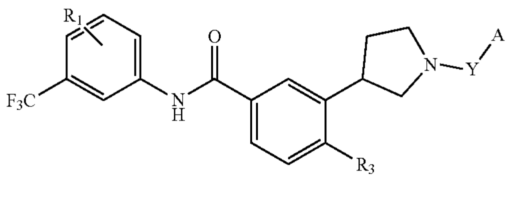

(I)

Analogously to what described referring to Scheme 1, a single enantiomer of an intermediate compound of formula (XV) may react with a carboxylic acid compound of formula (VIII) or with a fluoride compound of formula (IX) or with a bromide compound of formula (X), in the conditions described above, respectively, to obtain a compound of formula (XVIII) as single enantiomer. As a final step, a transamidation reaction of a compound of formula (XVIII) with a suitable aryl amine of formula (XI) in the presence of a strong base, such as BuLi, LiHIMIDS or LDA, in an appropriate solvent, like THF, provides a compound of formula (I), as single enantiomer.

In a different approach, compounds of formula (I) as single enantiomers may be obtained from single enantiomers of compounds of formula (VII) reacting with a carboxylic acid compound of formula (VIII) or with a fluoride compound of formula (IX) or with a bromide compound of formula (X), in the conditions described referring to Scheme 1.

A compound of formula (I) may be further reacted performing a conversion of a functional group into a different functional group thus obtaining another compound of formula (I). For instance, a nitrile, or cyano group, may be converted into an amide group in a suitable organic solvent, such as DMSO, in the presence of a peroxide, such as hydrogen peroxide (see for instance the preparation of Example 17 from Example 4).

In a different approach, a conversion of a functional group into a different functional group may be carried out as intermediate step, for instance in the preparation of a compound of formula (I) according to Scheme 5 and involving an intermediate compound of formula (XVII). After such conversion of a functional group, as a final step, a compound of formula (XVII) may undergo a transamidation reaction with a suitable aryl amine of formula (XI), thus providing a compound of formula (I).

Accordingly, the present invention provides a process for the preparation of a compound of formula (I), or a pharmaceutically acceptable salt thereof, comprising the step of:

a) reacting a compound of formula (V)

(V)

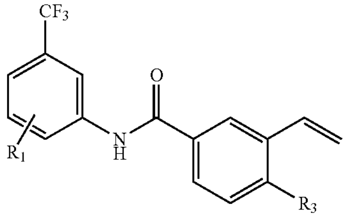

with N-benzyl-1-methoxy-N-((trimethylsilyl)methyl)methanamine

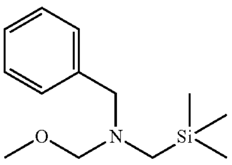 [SMILES: COCN(Cc1ccccc1)C[Si](C)(C)C]

under acid catalysis in the presence of a solvent such as to obtain a compound of formula (VI)

(VI)

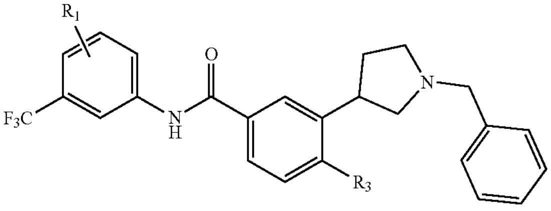

wherein $R_1$ and $R_3$ are as defined above, and converting the compound of formula (VI) into a compound of formula (I).

In a preferred embodiment, the process further comprises the steps of:

b) cleaving the benzyl group of the compound of formula (VI) such as to obtain a compound of formula (VII):

(VII)

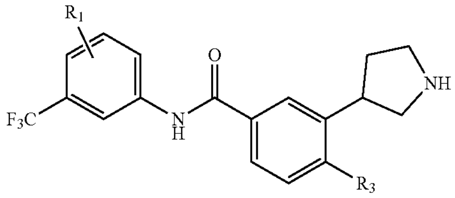

by reduction under hydrogen atmosphere in the presence of a Pd catalyst; and c) reacting the compound of formula (VII) with a carboxylic acid compound of formula (VIII) or a fluoride compound of formula (IX) or a bromide compound of formula (X), such as to obtain a compound of formula (I).

Accordingly, the present invention provides a compound of formula (VI)

(VI)

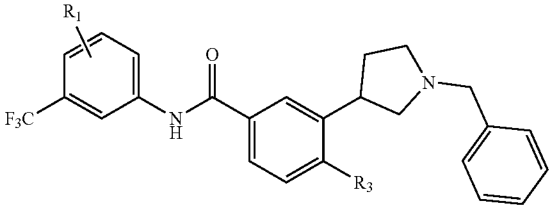

wherein $R_1$ and $R_3$ are as defined above.

The invention further provides the use of the compound of formula (VI) as defined above in the preparation of a compound of formula (I).

The present invention also provides a compound of formula (VII)

(VII)

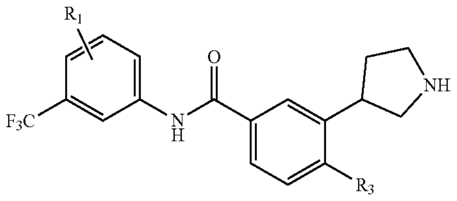

wherein $R_1$ and $R_3$ are as defined above.

The invention further provides the use of the compound of formula (VII) as defined above in the preparation of a compound of formula (I).

Thus, the invention provides the use of the compound of formula (VI) and/or the compound of formula (VII) as defined above in the preparation of a compound of formula (I).

The compounds of formula (I) of the present invention have surprisingly been found to effectively inhibit both receptor DDR1 and DDR2. Advantageously, the inhibition of receptors DDR1 and DDR2 may result in efficacious treatment of the diseases or condition wherein the DDR receptors are involved.

In this respect, it has now been found that the compounds of formula (I) of the present invention have an antagonist drug potency expressed as inhibition constant Ki on DDR1 and DDR2 between 60 and 25 nM, as shown in the present experimental part.

Preferably, the compounds of the present invention have a Ki on DDR1 and DDR2 between 25 and 10 nM. Even more preferably, the compounds of the present invention have a Ki on DDR1 and DDR2 lower than 10 nM.

In one aspect, the present invention refers to a compound of formula (I) according to any of the embodiments disclosed above for use as a medicament.

In a preferred embodiment, the invention refers to a compound of formula (I), and pharmaceutically acceptable salts thereof, for use in treating diseases, disorders, or conditions associated with dysregulation of DDR.

In another aspect, the invention refers to the use of a compound of formula (I) as above described, and pharmaceutically acceptable salts thereof, in the preparation of a medicament for the treatment of disorders associated with dysregulation of DDR.

In another preferred embodiment, the invention refers to a compound of formula (I) or a pharmaceutically acceptable salt thereof, for use in the prevention and/or treatment of a disease, disorder or condition associated with DDR receptor mechanism. In a more preferred embodiment, the present invention refers to a compound of formula (I) useful for the prevention and/or treatment of fibrosis and/or diseases, disorders, or conditions that involve fibrosis.

The terms "fibrosis" or "fibrosing disorder," as used herein, refer to conditions that are associated with the abnormal accumulation of cells and/or fibronectin and/or collagen and/or increased fibroblast recruitment and include, but are not limited to, fibrosis of individual organs or tissues such as the heart, kidney, liver, joints, lung, pleural tissue, peritoneal tissue, skin, cornea, retina, musculoskeletal and digestive tract.

Preferably, the compounds of formula (I) as above described are useful for the treatment and/or prevention of fibrosis such as pulmonary fibrosis, idiopathic pulmonary fibrosis (IPF), hepatic fibrosis, renal fibrosis, ocular fibrosis, cardiac fibrosis, arterial fibrosis and systemic sclerosis.

More preferably, the compounds of formula (I) as above described are useful for the treatment of idiopathic pulmonary fibrosis (IPF).

In one aspect, the invention also refers to a method for the prevention and/or treatment of disorders associated with DDR receptors mechanisms, said method comprises administering to a patient in need of such treatment a therapeutically effective amount of a compound of formula (I) as above described.

In a further aspect, the invention refers to the use of a compound of formula (I) as above described for the treatment of disorders associated with DDR receptors mechanism.

In another aspect, the invention refers to the use of a compound of formula (I) as above described in the preparation of a medicament for the treatment of disorders associated with DDR receptors mechanism.

In a further aspect, the invention refers to a method for the prevention and/or treatment of disorder or condition associated with dysregulation of DDR receptors 1 and 2, said method comprising administering a patient in need of such treatment a therapeutically effective amount of a compound of formula (I) as above described.

In a further aspect, the present invention refers to the use of a compound of formula (I) as above described for the treatment of a disease, disorder or condition associated with dysregulation of DDR receptors 1 and 2.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and that can nevertheless be routinely determined by the skilled artisan.

The compounds of formula (I) may be administered once or according to a dosing regimen wherein a number of doses are administered at varying intervals of time for a given period of time. Typical daily dosages may vary depending upon the route of administration chosen.

The present invention also refers to a pharmaceutical composition comprising a compound of formula (I) according to any of its embodiment in admixture with at least one or more pharmaceutically acceptable carrier or excipient.

In one embodiment, the invention refers to a pharmaceutical composition of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably, the compounds of the present invention are administered orally or by inhalation.

In one preferred embodiment, the pharmaceutical composition comprising the compound of formula (I) is a solid oral dosage form such as tablets, gelcaps, capsules, caplets, granules, lozenges and bulk powders.

In one embodiment, the pharmaceutical composition comprising the compound of formula (I) is a tablet.

The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like.

In a further embodiment, the pharmaceutical composition comprising a compound of formula (I) is a liquid oral dosage form such as aqueous and non-aqueous solutions, emulsions, suspensions, syrups, and elixirs. Such liquid dosage forms can also contain suitable known inert diluents such as water and suitable known excipients such as preservatives, wetting agents, sweeteners, flavorants, as well as agents for emulsifying and/or suspending the compounds of the invention.

In a further embodiment, the pharmaceutical composition comprising the compound of formula (I) is an inhalable preparation such as inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

The compounds of the invention can be administered as the sole active agent or in combination with other pharmaceutical active ingredients.

The dosages of the compounds of the invention depend upon a variety of factors including among others the particular disease to be treated, the severity of the symptoms, the route of administration and the like.

The invention is also directed to a device comprising a pharmaceutical composition comprising a compound of Formula (I) according to the invention, in form of a single- or multi-dose dry powder inhaler or a metered dose inhaler.

All preferred groups or embodiments described above for compounds of formula (I) may be combined with each other and apply as well mutatis mutandis.

The various aspects of the invention described in this application are illustrated by the following examples which are not meant to limit the invention in any way.

Experimental Part

Chemical Names of the compounds were generated with Structure To Name Place IUPAC Name by PerkinElmer ChemDraw Professional 19.1.1.21. All reagents, for which the synthesis is not described in the experimental part, are either commercially available, or are known compounds or may be formed from known compounds by known methods by a person skilled in the art.

In the procedures that follow, some of the starting materials are identified through an "Intermediate" or "Example" number with indications on step number. This is provided merely for assistance to the skilled chemist.

A "similar" or "analogous" procedure means that such a procedure may involve minor variations, for example reaction temperature, reagent/solvent amount, reaction time, work-up conditions or chromatographic purification conditions.

Abbreviations

TEA=triethylamine; CV=Column Volumes; DMF=dimethylformamide; DMA=dimethylacetamide; Et2O=diethyl ether; THE=tetrahydrofuran; DCM=dichloromethane; ACN=acetonitrile; MeOH=methyl alcohol; EtOH=ethanol; tBu=tert-butyl; EtOAc=ethyl acetate; Boc=tert-butyloxycarbonyl; rt/RT=room temperature; LC-MS=Liquid Chromatography/Mass Spectrometry; MW=Microwave; SCX=solid cation exchange; DMSO-d6=deuterated dimethyl sulfoxide; SFC=supercritical fluid chromatography; CDCl3=deuterated chloroform; NMR=nuclear magnetic resonance; DIPEA=diisopropylethylamine; HCOOH=formic acid; TBTU=O-(benzotriazol-1-yl)-N,N,N',N'-tetramethyluronium tetrafluoroborate; UPLC=Ultra Performance Liquid Chromatography; Pd(dppf)$Cl_2$=[1,1'-bis(diphenylphosphino)ferrocene] dichloropalladium(II); RuPhos=2-dicyclohexylphosphino-2',6'-diisopropoxybiphenyl; BINAP=2,2'-bis(diphenylphosphino)-1,1'-binaphthalene; $t_R$=retention time; Pd$(dba)_2$=bis (dibenzylideneacetone)palladium(0); STAB=sodium triacetoxyborohydride; AcOH=acetic acid; FCC=flash column chromatography; SM=starting material; eq.=equivalents; ee=enantiomeric excess; h=hour/s; min=minute/s; Pd-171=RuPhos Pd(crotyl)Cl; Pd-170=Pd (crotyl)(XPhos)Cl; XPhos=2-dicyclohexylphosphino-2',4',6'-triisopropylbiphenyl: XPhos Pd G3=(2-dicyclohexylphosphino-2',4',6'-triisopropyl-1,1'-biphenyl)[2-(2'-amino-1,1'-biphenyl)]palladium(II) methanesulfonate; $H_2O_2$=hydrogen peroxide.

General Experimental Details

Nmr Characterization:

$^1$H NMR spectra were recorded on Varian MR-400 spectrometer operating at 400 MHZ (proton frequency), equipped with: a self-shielded Z-gradient coil 5 mm 1H/nX broadband probe head for reverse detection, deuterium digital lock channel unit, quadrature digital detection unit with transmitter offset frequency shift. Chemical shifts are reported as δ values in ppm relative to tetramethyl silane (TMS) as an internal standard. Coupling constants (J values) are given in hertz (Hz) and multiplicities are reported using the following abbreviation (s=singlet, d=doublet, t=triplet, q=quartet, dd=doublet of doublets, dt=doublet of triplets, m=multiplet, br=broad, nd=not determined).

LC/UV/MS Analytical Methods

LC/MS retention times are estimated to be affected by an experimental error of 0.5 min.

Method 1: Acquity CSH $C_{18}$ column 50 mm×2.1 mm 1.7 μm, maintained at 40° C.; Mobile Phase: Eluent B (MeCN/water 95:5+0.05% HCOOH) in Eluent A (water/MeCN 95:5+0.05% HCOOH) from 1% to 99.9% within 1.5 min. Flow rate: 1 mL/min. Wavelength: 210-400 nm DAD. UPLC+Waters™ PDA+Waters™ QDA.

Method 2: Acquity CSH C18 column 50 mm×2.1 mm 1.7 μm, maintained at 40° C.; Mobile Phase: Eluent B (MeCN/water 95:5+0.05% HCOOH) in Eluent A (water/MeCN 95:5+0.05% HCOOH) from 1% to 99.9% within 3.5 min. Flow rate: 1 mL/min. Wavelength: 210-400 nm DAD. UPLC+Waters™ PDA+Waters™ QDA.

Method 3: Waters™ Acquity QSM, Acquity UPLC CSH $C_{18}$ column 50 mm×2.1 mm 1.7 μm, maintained at 50° C.; Mobile Phase: Eluent A ($HCOONH_4$ 0.025M pH 3), Eluent B (ACN+0.1% FA). Gradient mode: from 0 to 5.50 min. eluent B is increased from 20% to 80%, from 5.50 to 7.50 min. is kept at 80%, from 7.50 to 8 min. is decreased from 80% to 20%, and from 8 min. it is kept at 20% till the end at 10 min. Flow rate: 0.35 mL/min. Wavelength: 210-400 nm DAD. UPLC+Waters™ PDA+Xevo TQS MS instrument.

Method 4: Waters™ Acquity QSM, Kinetex C8 column 100 mm×2.1 mm 1.7 μm, maintained at 55° C.; Mobile Phase: Eluent A ($HCOONH_4$ 0.025M pH 3), Eluent B (ACN+0.1% FA). Gradient mode: from 0 to 3 min. eluent B is increased from 1% to 30%, from 3 to 6.50 min. is increased from 30% to 50%, from 6.50 to 7.50 min. is increased from 50% to 80%, from 7.50 to 8 min is kept at 80%, from 8 to 8.10 min. is decreased from 80% to 1% and from 8.10 it is kept at 1% till the end at 10 min. Flow rate: 0.5 mL/min. Wavelength: 210-400 nm PAD. UPLC+Waters™ PDA+Xevo TQS MS instrument.

Chiral Supercritical Fluid Chromatography (SFC) Separation Protocol

The diastereomeric separation of compounds was achieved by Supercritical Fluid Chromatography (SFC) using a Gilson Preparative LC system.

Alternatively, the diastereomeric separation of compounds was achieved by Supercritical Fluid Chromatography (SFC) using a Waters™ Thar Prep100 preparative SFC system (P200 $CO_2$ pump, 2545 modifier pump, 2998 UV/VIS detector, 2767 liquid handler with Stacked Injection Module).

Analysis of two enantiomers was performed from reconstituted final samples.

Supercritical Fluid Chromatography—Mass Spectrometry Analytical Conditions

Method 5: SFC-MS was performed on a Gilson Preparative LC system (Gilson Pump—333; Gilson 151; Gilson Valvemate 6 position) using a Reprosil AMS (20 mm×250 mm, 5 μm) column with an isocratic run (20:80 MeOH:$CO_2$ (0.2% v/v $NH_3$), Flow Rate 50 mL/min, BPR 100 BarG, Detector Wavelength 210 nm, Injection Volume 1500 μL (213 mg), 40° C. column temperature.

Method 6: SFC-MS was performed on a Gilson Preparative LC system using a AMS (4.6 mm×250 mm, 5 μm) column with an isocratic run (20:80 MeOH:$CO_2$ (0.2% v/v $NH_3$), Detector Wavelength 210-400 nm, Injection Volume 1.0 Ul, BPR 125 BarG, at 4 mL/min, 40n° C. column temperature.

Method 7: Acquity BEH $C_{18}$ (2.1 mm×50 mm, 1.7 μm) maintained at 60° C.; Flow Rate 1.0 mL/min; Detector Wavelength 220-300 nm; Injection Volume 1.0 μL; Mobile Phase Eluent B MeCN Eluent A Water (0.1% v/v TFA) from 2% to 98% within 2 min. Flow rate: 1 mL/min. Wavelength: 220-300 nm.

Method 8: Acquity UPLC BEH Shield RP18 column, 100×2.1 mm, 1.72 μm (Plus guard cartridge), maintained at 40° C. Mobile phase: MeCN in water+10 nM ammonium bicarbonate from 5% to 95% within 5.6 min. Flow rate: 0.4 mL/min. Wavelength: 210-400 nm DAD. UPLC+Waters™ DAD+Waters™ SQD2, single quadrapole UPLC-MS Method 9: Acquity UPLC HSS C18 column, 100×2.1 mm, 1.8 μm (plus guard cartridge), maintained at 40° C. Mobile phase: MeCN (0.1% formic acid) in water (0.1% formic acid) from 5% to 95% within 5.6 min. Flow rate: 0.4 mL/min. Wavelength: 210-400 nm DAD. UPLC+Waters™ DAD+Waters™ SQD2, single quadrapole UPLC-MS Method 10: SFC-MS was performed on a Waters™/Thar SFC systems with Waters™ SQD using a LUX Cellulose-1 (20×250 mm, 5 μm) column with an isocratic run (50:50 isopropanol ($NH_4OH$ 0.1%):$CO_2$), flow rate 100 mL/min, 120 bar, 40° C. column temperature, DAD wavelength 265 nm.

Method 11: SFC-MS was performed on a Gilson Preparative LC system (Gilson Pump—333; Gilson 151; Gilson Valvemate 6 position) using a Chiralcel OD-H (30 mm×250 mm, 5 μm) column with an isocratic run (10:90 MeOH: $CO_2$), flow rate 180 mL/min, BPR 120 BarG, detector wavelength 237 nm, injection volume 1500 μL (135 mg), 40° C. column temperature.

Method 12: SFC-MS was performed on a Gilson Preparative LC system using a Lux C1 (4.6 mm×250 mm, 5 μm) column with a isocratic run (20:80 MeOH(0.2% v/v $NH_3$): $CO_2$), detector wavelength 210-400 nm, injection volume 1.0 mL, BPR 125 BarG, flow rate 4 mL/min, 40° C. column temperature.

Method 13: Waters™ Acquity CSH UPLC column, 2.1×50 mm, 1.7 μm maintained at 40° C. Mobile phase: MeCN (0.1% formic acid) in water (0.1% formic acid), from 3% to 99% within 1.5 min; flow rate: 1.0 ml/min; wavelength: 200-400 nm DAD. Acquity H-Class UPLC with PDA detector and QDa Mass Spectrometer.

Method 14: Acquity BEH UPLC column, 2.1×50 mm, 1.7 μm, maintained at 40° C. Mobile phase: MeCN (0.03% ammonia) in water (0.03% ammonia), from 8% to 97% within 1.5 min; flow rate: 0.8 ml/min; wavelength: 210-400 nm DAD. Acquity H-Class UPLC with PDA detector and QDa.

IR and VCD Spectroscopy Protocol

The stereochemistry of two enantiomers of tert-butyl 3-(2-methyl-5-((3-(trifluoromethyl)phenyl)carbamoyl)phenyl)pyrrolidine-1-carboxylate was determined using vibrational circular dichroism (VCD) spectroscopy. By comparing experimentally obtained VCD spectra to computationally simulated ones, the absolute configuration of the enantiomeric pair can be confidently assigned without prior knowledge of their relative stereochemistry. IR spectra are used to aid the assignment of the relative stereochemistry. The IR and VCD difference spectra further confirm the assignment of two enantiomers.

IR and VCD Spectroscopy

IR and VCD were recorded at BioTools Inc. on a ChiralIR w/DualPEM spectrometer at rt. The PEMs were optimized for 1400 $cm^{-1}$, and a resolution of 4 $cm^{-1}$ was used throughout. For all experiments, solutions with concentration of 7.1 mg in 100 μL of $CDCl_3$ were investigated using a 100 m path-length cell equipped with $BaF_2$ windows. The solution spectra were recorded for 24 hours per enantiomer. Because both enantiomers are available, baseline corrections were introduced using the spectrum of a virtual racemate.

Where the preparation of starting materials is not described, these are commercially available, known in the literature, or readily obtainable by those skilled in the art using standard procedures. All solvents were purchased from commercial sources and were used without additional purification. Flash chromatography (FCC) was performed on Biotage® Isolera™ (gradient A:B eluent A: $H_2O$:ACN: HCOOH 95:5:0.1 eluent B:$H_2O$:ACN:HCOOH 5:95:0.1), then SCX (NH) was utilized to obtained free base of the product, unless differently stated. When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions. All final compounds were obtained as a free base, unless stated otherwise.

General Procedures for the Preparation of Intermediates and Examples

Preparation of Intermediate 1: 4-(2-((5-bromopyridin-3-yl)oxy)ethyl)morpholine

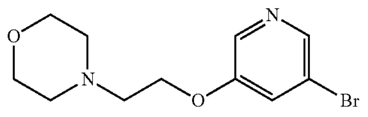 [SMILES: Brc1cncc(OCCN2CCOCC2)c1]

Sodium hydride mineral oil 60% (78 mg, 3.25 mmol) was added to a stirred solution of 2-morpholinoethan-1-ol (354 mg, 2.7 mmol) in ACN (7 ml) under an inert atmosphere. The reaction mixture was stirred for 1 h then 3-bromo-5-fluoropyridine (440 mg, 2.500 mmol) was added in one portion. The reaction mixture was stirred at rt until LC-MS indicated consumption of starting material. The reaction mixture was partitioned between water and DCM, and the aqueous phase was re-extracted with DCM (10 ml×2). The combined organic phases were filtered through a hydrophobic frit and then concentrated in vacuo to give title compound (546 mg, 1.90 mmol, 76% yield) that was used directly to the next step.

LC-MS (ESI): Method 1 $t_R$=0.16 min, m/z (M+1)=288.82

The following Intermediate 2 was prepared via aromatic nucleophilic substitution as described for Intermediate 1, applying the corresponding bromo derivative.

| Inter-mediate No | Structure<br>Analytical Data/Amount reagents/Purification | Product Amount (Yield) |
|---|---|---|
| 2 | 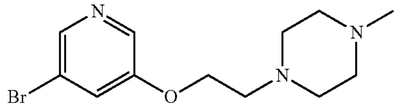 [SMILES: CN1CCN(CCOc2cncc(Br)c2)CC1]<br>LC-MS: Method 1 $t_R$ = 0.31 min; m/z (M + 1) = 301.86<br>3-bromo-5-fluoropyridine: 0.22 g (1 eq.) 2-(4-methylpiperazin-1-yl)ethan-1-ol: 0.217 g (1.2 eq.) | 315 mg (84%) |

Preparation of Intermediate 3: 5-bromo-N-(2-(dimethylamino)ethyl)nicotinamide

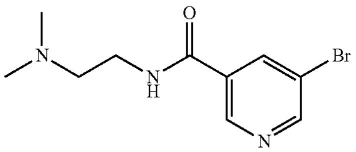

In a 20 mL vial 5-bromonicotinic acid (200 mg, 0.990 mmol), N1,N1-dimethylethane-1,2-diamine (131 mg, 1.485 mmol) and TBTU (477 mg, 1.485 mmol) were dissolved in DCM (2 ml), then DIPEA (0.345 ml, 1.980 mmol) was added in one portion. The solution was stirred overnight at rt. The crude was washed with sat sol $NH_4Cl$ (1×10 ml), sat sol $NaHCO_3$ (1×10 ml) and brine (1×15 mL). The organic layer was dried over $MgSO_4$ and desiccated under reduced pressure. The crude was purified by reverse phase FCC. The relevant fractions were combined and loaded onto an Isolute SCX-2 cartridge, washed with MeOH and the product was eluted with 2N methanolic ammonia. The residue was concentrated in vacuo to afford title compound (60 mg, 0.220 mmol, 22.27% yield).

LC-MS (ESI): Method 1 $t_R$=0.21 min, m/z (M+1)=273.78 The following Intermediate 4 and Intermediate 22 were prepared via amide coupling as described for Intermediate 3, applying the corresponding bromo derivative.

| Inter-mediate No | Structure<br>Analytical Data | Product Amount (Yield) |
|---|---|---|
| 4 | 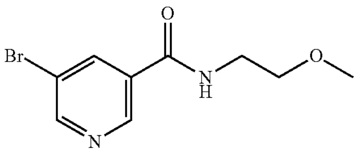<br>LC-MS: method 1 $t_R$ = 0.56 min; m/z (M + 1) = 260.79<br>5-bromonicotinic acid: 0.20 g (1 eq.) 2-methoxyethylamine: 0.089 g (1.2 eq.) | 150 mg (58%) |
| 22 | 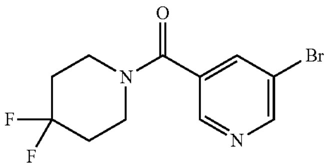 [SMILES: O=C(c1cncc(Br)c1)N1CCC(F)(F)CC1]<br>LC-MS: method 1 $t_R$ = 0.79 min; m/z (M + 1) = 360.82<br>5-bromonicotinic acid: 0.20 g (1 eq.) 4,4-difluoropiperidine: 0.144 g (1.2 eq.) | 150 mg (50%) |

Preparation of Intermediate 5: 4-(5-bromopyridin-3-yl)morpholine

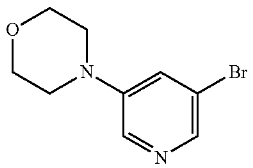 [SMILES: Brc1cncc(N2CCOCC2)c1]

A 40-mL round-bottom flask was charged with 3-bromo-5-fluoropyridine (300 mg, 1.705 mmol) in DMSO (2 mL), morpholine (220 mg, 2.56 mmol), and $K_2CO_3$ (704 mg, 5.09 mmol) under nitrogen. The resulting solution was stirred overnight at 80° C. and quenched with water (10 mL). The resulting solution was extracted with EtOAc (3×10 mL) and the organic layers were combined, washed with brine (2×10 mL), dried over sodium sulfate, filtered and concentrated under reduced pressure. The residue was purified by FCC eluting with EtOAc in heptane 0-5000 to provide title compound (170 mg, 0.699 mmol, 41% yield).

LC-MS (ESI, m/z): method 1 $t_R$=0.66 min m/z (M+1)=245.05

The following Intermediates 6, 23-27 and 29 were prepared via aromatic nucleophilic substitution as described for Intermediate 5, applying the corresponding bromo derivative.

| Intermediate No | Structure<br>Analytical Data | Product Amount (Yield) |
|---|---|---|
| 6 | 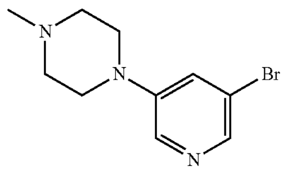<br>LCMS (ESI): Method 1 $t_R$ = 0.16 min; m/z (M + 2) = 258.05<br>3-bromo-5-fluoro pyridine: 0.30 g (1 eq.) 1-methyl-piperazine: 0.254 g (1.5 eq.) | 262 mg (60%) |
| 23 | 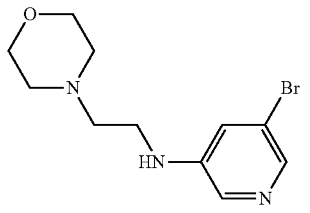 [SMILES: Brc1cncc(NCCN2CCOCC2)c1]<br>LCMS (ESI): Method 1 $t_R$ = 0.19 min; m/z (M + 1) = 288.10<br>3-bromo-5-fluoro pyridine: 0.10 g (1 eq.) 2-morpholinoethan-1-amine: 0.081 g (1.1 eq.) | 133 mg (82%) |
| 24 | 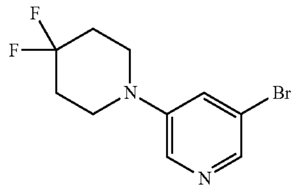 [SMILES: FC1(F)CCN(c2cncc(Br)c2)CC1]<br>LCMS (ESI): Method 1 $t_R$ = 0.98 min; m/z (M + 1) = 278.8<br>3-bromo-5-fluoro pyridine: 0.30 g (1 eq.) 4,4-difluoropiperidine: 0.248 gr (1.2 eq.) | 194 mg (41%) |
| 25 | 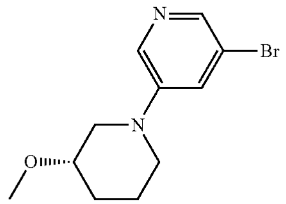<br>LCMS (ESI): Method 1 $t_R$ = 0.82 min; m/z (M + 2) = 273.1<br>3-bromo-5-fluoro pyridine: 0.30 g (1 eq.) (S)-3-methoxy-piperidine: 0.234 g (1.2 eq.) | 171 mg (37%) |
| 26 | 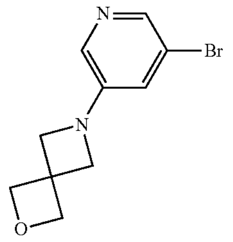 [SMILES: Brc1cncc(N2CC3(COC3)C2)c1]<br>LCMS (ESI): Method 1 $t_R$ = 0.62 min; m/z (M + 2) = 257.1<br>3-bromo-5-fluoro pyridine: 0.116 g (1 eq.)<br>2-oxa-6-azaspiro[3.3]heptane oxalate: 0.125 g (1 eq.) | 53 mg (31%) |

-continued

| Intermediate No | Structure / Analytical Data | Product Amount (Yield) |
|---|---|---|
| 27 | 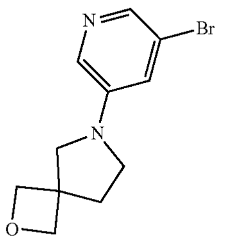 [SMILES: Brc1cncc(N2CCC3(COC3)C2)c1] LCMS (ESI): Method 1 $t_R$ = 0.61 min; m/z (M + 1) = 270.9 3-bromo-5-fluoro pyridine: 0.150 g (1 eq.) 2-oxa-6-azaspiro[3.4]octane hemioxalate | 59 mg (56%) |
| 29 | 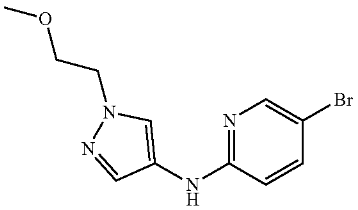 [SMILES: COCCn1cc(Nc2ccc(Br)cn2)cn1] LCMS (ESI): Method 1 $t_R$ = 0.73 min; m/z (M + 1) = 298.08 5-bromo-2-fluoropyridine: 0.2 g (1 eq.) 1-(2-methoxyethyl)pyrazol-4-amine: 0.16 (1 eq.) | 55 mg (16%) |

Preparation of Intermediate 7: 4-((5-bromopyridin-3-yl)methyl)morpholine

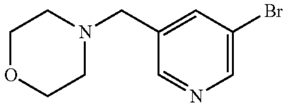 [SMILES: Brc1cncc(CN2CCOCC2)c1]

To a solution of the 5-bromonicotinaldehyde (300 mg, 1.613 mmol) in a mixture of DCM (3 ml) and DMIF (1 ml) was added morpholine (155 mg, 1.774 mmol), triisopropoxytitanium (IV) chloride (841 mg, 3.23 mmol) and AcOH (291 mg, 4.84 mmol). The reaction mixture was stirred at RT for 1 h. STAB (684 mg, 3.23 mmol) was added and the reaction mixture was stirred at RT until LC-MS indicated consumption of starting material. The reaction mixture was partitioned between DCM and saturated $NaHCO_3$ (aq) and the mixture filtered through a bed of Celite. The aqueous phase was extracted with 2×DCM and the combined organic phases were washed with saturated aqueous NaCl (aq), passed through a hydrophobic frit and concentrated in vacuo to afford title compound (92 mg, 0.358 mmol, 22.18% yield).

LC-MS (ESI, m/z): method1 $t_R$=0.16 min, m/z (M+1)=258.80

Preparation of Intermediate 28: N-(5-bromopyridin-3-yl)acetamide

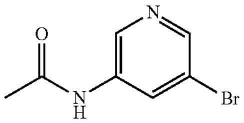

To a solution of 5-bromopyridin-3-amine (1 g, 5.78 mmol) in DCM (30 ml) acetic anhydride (1.745 ml, 18.50 mmol) was added, followed by DIPEA (2.73 ml, 15.61 mmol). Solution was stirred at rt overnight. Solution was diluted with $NaHCO_3$ saturated solution and extracted with DCM. Organic layer was dried over $MgSO_4$ and under reduced pressure. The crude was purified on a silica gel FCC (EtOAc in heptane 0-80%) to provide title compound (1.1 g, 5.12 mmol, 88%).

LC-MS (ESI, m/z): method 1 $t_R$=0.56 min, m/z (M+1)=216.83

Preparation of Intermediate 30: tert-butyl (5-bromopyrimidin-2-yl)(1-methyl-1H-pyrazol-4-yl)carbamate

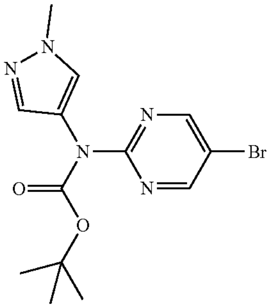 [SMILES: Cn1cc(N(C(=O)OC(C)(C)C)c2ncc(Br)cn2)cn1]

5-bromo-N-(1-methyl-1H-pyrazol-4-yl)pyrimidin-2-amine (315 mg, 1.24 mmol) was dissolved in DCM (3 ml) and then a solution of Boc-anhydride (0.576 ml, 2.48 mmol), TEA (0.518 ml, 3.72 mmol) and DMAP (7.57 mg, 0.062 mmol) was added. The solution was stirred at rt overnight. It was diluted with DCM (6 mL) and washed with water. Purification was performed on FCC (EtOAc in heptane 0-60%). Appropriate fractions were combined and evaporated under vacuum to give the desired compound (333 mg, 0.940 mmol, 76% yield).

LC-MS (ESI, m/z): method 1 $t_R$=0.87 min, m/z (M+1)=355.87

The following intermediates were prepared as described for Intermediate 30, applying the corresponding bromo derivative.

| Intermediate No | Structure<br>Analytical Data | Product Amount (Yield) |
|---|---|---|
| 31 | 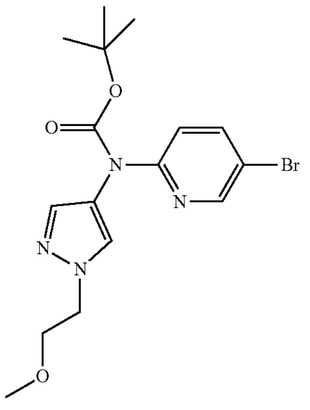 [SMILES: COCCn1cc(N(C(=O)OC(C)(C)C)c2ccc(Br)cn2)cn1]<br>LCMS (ESI): Method 1 $t_R$ = 1.02 min; m/z (M + 1) = 398.95<br>Intermediate 29: 0.055 g (1 eq.) Boc-anhydride: 0.081 g (2 eq.) | 65 mg (88%) |
| 32 | 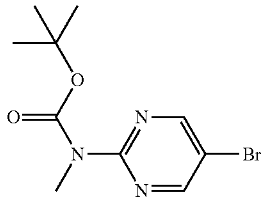 [SMILES: CN(C(=O)OC(C)(C)C)c1ncc(Br)cn1]<br>LCMS (ESI): Method 1 $t_R$ = 1.5 min; m/z (M + 1) = 288.14<br>5-bromo-N-methylpyrimidin-2-amine: 0.3 g (1 eq.) Boc-anhydride: 0.522 g (1.5 eq.) | 450 mg (98%) |

Preparation of Intermediate 33: 3-(pyrrolidin-1-ylmethyl)-5-(trifluoromethyl) aniline hydrochloride

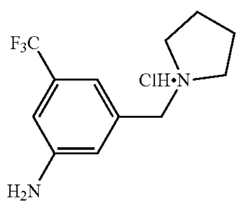

Step 1; 3-(trifluoromethyl)-5-vinyl-aniline (Intermediate 34)

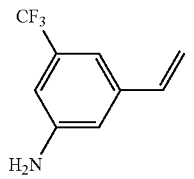

A mixture of 3-amino-5-bromobenzotrifluoride (2.50 g, 10.4 mmol), vinylboronic acid pinacol ester (2.10 mL, 12.5 mmol), XPhos Pd G3 (441 mg, 0.521 mmol), XPhos (497 mg, 1.04 mmol) and $K_3PO_4$ (5527 mg, 26.0 mmol) was suspended in 1,4-dioxane (45 mL) and water (5 mL). The reaction mixture was sparged with argon for 15 min, and then stirred at 80° C. for 1.5 h. The reaction mixture was left to reach rt and partitioned between water and EtOAc. The organic phase was washed with saturated NaCl (aq), dried ($MgSO_4$) and concentrated. The residue was purified by FCC on silica gel (0-30% EtOAc in cyclohexane) to give the desired compound (1.54 g, 79%).

LC-MS (ESI, m/z): method 13 $t_R$=1.45 min, m/z (M+1)=188

$^1$H NMR (400 MHz, $CDCl_3$) δ 7.04 (s, 1H), 6.85 (s, 1H), 6.79 (s, 1H), 6.64 (dd, J=11.0, 17.5 Hz, 1H), 5.75 (d, J=17.5 Hz, 1H), 5.30 (d, J=11.0 Hz, 1H), 3.86 (br s, 2H)

Step 2; tert-butyl N-[3-(trifluoromethyl)-5-vinyl-phenyl]carbamate (Intermediate 35)

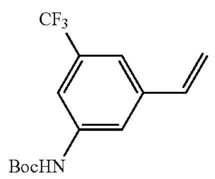 [SMILES: C=Cc1cc(NC(=O)OC(C)(C)C)cc(C(F)(F)F)c1]

To a mixture of Intermediate 34 (500 mg, 2.67 mmol) and di-tert-butyl dicarbonate (0.77 mL, 3.34 mmol) toluene (5 mL) was added. The reaction mixture was stirred at 100° C. for 19 h then allowed to cool to RT and concentrated in vacuo. The residue was diluted with heptane and filtered, and partially concentrated, resulting in formation of a dense precipitate. The suspension was filtered under vacuum to afford title compound (488 mg, 64%).

LC-MS (ESI, m/z): method 14 $t_R$=1.76 min, m/z (M−1)=286

$^1$H NMR (400 MHz, $CDCl_3$) δ 7.59-7.54 (m, 2H), 7.32 (s, 1H), 6.69 (dd, J=11.0, 17.5 Hz, 1H), 6.56 (s, 1H), 5.81 (d, J=17.5 Hz, 1H), 5.35 (d, J=11.0 Hz, 1H), 1.53 (s, 9H)

Step 3; tert-butyl N-[3-formyl-5-(trifluoromethyl) phenyl]carbamate (Intermediate 36)

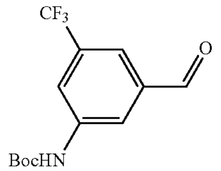 [SMILES: CC(C)(C)OC(=O)Nc1cc(C=O)cc(C(F)(F)F)c1]

A solution of Intermediate 35 (488 mg, 1.70 mmol) in DCM (20 mL) at −78° C. was sparged with ozone for 30 min at which point a light blue colour was observed. Dimethyl sulfide (0.62 mL, 8.49 mmol) was added, and the reaction mixture was allowed to warm to rt and stirred for 1 h. The reaction mixture was concentrated in vacuo and the residue was purified by column chromatography on silica gel (0-20% EtOAc in cyclohexane) to give title compound (278 mg, 57%).

LC-MS (ESI, m/z): method 14 $t_R$=1.60 min, m/z (M−1)=288

$^1$H NMR (400 MHz, $CDCl_3$) δ 10.02 (s, 1H), 8.06 (s, 1H), 7.98 (s, 1H), 7.80 (s, 1H), 6.76 (s, 1H), 1.54 (s, 9H)

Step 4; tert-butyl N-[3-(pyrrolidin-1-ylmethyl)-5-(trifluoromethyl) phenyl]carbamate (Intermediate 37)

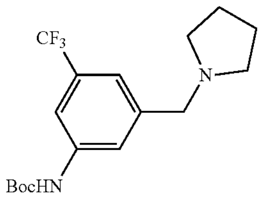 [SMILES: CC(C)(C)OC(=O)Nc1cc(CN2CCCC2)cc(C(F)(F)F)c1]

To a solution of Intermediate 36 (140 mg, 0.484 mmol) in DCM (3.5 mL) pyrrolidine (440 μL, 0.532 mmol), acetic acid (83 μL, 1.45 mmol) and titanium(IV) isopropoxide (290 μL, 0.968 mmol) were added. The reaction mixture was stirred at rt for 1 h. Sodium triacetoxyborohydride (205 mg, 0.968 mmol) was added and the reaction mixture was stirred at rt for a further 1.5 h. The reaction mixture was partitioned between saturated $NaHCO_{3\ (aq)}$ and EtOAc. The organic phase was washed with water, saturated $NaCl_{(aq)}$, filtered through a hydrophobic frit and concentrated in vacuo to afford title compound which was used in the next step without further purification.

LC-MS (ESI, m/z): method 14 $t_R$=1.75 min, m/z (M+1)=345 $^1$H NMR (400 MHz, $CDCl_3$) δ 7.65 (s, 1H), 7.44 (s, 1H), 7.27 (s, 1H), 6.58 (s, 1H), 3.63 (s, 2H), 2.55-2.50 (m, 4H), 1.81-1.77 (m, 4H), 1.52 (s, 9H)

Step 5; 3-(pyrrolidin-1-ylmethyl)-5-(trifluoromethyl)aniline (Intermediate 33)

To a solution of Intermediate 37 (186 mg, 0.540 mmol) in MeOH (3.00 mL) 4 M HCl in dioxane (0.41 mL, 1.62 mmol)

was added. The reaction mixture was stirred at rt overnight. The reaction mixture was concentrated in vacuo to give the HCl salt of title compound (140 mg, 90%).

LC-MS (ESI, m/z): method 14 $t_R$=1.39 min, m/z (M+1)=245

$^1$H NMR (400 MHz, DMSO-d6) δ 10.64 (s, 1H), 7.12 (s, 1H), 6.98 (s, 1H), 6.96 (s, 1H), 4.27 (d, J=6.0 Hz, 2H), 3.37-3.31 (m, 2H), 3.07-2.98 (m, 2H), 2.03-1.96 (m, 2H), 1.91-1.86 (m, 2H)

Example 5: preparation of 4-methyl-3-(1-(5-(2-morpholinoethoxy)pyridin-3-yl)pyrrolidin-3-yl)-N-(3-(trifluoromethyl)phenyl)benzamide

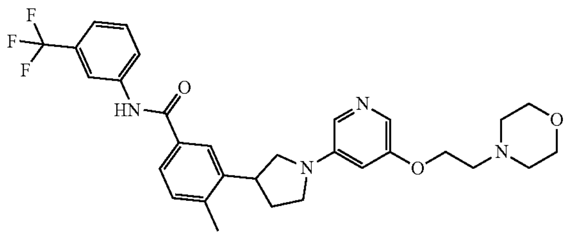 [SMILES: Cc1ccc(C(=O)Nc2cccc(C(F)(F)F)c2)cc1C1CCN(c2cncc(OCCN3CCOCC3)c2)C1]

Example 5

Step 1; 3-iodo-4-methylbenzoyl chloride (Intermediate 8)

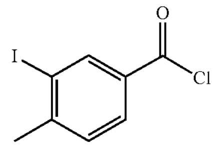

3-iodo-4-methylbenzoic acid (14.35 g, 54.8 mmol) was dissolved in DCM (100 ml) under argon atmosphere. DMF (0.085 ml) was added followed by dropwise addition of oxalyl chloride (6.95 ml, 82 mmol) at 0° C. The reaction mixture was allowed to warm up to rt and stirred under argon atmosphere for 2 h. Progress of the reaction was monitored by LC-MS (sample was quenched with MeOH) with full conversion after 2 h. The solvent was evaporated and the crude was used in next step without further purification.

Step 2; 3-iodo-4-methyl-N-(3-(trifluoromethyl)phenyl)benzamide (Intermediate 9)

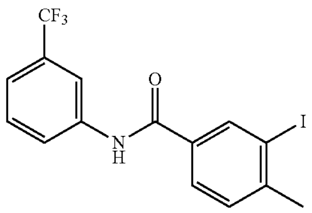 [SMILES: Cc1ccc(C(=O)Nc2cccc(C(F)(F)F)c2)cc1I]

Intermediate 8 (15.36 g, 54.8 mmol) was dissolved in THE (50 ml) and this solution was added to solution of 3-(trifluoromethyl)aniline (6.84 ml, 54.8 mmol), 4-dimethylamino pyridine (1.338 g, 10.95 mmol), N-ethyl-N-isopropylpropan-2-amine (11.45 ml, 65.7 mmol) in THF (50 ml). The reaction mixture was stirred at RT overnight. The mixture was concentrated under vacuum. The crude material was dissolved in water and extracted with DCM (x3). All the combined organic layers were dried over $Na_2SO_4$, filtered and concentrated. The crude material was used into the next step without other purification (100%, 54.8 mmol).

$^1$H NMR (300 MHz, Chloroform-d) δ 8.29 (d, J=1.9 Hz, 1H), 8.11 (s, 1H), 7.94 (d, J=1.9 Hz, 1H), 7.87 (dt, J=8.1, 1.7 Hz, 1H), 7.75 (dd, J=7.9, 1.9 Hz, 1H), 7.47 (t, J=7.9 Hz, 1H), 7.40 (d, J=7.7 Hz, 1H), 7.32 (d, J=7.9 Hz, 1H), 2.48 (s, 3H).

Step 3; 4-methyl-N-(3-(trifluoromethyl)phenyl)-3-vinylbenzamide (Intermediate 10)

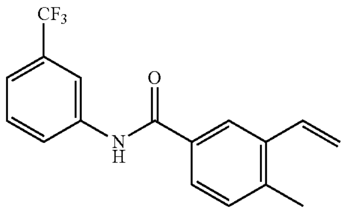 [SMILES: C=Cc1cc(C(=O)Nc2cccc(C(F)(F)F)c2)ccc1C]

In an oven dried 400 ml reactor Intermediate 9 (15 g, 37.0 mmol), potassium trifluoro(vinyl)borate (5.95 g, 44.4 mmol), $K_2CO_3$ (10.23 g, 74.0 mmol) were placed and 1,4-dioxane (150 ml) was added via syringe under argon atmosphere. Solution was filled with argon (10 min), next Pd(dppf)$Cl_2$ (0.361 g, 0.494 mmol) was added. The tube was sealed and heated at 110° C. over 18 h. The reaction mixture was filtered over a celite pad and desiccated under reduced pressure, the residual was dissolved in 200 mL of AcOEt and was washed with $NH_4Cl$ (1×100 ml), $NaHCO_3$ (1×100 mL) and brine (1×150 mL). The organic layers were dried over $MgSO_4$, filtered and the solvent was evaporated under reduced pressure. The crude was purified via FCC (gradient from 100:0 to 40:60 in 10 CV eluent A: n-Heptane eluent B: AcOEt), the appropriate fraction were collected and desiccated to afford title compound (8 g, 26.2 mmol, 71%).

$^1$H NMR (300 MHz, DMSO-d6) δ 8.03 (d, J=1.8 Hz, 1H), 7.76 (dd, J=7.9, 1.9 Hz, 1H), 7.33 (dt, J=7.9, 0.7 Hz, 1H), 6.98 (dd, J=17.5, 11.0 Hz, 1H), 5.76 (dd, J=17.5, 1.2 Hz, 1H), 5.41 (dd, J=11.0, 1.2 Hz, 1H), 3.84 (s, 3H), 2.37 (s, 3H).

Step 4; 3-(1-benzylpyrrolidin-3-yl)-4-methyl-N-(3-(trifluoromethyl)phenyl) benzamide (Intermediate 11)

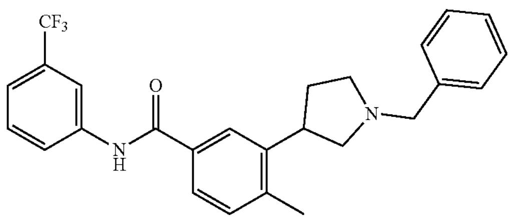 [SMILES: Cc1ccc(C(=O)Nc2cccc(C(F)(F)F)c2)cc1C1CCN(Cc2ccccc2)C1]

A mixture of Intermediate 10 (14.00 g, 45.9 mmol), N-benzyl-1-methoxy-N-((trimethylsilyl)methyl) methanamine (10.89 g, 45.9 mmol) and then dioxane (100 ml) containing 0.01% of TFA (0.035 ml, 0.459 mmol) was placed in a closed vessel and heated at 120° C. for 3 h. The solvent was removed under vacuum. The reaction mixture was diluted with AcOEt and water. The organic layer was separated and the aqueous layer was extracted with AcOEt (2×). The combined organic layer was washed with brine, dried with $MgSO_4$, and concentrated to afford the crude product. The crude product was used directly to the next step or purified by direct phase FCC (heptane 100% to heptane/AcOEt=6:4) leading to title product (7 g, 16 mmol, 35% yield).

Step 5; 4-methyl-3-(pyrrolidin-3-yl)-N-(3-(trifluoromethyl)phenyl) benzamide (Intermediate 12)

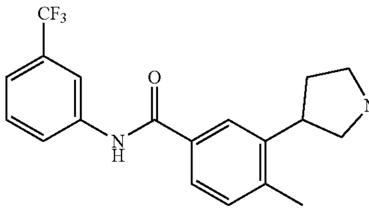

A Parr reactor was purged with nitrogen, and charged with palladium/C 5R39 JM 5% (4 g, 0.940 mmol, 2.5 wt %). The system was once more purged with nitrogen and placed under vacuum. A solution of Intermediate 11 (10 g, 22.81 mmol) in MeOH (300 ml) was then charged and the system was purged with nitrogen once more. The solution was then placed under an atmosphere of hydrogen (7 bar), warmed to 40±° C. and stirred for 2 h. The reaction mixture and reactor rinses were filtered through celite and concentrated to afford a crude that was used without further purification in the next step.

$^1$H NMR (400 MHz, DMSO-d6) δ ppm 10.55 (s, 1H), 8.27 (s, 1H), 8.10 (br d, J=8.11 Hz, 1H), 7.99 (s, 1H), 7.80 (dd, J=7.89, 1.75 Hz, 1H), 7.60 (t, J=8.00 Hz, 1H), 7.45 (d, J=7.89 Hz, 1H), 7.37 (d, J=8.11 Hz, 1H), 3.61-3.71 (m, 1H), 3.55 (dd, J=11.07, 8.00 Hz, 1H), 3.37-3.44 (m, 1H), 3.19-3.26 (m, 1H), 3.13 (dd, J=10.96, 9.21 Hz, 1H), 2.41 (s, 3H), 2.29-2.38 (m, 1H), 1.92-2.05 (m, 1H).

Step 6; 4-methyl-3-(1-(5-(2-morpholinoethoxy)pyridin-3-yl)pyrrolidin-3-yl)-N-(3-(trifluoromethyl)phenyl)benzamide (Example 5)

20 mL MW vial, equipped with a magnetic stir bar and fitted with a seal cap, was charged with a mixture of 4-(2-((5-bromopyridin-3-yl)oxy)ethyl)morpholine (124 mg, 0.431 mmol), Intermediate 12 (100 mg, 0.287 mmol), $CsCO_3$ (281 mg, 0.861 mmol), RuPhos (26.8 mg, 0.057 mmol), $Pd(dppf)Cl_2$ (10.50 mg, 0.014 mmol). The vessel vas evacuated and backfilled with Ar, then DMA (4 ml) was added via syringe. The solution was heated at 120° C. and stirred for 2 h. The reaction mixture was filtered and the filtrated was washes with EtOH, the solution was reduced under vacuo and the residual crude was purified by Reverse phase FCC (gradient A:B from 100:0 to 60:40 with 10 CV, eluent A: $H_2O$:ACN:HCOOH 95:5:0.1 eluent B:$H_2O$:ACN:HCOOH 5:95:0.1). The relevant fractions were combined and loaded onto an Isolute SCX-2 cartridge, washed with MeOH and the product was eluted with 2N methanolic ammonia. The residue was concentrated in vacuo to afford title compound (11 mg, 0.020 mmol, 6.91% yield).

$^1$H NMR (acetone, 400 MHz) δ 8.25 (s, 1H), 8.12 (s, 1H), 8.0-8.0 (m, 2H), 7.7-7.9 (m, 1H), 7.63 (dd, J=2.1, 10.0 Hz, 2H), 7.55 (t, J=8.0 Hz, 1H), 7.41 (d, J=7.7 Hz, 1H), 7.36 (d, J=7.9 Hz, 1H), 6.51 (t, J=2.1 Hz, 1H), 4.16 (t, J=5.8 Hz, 2H), 3.8-3.9 (m, 1H), 3.77 (t, J=8.4 Hz, 1H), 3.5-3.6 (m, 6H), 3.4-3.5 (m,1H), 3.37 (t, J=8.7 Hz, 1H), 2.72 (t, J=5.7 Hz, 3H), 2.5-2.4 (m, 1H), 2.3-2.2 (m, 1H), 2.23-2.50 (m, 6H).

LC-MS (ESI): method 4 $t_R$=5.36 min; m/z (M+1)=555.2;

The following compounds were prepared as described for Example 5, steps 1-6, applying the corresponding, commercially available bromo-intermediate in step 6; such procedures may involve minor variations, for example reaction temperature, reaction time, work-up conditions. In some cases, where modification involved catalysts, ligand (e.g. $Pd(dba)_2$/BINAP instead of $Pd(dppf)Cl_2$/RuPhos) or solvent, such changes were reported in the table.

| Example No | Structure<br>Analytical Data/Amount reagents/Purification | Product Amount (Yield) |
|---|---|---|
| 1 | 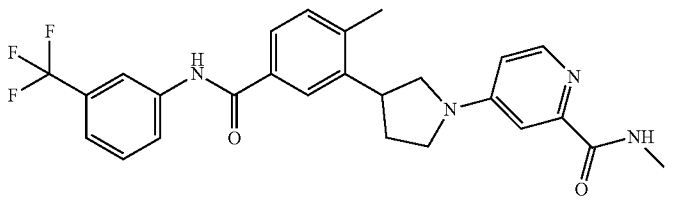 [SMILES: CNC(=O)c1cc(N2CCC(c3cc(C(=O)Nc4cccc(C(F)(F)F)c4)ccc3C)C2)ccn1]<br>LC-MS (ESI): Method 1 $t_R$ = 0.76 m/z (M + 1) = 483.05.4<br>$^1$H NMR (acetone, 400 MHz) δ 8.23 (br s, 1H), 8.10 (br d, J = 5.48 Hz, 1H), 7.97-8.06 (m, 2H), 7.77-7.84 (m, 1H), 7.50-7.60 (m, 1H), 7.33-7.44 (m, 2H), 7.27 (s, 1H), 6.60-6.61 (m, 1H), 3.8-3.9 (m, 2H), 3.6-3.7 (m, 1H), 3.49-3.58 (m, 1H), 3.45 (br t, J = 8.55 Hz, 1H), 2.91 (s, 5H), 2.21-2.48 (m, 4H)<br>4-bromo-N-methylpicolinamide: 63 mg (1.1 eq.) Intermediate 12: 85 mg (1 eq.); Pd(dba)2: 14 mg BINAP: 30.4 mg Toluene: 5 ml; FCC, SCX | 11 mg (9%) |

-continued

| Example No | Structure Analytical Data/Amount reagents/Purification | Product Amount (Yield) |
|---|---|---|
| 2 | 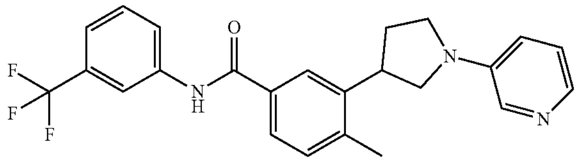 [SMILES: Cc1ccc(C(=O)Nc2cccc(C(F)(F)F)c2)cc1C1CCN(c2cccnc2)C1]<br>LC-MS (ESI): Method 1 $t_R$ = 0.78 m/z (M + 1) = 426.13<br>$^1$H NMR (ACN-d3, 400 MHz) δ 8.88 (br s, 1H), 8.14 (s, 1H), 8.03 (d, 1H, J = 2.8 Hz), 7.8-7.9 (m, 3H), 7.73 (dd, 1H, J = 1.9, 8.0 Hz), 7.54 (t, 1H, J = 8.0 Hz), 7.43 (d, 1H, J = 7.9 Hz), 7.37 (d, 1H, J = 7.9 Hz), 7.16 (dd, 1H, J = 4.6, 8.6 Hz), 6.95 (ddd, 1H, J = 1.3, 3.0, 8.4 Hz), 3.86 (dd, 1H, J = 7.2, 9.0 Hz), 3.7-3.8 (m, 1H), 3.4-3.6 (m, 3H), 2.49 (s, 3H), 2.4-2.5 (m, 1H), 2.2-2.3 (m, 1H)<br>3-bromopyridine: 25 mg (1.1 eq.) Intermediate 12: 55 mg (1 eq.); $Pd(dba)_2$: 7.2 mg RuPhos: 14.7 mg Toluene: 5 ml; FCC, SCX | 12 mg (18%) |
| 3 | 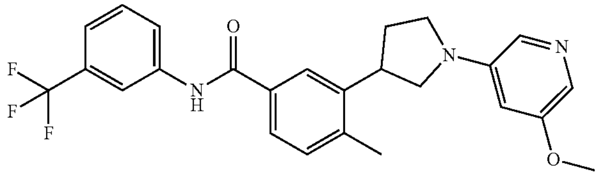 [SMILES: COc1cncc(N2CCC(c3cc(C(=O)Nc4cccc(C(F)(F)F)c4)ccc3C)C2)c1]<br>LC-MS (ESI): method 1 $t_R$ = 0.88 min; m/z (M + 1) = 456.27<br>$^1$H NMR (acetone, 400 MHz) δ 8.26 (s, 1H), 8.11 (s, 1H), 8.0-8.1 (m, 2H), 7.83 (br d, J = 7.9 Hz, 1H), 7.5-7.7 (m, 3H), 7.42 (br d, J = 7.7 Hz, 1H), 7.37 (br d, J = 7.9 Hz, 1H), 6.50 (s, 1H), 3.84-3.92 (m, 1H), 3.82 (s, 3 H), 3.7-3.8 (m, 1H), 3.6-3.7 (m, 1H), 3.5-3.5 (m, 1H), 3.38 (t, J = 8.7 Hz, 1H), 2.52 (s, 3H), 2.4-2.5 (m, 1H), 2.2-2.4 (m, 1H).<br>3-bromo-5-methoxypyridine: 54 mg (1.1 eq.) Intermediate 12: 100 mg (1 eq.); RuPhos: 27 mg $Pd(dba)_2$: 13 mg DMA: 2 ml; FCC, SCX | 15 mg (12%) |
| 4 | 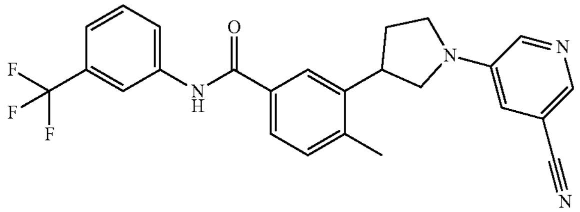 [SMILES: Cc1ccc(C(=O)Nc2cccc(C(F)(F)F)c2)cc1C1CCN(c2cncc(C#N)c2)C1]<br>LC-MS (ESI): method 1 $t_R$ = 1.29 min; m/z (M + 1) = 451.27<br>$^1$H NMR (acetone, 400 MHz) δ 9.75 (br s, 1H), 8.24 (br s, 2H), 8.12 (br s, 1H), 7.97-8.05 (m, 2H), 7.81 (br d, J = 7.89 Hz, 1H), 7.55 (br t, J = 7.89 Hz, 1H), 7.39-7.20 (m, 3H), 3.23-4.2 (m, 5H), 2.53 (s, 3H), 2.3-2.4 (m, 1H), 0.76-1.54 (m, 1H).<br>5-bromo nicotinonitrile: 63 mg (1.1 eq.) Intermediate 12: 120 mg (1 eq.) RuPhos: 32 mg $Pd(dba)_2$: 63 mg DMA: 2 ml; FCC, SCX | 30 mg (19%) |
| 6 | 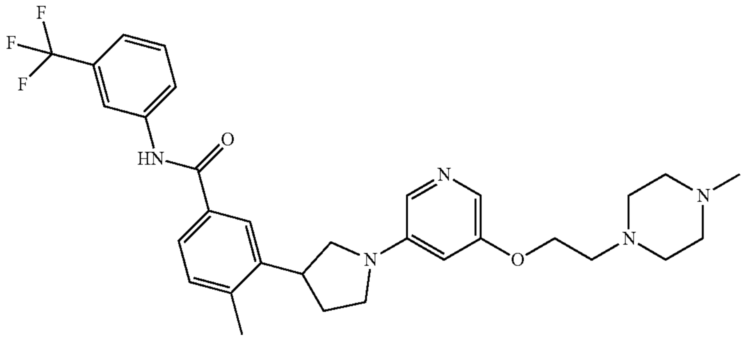 [SMILES: Cc1ccc(C(=O)Nc2cccc(C(F)(F)F)c2)cc1C1CCN(c2cncc(OCCN3CCN(C)CC3)c2)C1]<br>LC-MS (ESI): method 4 $t_R$ = 5.14 min; m/z (M + 1) = 568.28<br>$^1$H NMR (acetone, 400 MHz) δ 8.25 (s, 1H), 8.15 (s, 2H), 8.0-8.1 (m, 1H), 7.81 (dd, J = 1.5, 7.9 Hz, 1H), 7.62 (dd, J = 2.3, 10.0 Hz, 2H), 7.5-7.6 (m, 1H), 7.41 (d, J = 7.9 Hz, 1H), 7.3-7.4 (m, 1H), 6.52 (t, J = 2.1 Hz, 1H), 4.15 (t, J = 5.7 Hz, 2H), 3.86 (br d, J = 8.3 Hz, 1H), 3.76 (t, J = 8.4 Hz, 1H), 3.59 (br dd, J = 3.0, 8.4 Hz, 1H), 3.48 (br d, J = 7.2 Hz, 1H), 3.3-3.4 (m, 2H), 2.74 (t, J = 5.8 Hz, 3H), 2.58 (br s, 4H), 2.50 (s, | 13 mg (8%) |

-continued

| Example No | Structure<br>Analytical Data/Amount reagents/Purification | Product Amount (Yield) |
| --- | --- | --- |
| | 3H), 2.4-2.5 (m, 3H), 2.27 (br d, J = 9.6 Hz, 1H), 2.23 (s, 3H).<br>1-(2-((5-bromopyridin-3-yl)oxy)ethyl)-4-methylpiperazine: 95 mg (1.1 eq.) Intermediate 12: 100 mg (1 eq.); FCC, SCX | |
| 7 | 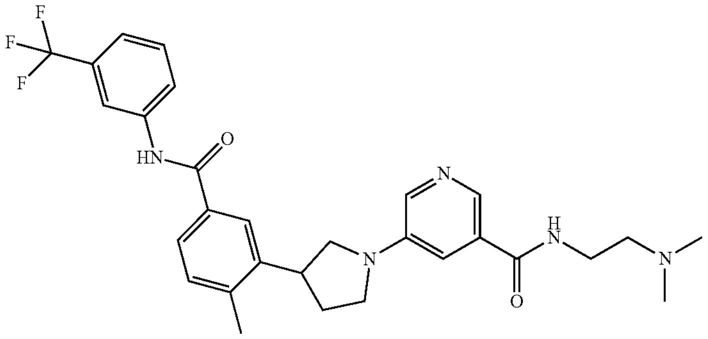 [SMILES: Cc1ccc(C(=O)Nc2cccc(C(F)(F)F)c2)cc1C1CCN(c2cncc(C(=O)NCCN(C)C)c2)C1]<br>LC-MS (ESI): method 4 $t_R$ = 5.45 min; m/z (M + 1) = 540.20<br>$^1$H NMR (MEOH-d4, 400 MHz) δ 8.22 (d, J = 1.8 Hz, 1H), 8.08 (s, 1H), 8.04 (d, J = 2.9 Hz, 1H), 7.8-7.9 (m, 2H), 7.73 (dd, J = 1.9, 7.8 Hz, 1H), 7.50 (t, J = 8.0 Hz, 2H), 7.3-7.5 (m, 2H), 3.8-3.9 (m, 2H), 3.63 (br dd, J = 3.4, 8.2 Hz, 1H), 3.5-3.6 (m, 5H), 2.5-2.6 (m, 2H), 2.50 (s, 3H), 2.46 (s, 1H), 2.2-2.3 (s, 8H)<br>5-bromo-N-(2-(dimethylamino)ethyl)nicotinamide: 39 mg (1.1 eq.) Intermediate 12: 50 mg (1 eq.); FCC, SCX | 15 mg (19%) |
| 8 | 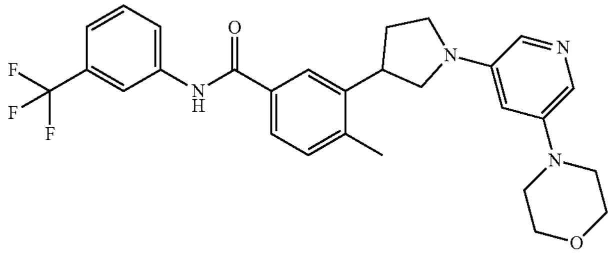 [SMILES: Cc1ccc(C(=O)Nc2cccc(C(F)(F)F)c2)cc1C1CCN(c2cncc(N3CCOCC3)c2)C1]<br>LC-MS (ESI): method 3 $t_R$ = 4.09 min; m/z (M + 1) = 511.30<br>$^1$H NMR (MEOH-d4, 400 MHz) δ 8.46 (bs, 1H), 8.10 (s, 1H), 7.8-7.9 (m, 2H), 7.74 (dd, J = 1.8, 7.9 Hz, 1H), 7.6-7.6 (m, 1H), 7.5-7.6 (m, 2H), 7.40 (d, J = 7.7 Hz, 1H), 7.35 (d, J = 7.9 Hz, 1H), 6.56 (s, 1H), 3.7-3.9 (m, 6H), 3.4-3.6 (m, 3H), 3.1-3.2 (m, 4H), 2.50 (s, 3H), 2.4-2.5 (m, 1H), 2.2-2.3 (m, 1H)<br>4-(5-bromo pyridin-3-yl)morpholine: 70 mg (1 eq.) Intermediate 12: 100 mg (1 eq.); FCC, SCX | 15 mg (16%) |
| 9 | 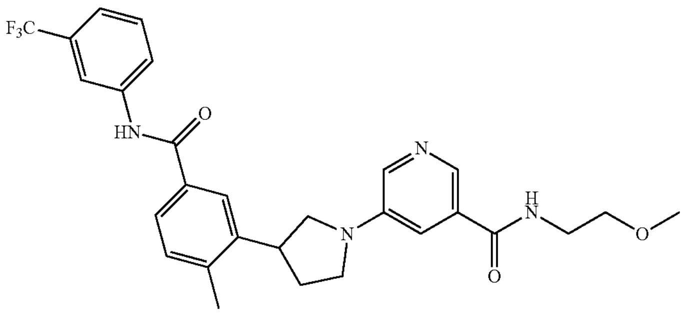 [SMILES: COCCNC(=O)c1cncc(N2CCC(c3cc(C(=O)Nc4cccc(C(F)(F)F)c4)ccc3C)C2)c1]<br>LC-MS (ESI): method 4 $t_R$ = 6.71 min; m/z (M + 1) = 527.20<br>$^1$H NMR (MEOH-d4, 400 MHz) δ 8.21 (s, 1H), 8.08 (s, 1H), 8.04 (d, J = 2.4 Hz, 1H), 7.8-7.9 (m, 2H), 7.7-7.8 (m, 1H), 7.50 (br t, J = 8.0 Hz, 1H), 7.3-7.4 (m, 3H), 3.40-3.94 (m, 9H), 3.35 (s, 3H), 2.42-2.57 (m, 4H), 2.26-2.29 (m, 1H)<br>5-bromo-N-(2-methoxyethyl)nicotinamide: 60 mg (1 eq.) Intermediate 12: 80 mg (1 eq.); FCC, SCX | 12 mg (10%) |

-continued

| Example No | Structure<br>Analytical Data/Amount reagents/Purification | Product Amount (Yield) |
|---|---|---|
| 10 | 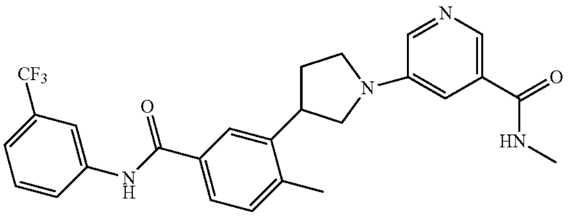 [SMILES: CNC(=O)c1cncc(N2CCC(c3cc(C(=O)Nc4cccc(C(F)(F)F)c4)ccc3C)C2)c1]<br>LC-MS (ESI): method 3 $t_R$ = 4.54 min; m/z (M + 1) = 483.17<br>$^1$H NMR (acetone, 400 MHz) δ 9.80 (br s, 1H), 8.34 (s, 1H), 8.26 (s, 1H), 8.0-8.1 (m, 3H), 7.83 (dd, J = 1.5, 7.9 Hz, 1H), 7.77 (br s, 1H), 7.56 (t, J = 8.0 Hz, 1H), 7.3-7.4 (m, 3H), 3.9-4.0 (m, 1H), 3.8-3.9 (m, 1H), 3.65 (dt, J = 3.1, 8.8 Hz, 1H), 3.4-3.6 (m, 2H), 2.89 (d, J = 4.6 Hz, 3H), 2.52 (s, 3H), 2.5-2.5 (m, 1H), 2.29 (br dd, J = 9.2, 12.1 Hz, 1H).<br>5-bromo-N-methylnicotinamide: 48 mg (1 eq.)Intermediate 12: 71 mg (1 eq.); FCC, SCX | 15 mg (15%) |
| 11 | 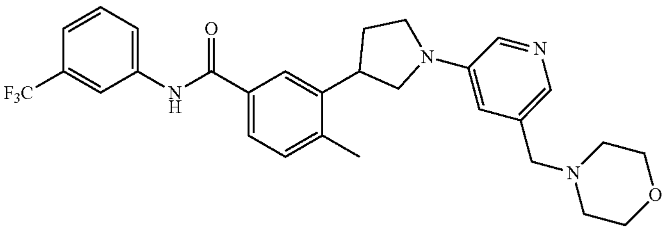 [SMILES: Cc1ccc(C(=O)Nc2cccc(C(F)(F)F)c2)cc1C1CCN(c2cncc(CN3CCOCC3)c2)C1]<br>LC-MS (ESI): method 4 $t_R$ = 5.72 min; m/z (M + 1) = 525.30<br>$^1$H NMR (MEOH-d4, 400 MHz) δ 8.30 (br s, 1H), 8.08 (s, 1H), 7.8-7.9 (m, 3H), 7.79 (s, 1H), 7.72 (dd, J = 1.8, 7.9 Hz 1H), 7.51 (t, J = 8.0 Hz, 1H), 7.3-7.4 (m, 2H), 7.08 (s, 1H), 3.7-3.9 (m, 2H), 3.6-3.7 (m, 4H), 3.59 (dt, J = 4.1, 8.6 Hzm 1H), 3.5-3.5 (m, 4H), 2.40-2.56 (m, 8H), 2.2-2.3 (m, 1H).<br>4-((5-bromopyridin-3-yl)methyl)morpholine: 59 mg (1 eq.)<br>Intermediate 12: 80 mg (1 eq.); FCC, SCX | 14 mg (12%) |
| 12 | 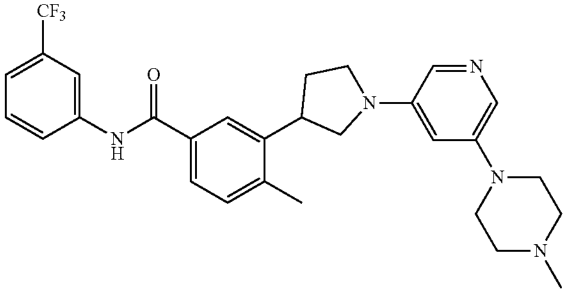 [SMILES: Cc1ccc(C(=O)Nc2cccc(C(F)(F)F)c2)cc1C1CCN(c2cncc(N3CCN(C)CC3)c2)C1]<br>LC-MS (ESI): method 3 $t_R$ = 4.83 min; m/z (M + 1) = 524<br>$^1$H NMR (acetone, 400 MHz) δ 9.81 (br s, 1H), 8.27 (s, 1H), 8.0-8.1 (m, 2H), 7.82 (dd, J = 1.8, 7.9 Hzm 1H), 7.68 (d, J = 2.4 Hz, 1H), 7.5-7.6 (m, 2H), 7.42 (d, J = 7.7 Hz, 1H), 7.37 (d, J = 7.9 Hz, 1H), 6.49 (t, J = 2.2 Hz, 1H), 3.8-3.9 (m, 1H), 3.77 (t, J = 8.4 Hz, 1H), 3.5-3.6 (m, 1H), 3.4-3.5 (m, 1H), 3.36 (t, J = 8.7 Hz, 1H), 3.21-3.30 (m, 4H), 2.54-2.61 (m, 4H), 2.51 (s, 3H), 2.4-2.5 (m, 1H), 2.29 (s, 3H), 2.2-2.3 (m, 1H)<br>1-(5-bromopyridin-3-yl)-4-methylpiperazine: 40 mg (1 eq.)<br>Intermediate 12: 54 mg (1 eq.); FCC, SCX | 19 mg (23%) |

-continued

| Example No | Structure<br>Analytical Data/Amount reagents/Purification | Product Amount (Yield) |
|---|---|---|
| 21 | 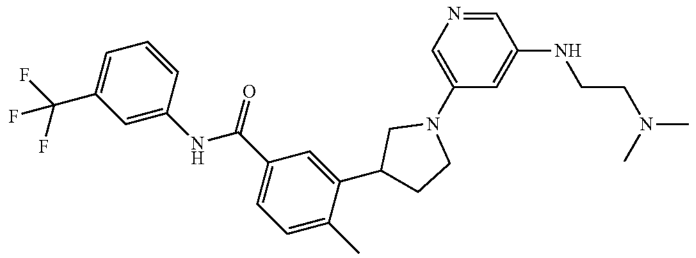 [SMILES: Cc1ccc(C(=O)Nc2cccc(C(F)(F)F)c2)cc1C1CCN(c2cncc(NCCN(C)C)c2)C1]<br>LC-MS (ESI): method 4 $t_R$ = 4.82 min; m/z (M + 1) = 512.2<br>$^1$H NMR (MeOH-d4, 400 MHz) δ 8.32 (br s, 2H), 8.10 (s, 1H), 7.8-7.9 (m, 2H), 7.73 (dd, 1H, J = 1.8, 7.9 Hz), 7.56 (s, 1H), 7.51 (t, 1H, J = 8.0 Hz), 7.3-7.4 (m, 4H), 6.40 (t, 1H, J = 2.1 Hz), 3.8-3.9 (m, 1H), 3.7-3.8 (m, 1H), 3.4-3.6 (m, 5H), 3.2-3.3 (m, 2H), 2.83 (s, 6H), 2.49 (s, 3H), 2.4-2.5 (m, 1H), 2.1-2.3 (m, 1H)<br>N1-(5-bromopyridin-3-yl)-N2,N2-dimethylethane-1,2-diamine: 56 mg (1 eq.)v Intermediate 12: 80 mg (1 eq.); FCC, SCX | 16 mg (14%) |
| 22 | 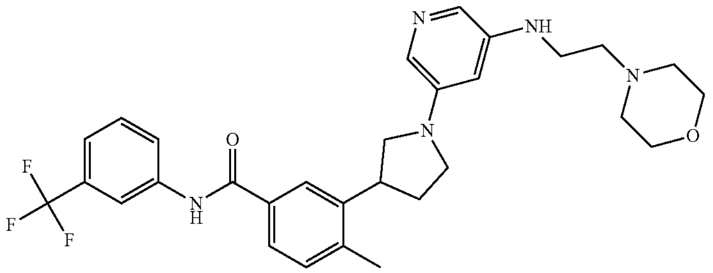 [SMILES: Cc1ccc(C(=O)Nc2cccc(C(F)(F)F)c2)cc1C1CCN(c2cncc(NCCN3CCOCC3)c2)C1]<br>LC-MS (ESI): method 1 $t_R$ = 0.6 min; m/z (M + 1) = 554.4<br>$^1$H NMR (MeOH-d4, 400 MHz) δ 8.33 (br s, 1H), 8.10 (s, 1H), 7.8-7.9 (m, 2H), 7.73 (dd, 1H, J = 1.8, 7.9 Hz), 7.51 (t, 1H, J = 8.0 Hz), 7.30-7.40 (m, 4H), 6.50 (s, 1H), 3.8-3.9 (m, 1H), 3.40-3.81 (m, 8H), 2.68 (t, 2H, J = 6.5 Hz), 2.5-2.6 (m, 4H), 2.49 (s, 3H), 2.4-2.5 (m, 1H), 2.23 (br dd, 1H, J = 8.3, 12.3 Hz)<br>Intermediate 23: 72 mg (1 eq.) Intermediate 12: 80 mg (1 eq.); FCC, SCX | 15 mg (12%) |
| 23 | 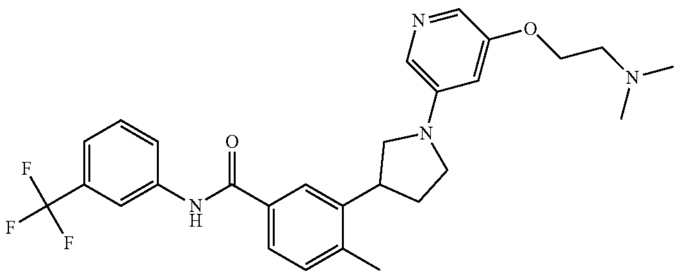 [SMILES: Cc1ccc(C(=O)Nc2cccc(C(F)(F)F)c2)cc1C1CCN(c2cncc(OCCN(C)C)c2)C1]<br>LC-MS (ESI): method 4 $t_R$ = 5.06 min; m/z (M + 1) = 513.2<br>$^1$H NMR (DMSO-d6, 400 MHz) δ 10.38 (s, 1H), 8.17 (s, 1H), 8.13 (s, 1H), 8.0-8.0 (m, 1H, J = 8.1 Hz), 7.89 (s, 1H), 7.7-7.8 (m, 1H, J = 7.9 Hz), 7.5-7.6 (m, 3H), 7.4-7.4 (m, 1H, J = 7.9 Hz), 7.3-7.4 (m, 1H, J = 8.1 Hz), 6.49 (s, 1H), 4.08 (t, 2H, J = 5.7 Hz), 3.6-3.8 (m, 3H), 3.51 (br d, 1H, J = 6.4 Hz), 3.3-3.4 (m, 1H), 2.67 (t, 2H, J = 5.7 Hz), 2.44 (s, 3H), 2.3-2.4 (m, 2H), 2.22 (s, 6H)<br>2-((5-bromopyridin-3-yl)oxy)-N,N-dimethylethan-1-amine: 56 mg (1 eq.) Intermediate 12: 80 mg (1 eq.); FCC, SCX | 45 mg (38%) |

-continued

| Example No | Structure Analytical Data/Amount reagents/Purification | Product Amount (Yield) |
|---|---|---|
| 24 | 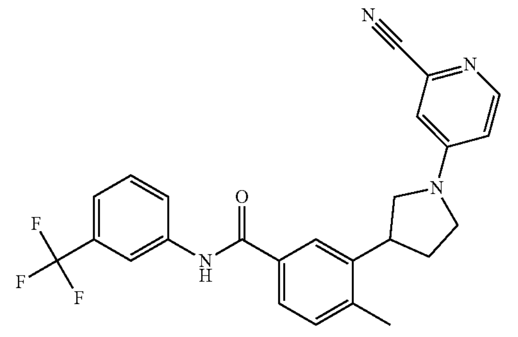 [SMILES: Cc1ccc(C(=O)Nc2cccc(C(F)(F)F)c2)cc1C1CCN(c2ccnc(C#N)c2)C1]<br>LC-MS (ESI): method 3 $t_R$ = 5.25 min; m/z (M + 1) = 451.3<br>$^1H$ NMR (MeOH-d4, 400 MHz) δ 8.12 (d, 1H, J = 6.1 Hz), 8.09 (s, 1H), 7.87-7.89 (m, 2H), 7.74 (dd, 1H, J = 1.5, 7.9 Hz), 7.51 (t, 1H, J = 8.0 Hz), 7.3-7.4 (m, 2H), 7.04 (d, 1H, J = 2.4 Hz), 6.73 (dd, 1H, J = 2.4, 6.1 Hz), 3.8-3.9 (m, 2H), 3.6-3.7 (m, 1H), 3.4-3.6 (m, 2H), 2.49 (s, 3H), 2.4-2.5 (m, 1H), 2.27 (br dd, 1H, J = 8.8, 12.3 Hz)<br>4-bromopicolinonitrile: 50 mg (1 eq.) Intermediate 12: 80 mg (1 eq.); FCC, SCX | 11 mg (10%) |

Example 13: preparation of 3-(1-(5-bromopyridin-3-yl)pyrrolidin-3-yl)-4-methyl-N-(3-(trifluoromethyl)phenyl)benzamide

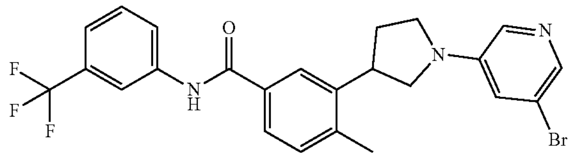 [SMILES: Cc1ccc(C(=O)Nc2cccc(C(F)(F)F)c2)cc1C1CCN(c2cncc(Br)c2)C1]

Step 1; 3-(1-(5-bromopyridin-3-yl)pyrrolidin-3-yl)-4-methyl-N-(3-(trifluoromethyl)phenyl)benzamide 3-bromo-5-fluoropyridine (672 mg, 3.82 mmol) and Intermediate 12 (133 mg, 0.382 mmol) were dissolved in DMSO (2 ml) and $Cs_2CO_3$ (249 mg, 0.764 mmol) was added in one portion. The mixture was stirred for 72 h at 80° C. The crude was diluted with 50 mL of brine and the solution was extracted with THF, the organic layers were desiccated over $MgSO_4$, filtrated under reduced pressure to obtain the crude that was purified via silica gel FCC (EtOAc in n-Heptane from 100:0 to 0:100) to give the title product (173 mg, 0.343 mmol, 90% yield).

$^1H$ NMR (acetone, 400 MHz) δ 9.73 (br s, 1H), 8.25 (s, 1H), 8.0-8.1 (m, 3H), 7.90 (s, 1H), 7.83 (dd, 1H, J=1.8, 7.9 Hz), 7.57 (t, 1H, J=8.0 Hz), 7.43 (d, 1H, J=7.5 Hz), 7.38 (d, 1H, J=7.9 Hz), 7.12 (t, 1H, J=2.2 Hz), 3.91 (br d, 1H, J=8.1 Hz), 3.8-3.9 (m, 1H), 3.6-3.7 (m, 1H), 3.5-3.6 (m, 1H), 3.42 (t, 1H, J=8.8 Hz), 2.52 (s, 3H), 2.4-2.5 (m, 1H), 2.32 (br d, 1H, J=9.4 Hz)

LC-MS ESI): Method 4 $t_R$=6.04 min; m/z (M+1)=505.07

The following compounds were prepared as described in Example 13, step 1.

| Example No | Structure Analytical Data/Amount reagents | Product Amount (Yield) |
|---|---|---|
| 61 | 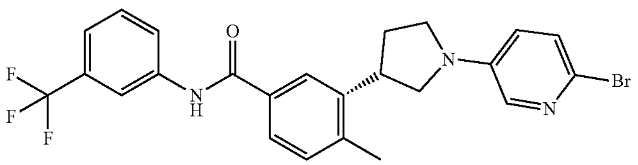<br>LC-MS (ESI): method 2 $t_R$ = 2.73 min; m/z (M + 1) = 506.92<br>2-bromo-5-fluoropyridine: 101 mg (1.5 eq.) Intermediate 17: 200 mg (1 eq.) | 54 mg (19%) |

-continued

| Example No | Structure<br>Analytical Data/Amount reagents | Product Amount (Yield) |
|---|---|---|
| 62 | 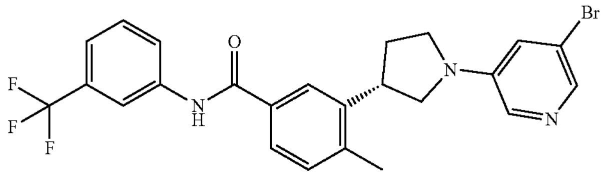 [SMILES: Cc1ccc(C(=O)Nc2cccc(C(F)(F)F)c2)cc1[C@@H]1CCN(c2cncc(Br)c2)C1]<br>(S)-3-(1-(5-bromopyridin-3-yl)pyrrolidin-3-yl)-4-methyl-N-(3-(trifluoromethyl)phenyl)benzamide<br>LC-MS (ESI): method 2 $t_R$ = 2.73 min; m/z (M + 1) = 506.91<br>3-bromo-5-fluoropyridine: 253 mg (5 eq.) Intermediate 17: 100 mg (1 eq.) | 80 mg (55%) |

The following Intermediate was prepared as described in Example 13, step 1:

| Intermediate No | Structure<br>Analytical Data/Amount reagents | Product Amount (Yield) |
|---|---|---|
| 38 | 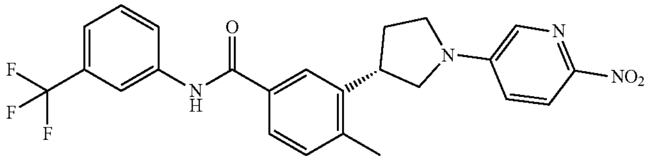 [SMILES: Cc1ccc(C(=O)Nc2cccc(C(F)(F)F)c2)cc1[C@@H]1CCN(c2ccc([N+](=O)[O-])nc2)C1]<br>LC-MS (ESI): method 2 $t_R$ = 1.26 min; m/z (M + 1) = 471.03<br>5-fluoro-2-nitropyridine: 82 mg (2 eq.) Intermediate 17: 100 mg (1 eq.) | 89 mg (66%) |

Example 14: preparation of 4-methyl-3-(1-nicotinoylpyrrolidin-3-yl)-N-(3-(trifluoromethyl)phenyl) benzamide

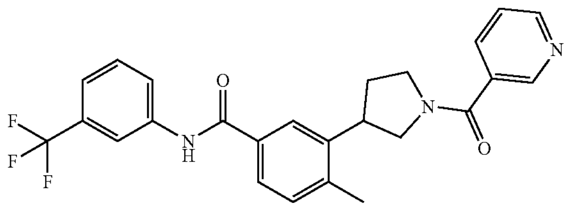 [SMILES: Cc1ccc(C(=O)Nc2cccc(C(F)(F)F)c2)cc1C1CCN(C(=O)c2cccnc2)C1]

Example 14

Step 1; 4-methyl-3-(1-nicotinoylpyrrolidin-3-yl)-N-(3-(trifluoromethyl)phenyl) benzamide Nicotinoyl chloride hydrochloride (38.3 mg, 0.215 mmol) was dissolved in pyridine (2 ml) then Intermediate 12 (75 mg, 0.215 mmol) was added and the mixture was stirred at RT overnight. To the reaction mixture water and DCM was added. Mixture was left stirring for 10 min, then phases were separated. Aqueous layer was extracted using DCM (3×). Combined organic layers were washed with 5% aq. sol. of citric acid, 2× with sat. aq. sol. of $NaHCO_3$ and finally with water. The combined organic phases were dried over $Na_2SO_4$ and then evaporated to give a residue that was purified by FCC Reverse phase (gradient A:B from 100:0 to 60:40 with 10 CV, eluent A: $H_2O$:ACN:HCOOH 95:5:0.1 eluent B:$H_2O$:ACN:HCOOH 5:95:0.1). The relevant fractions were combined and loaded onto an Isolute SCX-2 cartridge, washed with MeOH and the product was eluted with 2N methanolic ammonia. The residue was concentrated in vacuo to afford title compound (32 mg, 0.071 mmol, 32.8% yield).

$^1H$ NMR (acetone, 400 MHz) δ 9.6-9.9 (m, 1H), 8.78 (s, 1H), 8.62 (br dd, J=3.6, 15.7 Hz, 1H), 8.26 (br s, 1H), 7.9-8.2 (m, 3H), 7.80 (br dd, J=7.9, 18.6 Hz, 1H), 7.57 (br t, J=7.6 Hz, 1H), 7.2-7.5 (m, 3H), 3.54-4.15 (m, 5H), 2.51 (s, 2H), 2.09-2.40 (m, 3H).

LC-MS (ESI): Method 1 $t_R$=1.05 min; m/z (M+1)=454.12

Example 15 and Example 16: Preparation of (R)-4-methyl-3-(1-(pyridin-3-yl)pyrrolidin-3-yl)-N-(3-(trifluoromethyl)phenyl)benzamide and (S)-4-methyl-3-(1-(pyridin-3-yl)pyrrolidin-3-yl)-N-(3-(trifluoromethyl)phenyl)benzamide Example 15

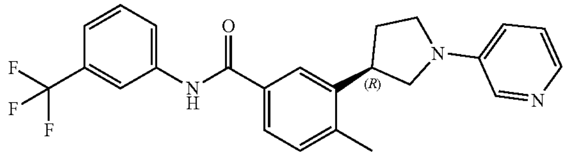

Example 16

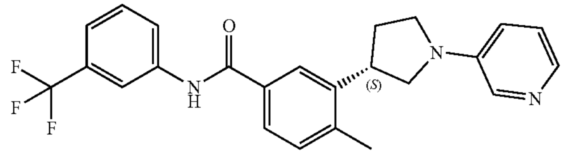

Step 1; tert-butyl 3-(2-methyl-5-((3-(trifluoromethyl)phenyl)carbamoyl) phenyl) pyrrolidine-1-carboxylate (Intermediate 13)

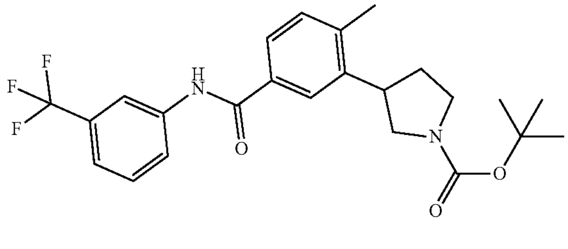 [SMILES: Cc1ccc(C(=O)Nc2cccc(C(F)(F)F)c2)cc1C1CCN(C(=O)OC(C)(C)C)C1]

To a solution of Intermediate 12 (6.40 g, 18.37 mmol) in DCM (150 ml) at rt di-tert-butyl dicarbonate (4.81 g, 22.05 mmol) was added. The reaction mixture was stirred overnight at rt and then concentrated in vacuo. The residue was purified by FCC (0-30% EtOAc in n-Heptane) to give the title compound (3.93 g, 8.76 mmol, 47.7% yield).

$^1$H NMR (acetone, 400 MHz) δ 9.76 (br s, 1H), 8.26 (s, 1H), 8.04 (d, J=8.1 Hz, 1H), 7.97 (s, 1H), 7.79 (d, J=7.5 Hz, 1H), 7.57 (t, J=8.0 Hz, 1H), 7.42 (d, J=7.7 Hz, 1H), 7.33 (d, J=7.9 Hz, 1H), 3.5-3.8 (m, 3H), 3.2-3.4 (m, 2H), 2.46 (s, 3H), 2.2-2.3 (m, 1H), 2.04-2.10 (m, 1H), 1.45 (s, 9H).

LC-MS (ESI): Method 2 $t_R$=2.67 min; m/z (M+1-tBu)=393.0

Step 2; tert-butyl 3-(2-methyl-5-((3-(trifluoromethyl)phenyl)carbamoyl) phenyl)pyrrolidine-1-carboxylate (Intermediate 14)

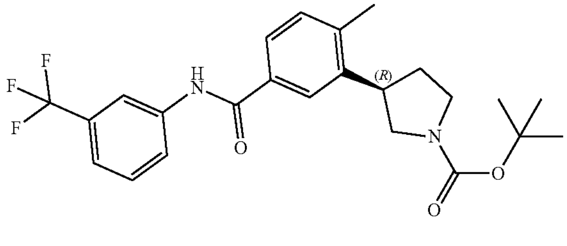

Intermediate 13, as racemic mixture, (3.93 g, 8.76 mmol) was dissolved to 142 mg/mL solution in MeOH and was then purified by chiral SFC following Method 5. Combined fractions of first eluting enantiomer were then evaporated to near dryness using a rotary evaporator. The resultant solids were then transferred into final vessels with MeOH which was removed under a stream of compressed air at 35° C. before being stored in a vacuum oven at 35° C. and 5 mbar until constant weight to afford the title compound (250 mg, 0.557 mmol).

Chiral analysis (SFC Method 6): $t_R$ 1.16 min, ee 100%

LC-MS (ESI): Method 7 $t_R$=1.79 min; m/z (M+1-tBu)=393.3

IR and VCD Spectroscopy: configuration R was assigned.

Step 3; tert-butyl 3-(2-methyl-5-((3-(trifluoromethyl)phenyl)carbamoyl) phenyl) pyrrolidine-1-carboxylate (Intermediate 15)

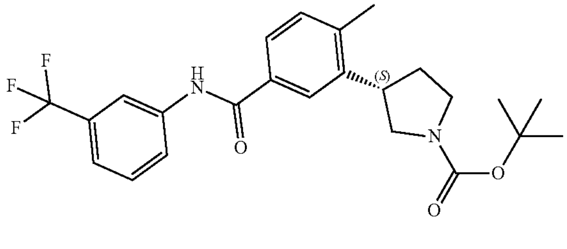

Performing the same chiral SFC separations per Step 2, combined fractions of second eluting enantiomer were evaporated to afford the title compound (1.88 g).

Chiral analysis (SFC Method 6): $t_R$ 2.46 min, ee 99.8%

LC-MS (ESI): Method 7 $t_R$=1.79 min; m/z (M+1-tBu)=393.3

IR and VCD Spectroscopy: configuration S was assigned.

Step 4; (R)-4-methyl-3-(pyrrolidin-3-yl)-N-(3-(trifluoromethyl)phenyl) benzamide 2,2,2-trifluoroacetate (Intermediate 16)

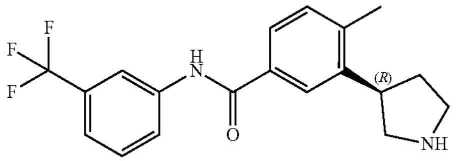

-continued

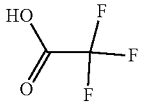

Intermediate 14 (250 mg, 0.557 mmol) was placed in a 40 mL vial then trifluoroacetic acid (500 µl, 6.49 mmol) was added dropwise.

The mixture was stirred at rt for 10 min. EtOH was added and the solvent was evaporated under reduced pressure to give the desired product without further purification (215 mg, 0.557 mmol, 100% yield).

Step 5; (S)-4-methyl-3-(pyrrolidin-3-yl)-N-(3-(trifluoromethyl)phenyl) benzamide 2,2,2-trifluoroacetate (Intermediate 17)

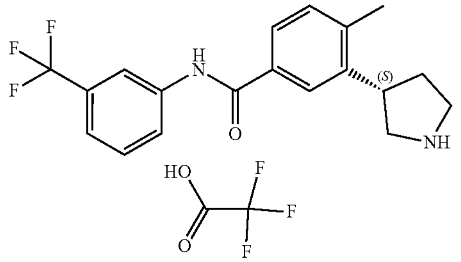

Following the procedure described in step 4 starting from Intermediate 15 the title product was obtained (250 mg, 0.541 mmol, 95% yield).

Step 6; (R)-4-methyl-3-(1-(pyridin-3-yl)pyrrolidin-3-yl)-N-(3-(trifluoromethyl) phenyl)benzamide (Example 15)

Intermediate 16 (60 mg, 0.156 mmol) and 3-bromopyridine (37.0 mg, 0.234 mmol) were reacted as described in Example 5, step 6, to afford the title compound (20.3 mg, 0.048 mmol, 30.6% yield).

$^1$H NMR (ACN-d3, 400 MHz) δ 8.88 (br s, 1H), 8.14 (s, 1H), 8.03 (d, J=2.8 Hz, 1H), 7.8-7.9 (m, 3H), 7.73 (dd, J=1.9, 8.0 Hz 1H), 7.54 (t, J=8.0 Hz, 1H), 7.43 (d, J=7.9 Hz, 1H), 7.37 (d, J=7.9 Hz, 1H), 7.16 (dd, J=4.6, 8.6 Hz, 1H), 6.95 (ddd, J=1.3, 3.0, 8.4 Hz, 1H), 3.86 (dd, J=7.2, 9.0 Hz, 1H), 3.7-3.8 (m, 1H), 3.4-3.6 (m, 3H), 2.49 (s, 3H), 2.4-2.5 (m, 1H), 2.2-2.3 (m, 1H).

LC-MS (ESI): Method 4 $t_R$=5.40 min; m/z (M+1)=426.29

Step 7; (S)-4-methyl-3-(1-(pyridin-3-yl)pyrrolidin-3-yl)-N-(3-(trifluoromethyl) phenyl)benzamide (Example 16)

Intermediate 17 (70 mg, 0.151 mmol) and 3-bromopyridine (36.0 mg, 0.227 mmol) were reacted as described in Example 5, step 6, to afford the title compound (43.2 mg, 0.090 mmol, 59.900 yield).

$^1$H NMV (ACN-d3, 400 MHz) δ 8.91 (br s, 1H), 8.15 (s, 1H), 8.02 (d, J=2.9 HzM, 1H), 7.8-7.9 (m, 3H), 7.73 (dd, J=1.5, 7.9 Hz, 1H), 7.54 (t, J=8.0 Hz, 1H), 7.43 (d, J=7.9 Hz, 1H), 7.37 (d, J=8.1 Hz, 1H), 7.18 (dd, J=4.7, 8.4 Hz, 1H), 6.98 (dd, J=2.4, 8.1 Hz, 1H), 3.8-3.9 (m, 1H), 3.7-3.8 (m, 1H), 3.4-3.6 (m, 3H), 2.49 (s, 3H), 2.4-2.5 (m, 1H), 2.1-2.4 (in, 1H).

LC-MS (ESI): Method 3 $t_R$=3.82 m7; m/z (M+1)=426.20

The following compounds were prepared as described for Example 5, step 6, applying the corresponding commercially available or synthesized bromo intermediate. The used procedures may involve minor variations, for example reaction temperature, reaction time, work-up conditions, in some cases, modification of catalysts, ligand (e.g. Pd-171 instead of Pd(dppf)$Cl_2$/RuPhos) or solvent (dioxane instead of DMA).

| Example No | Structure<br>Analytical Data/Amount reagents/Purification | Product Amount (Yield) |
|---|---|---|
| 20 | 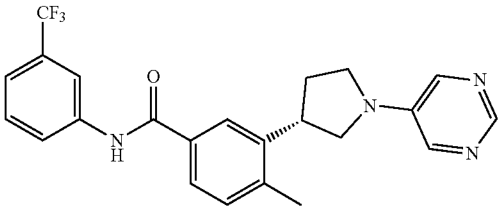 [SMILES: Cc1ccc(C(=O)Nc2cccc(C(F)(F)F)c2)cc1[C@@H]1CCN(c2cncnc2)C1]<br>LC-MS (ESI): Method 4 $t_R$ = 7.7 m/z (M + 1) = 427.40<br>$^1$H NMR (MeOH-d4, 400 MHz) δ 8.41 (s, 1H), 8.16 (s, 2H), 8.09 (s, 1H), 7.88-7.90 (m, 2H), 7.73 (dd, J = 2.0, 7.9 Hz, 1H), 7.51 (t, J = 8.0 Hz, 1H), 7.3-7.4 (m, 2H), 3.7-3.9 (m, 2H), 3.63 (dt, J = 3.5, 8.7 Hz, 1H), 3.4-3.5 (m, 2H), 2.4-2.5 (m, 4H), 2.2-2.3 (m, 1H)<br>5-bromo pyrimidine: 46 mg (1.0 eq.) Intermediate 17: 85 mg (1 eq.);<br>FCC/SCX-2 | 21 mg (20%) |

-continued

| Example No | Structure Analytical Data/Amount reagents/Purification | Product Amount (Yield) |
|---|---|---|
| 25 | 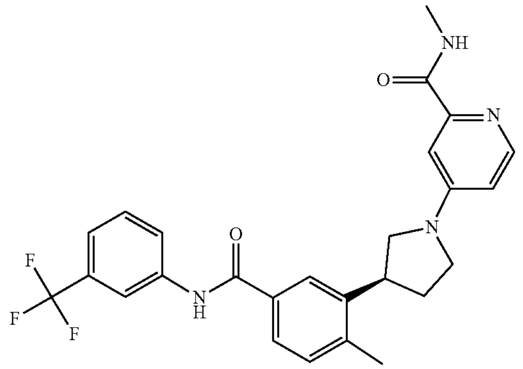 [SMILES: CNC(=O)c1cc(N2CC[C@@H](c3cc(C(=O)Nc4cccc(C(F)(F)F)c4)ccc3C)C2)ccn1] LC-MS (ESI): Method 4 $t_R$ = 5.8 m/z (M + 1) = 483.30 $^1$H NMR (MEOH-d4, 400 MHz) δ 8.12 (d, 1H, J = 5.7 Hz), 8.08 (s, 1H), 7.87 (br s, 2H), 7.7-7.8 (m, 1H), 7.50 (t, 1H, J = 8.0 Hz), 7.3-7.4 (m, 2H), 7.26 (d, 1H, J = 2.2 Hz), 6.63 (dd, 1H, J = 2.4, 5.7 Hz), 3.85 (td, 2H, J = 7.6, 15.5 Hz), 3.6-3.7 (m, 1H), 3.4-3.6 (m, 2H), 2.92 (s, 3H), 2.42-2.56 (m, 4H), 2.2-2.3 (m, 1H) 4-bromo-N-methylpicolinamide: 56 mg (1.0 eq.) Intermediate 17: 120 mg (1 eq.); FCC/SCX-2 | 33 mg (26%) |
| 26 | 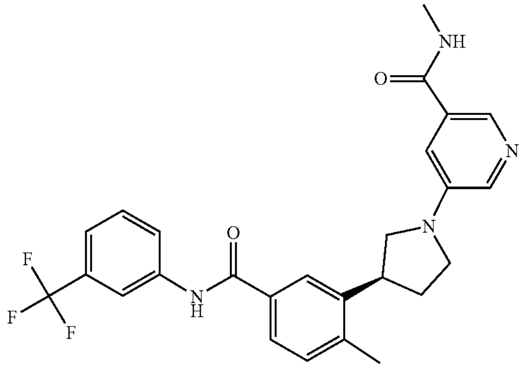 [SMILES: CNC(=O)c1cncc(N2CC[C@@H](c3cc(C(=O)Nc4cccc(C(F)(F)F)c4)ccc3C)C2)c1] LC-MS (ESI): Method 3 $t_R$ = 4.1 m/z (M + 1) = 483.20 $^1$H NMR (MEOH-d4, 400 MHz) δ 8.19 (br s, 1H), 8.00-8.12 (m, 2H), 7.88 (br s, 2H), 7.73 (br d, 1H, J = 7.2 Hz), 7.50 (br t, 1H, J = 7.6 Hz), 7.3-7.4 (m, 3H), 3.7-4.0 (m, 2H), 3.60-3.70 (m, 1H), 3.4-3.6 (m, 2H), 2.90 (br s, 3H), 2.40-2.62 (m, 4H), 2.28 (br d, 1H, J = 8.3 Hz) 5-bromo-N-methylnicotinamide: 45 mg (1.0 eq.) Intermediate 17: 97 mg (1 eq.); FCC/SCX-2 | 29 mg (29%) |
| 27 | 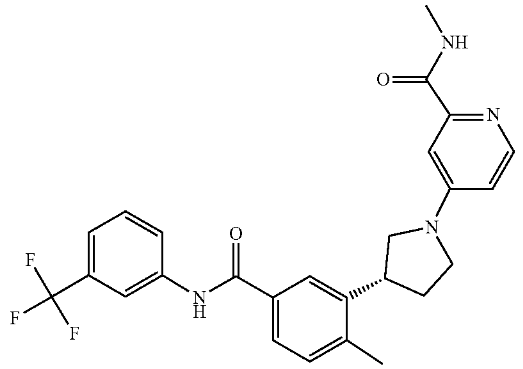 [SMILES: CNC(=O)c1cc(N2CC[C@H](c3cc(C(=O)Nc4cccc(C(F)(F)F)c4)ccc3C)C2)ccn1] LC-MS (ESI): Method 3 $t_R$ = 3.6 m/z (M + 1) = 483.30 $^1$H NMR (MEOH-d4, 400 MHz) δ 8.15 (d, 1H, J = 5.9 Hz), 8.10 (s, 1H), 7.9-7.9 (m, 2H), 7.75 (dd, 1H, J = 1.8, 7.9 Hz), 7.52 (t, 1H, J = 8.0 Hz), 7.3-7.4 (m, 2H), 7.28 (d, 1H, J = 2.4 Hz), 6.65 (dd, 1H, J = 2.5, 5.8 Hz), 3.8-3.9 | 35 mg (34%) |

-continued

| Example No | Structure<br>Analytical Data/Amount reagents/Purification | Product Amount (Yield) |
|---|---|---|
| | (m, 2H), 3.6-3.7 (m, 1H), 3.4-3.6 (m, 2H), 2.94 (s, 3H), 2.51 (s, 3H), 2.5-2.5 (m, 1H), 2.2-2.3 (m, 1H)<br>4-bromo-N-methylpicolinamide: 47 mg (1.0 eq.) Intermediate 16: 100 mg (1 eq.); FCC/SCX-2 | |
| 28 | 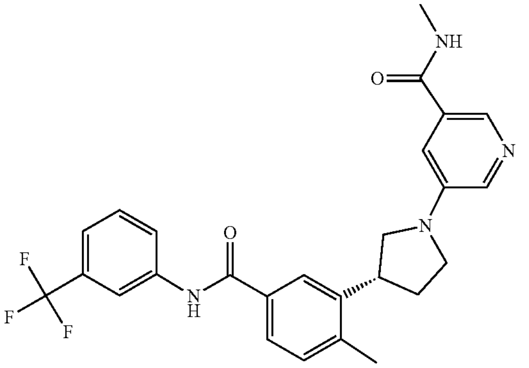 [SMILES: CNC(=O)c1cncc(N2CC[C@H](c3cc(C(=O)Nc4cccc(C(F)(F)F)c4)ccc3C)C2)c1]<br>LC-MS (ESI): Method 3 $t_R$ = 4.1 m/z (M + 1) = 483.20<br>$^1$H NMR (MEOH-d4, 400 MHz) δ 8.19 (d, 1H, J = 1.8 Hz), 8.08 (s, 1H), 8.04 (d, 1H, J = 2.8 Hz), 7.8-7.9 (m, 2H), 7.73 (dd, 1H, J = 1.8, 7.9 Hz), 7.50 (t, 1H, J = 8.0 Hz), 7.3-7.4 (m, 3H), 3.8-3.9 (m, 2H), 3.63 (dt, 1H, J = 3.7, 8.8 Hz), 3.5-3.6 (m, 2H), 2.90 (s, 3H), 2.45-2.58 (m 4H), 2.2-2.3 (m, 1H)<br>5-bromo-N-methylnicotinamide: 51 mg (1.0 eq.) Intermediate 16: 110 mg (1 eq.); FCC/SCX-2 | 32 mg (28%) |
| 29 | 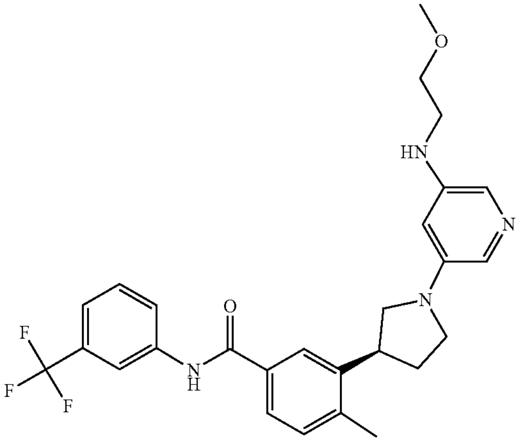 [SMILES: COCCNc1cncc(N2CC[C@@H](c3cc(C(=O)Nc4cccc(C(F)(F)F)c4)ccc3C)C2)c1]<br>LC-MS (ESI): Method 3 $t_R$ = 4.1 m/z (M + 1) = 499.30<br>$^1$H NMR (MEOH-d4, 400 MHz) δ 8.09 (s, 1H), 7.8-7.9 (m, 2H), 7.72 (d, 1H, J = 7.9 Hz), 7.51 (t, 1H, J = 8.0 Hz), 7.39 (d, 1H, J = 7.7 Hz), 7.34 (d, 1H, J = 7.9 Hz), 7.30 (d, 1H, J = 2.0 Hz), 7.26 (d, 1H, J = 2.0 Hz), 6.27 (s, 1H), 3.8-3.9 (m, 1H), 3.71 (t, 1H, J = 8.4 Hz), 3.3-3.6 (m, 5H), 3.35 (s, 3H), 3.2-3.3 (m, 2H), 2.32-2.53 (m, 4H), 2.2-2.3 (m, 1H)<br>5-bromo-N-(2-methoxyethyl)pyridin-3-amine: 43 mg (1.0 eq.) Intermediate 17: 85 mg (1 eq.); FCC/SCX-2 | 19 mg (21%) |

-continued

| Example No | Structure Analytical Data/Amount reagents/Purification | Product Amount (Yield) |
|---|---|---|
| 30 | 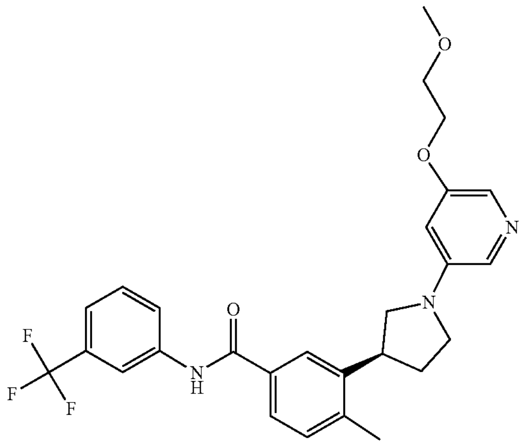 [SMILES: COCCOc1cncc(N2CC[C@@H](c3cc(C(=O)Nc4cccc(C(F)(F)F)c4)ccc3C)C2)c1]<br>LC-MS (ESI): Method 3 $t_R$ = 4.2 m/z (M + 1) = 500.30<br>$^1$H NMR (MEOH-d4, 400 MHz) δ 8.09 (s, 1H), 7.87 (br s, 2H), 7.72 (d, 1H, J = 7.9 Hz), 7.5-7.6 (m, 3H), 7.3-7.4 (m, 2H), 6.59 (s, 1H), 4.1-4.2 (m, 2H), 3.8-3.9 (m, 1H), 3.7-3.8 (m, 3H), 3.4-3.6 (m, 3H), 3.39 (s, 3H), 2.49 (s, 3H), 2.4-2.5 (m, 1H), 2.2-2.3 (m, 1H)<br>5-bromo-N-(2-methoxyethyl)pyridin-3-amine: 43 mg (1.0 eq.)<br>Intermediate 17: 85 mg (1 eq.); FCC/SCX-2 | 19 mg (21%) |
| 31 | 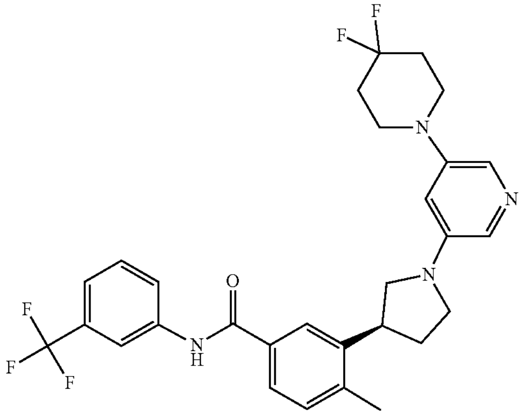 [SMILES: Cc1ccc(C(=O)Nc2cccc(C(F)(F)F)c2)cc1[C@@H]1CCN(c2cncc(N3CCC(F)(F)CC3)c2)C1]<br>LC-MS (ESI): Method 3 $t_R$ = 4.7 m/z (M + 1) = 545.30<br>$^1$H NMR (MEOH-d4, 400 MHz) δ 8.08 (s, 1H), 7.8-7.9 (m, 2H), 7.71 (dd, 1H, J = 1.5, 7.9 Hz), 7.59 (d, 1H, J = 2.0 Hz), 7.4-7.5 (m, 2H), 7.38 (d, 1H, J = 7.7 Hz), 7.33 (d, 1H, J = 7.9 Hz), 6.56 (s, 1H), 3.8-3.9 (m, 1H), 3.73 (t, 1H, J = 8.3 Hz), 3.3-3.6 (m, 7H), 2.48 (s, 3H), 2.4-2.5 (m, 1H), 2.2-2.3 (m, 1H), 2.0-2.1 (m, 4H)<br>Intermediate 24: 51 mg (1.0 eq.) Intermediate 17: 85 mg (1 eq.); FCC/SCX-2 | 13 mg (13%) |

-continued

| Example No | Structure Analytical Data/Amount reagents/Purification | Product Amount (Yield) |
| --- | --- | --- |
| 32 | 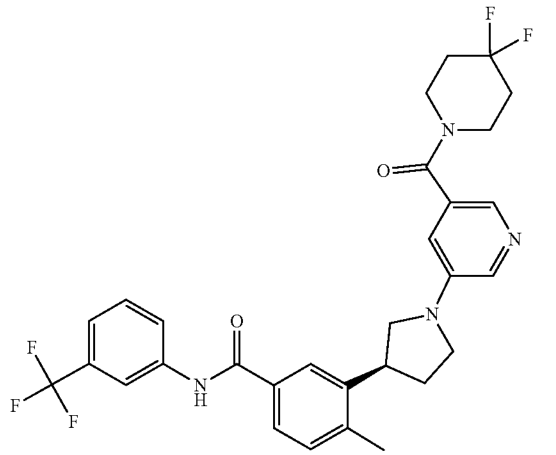 [SMILES: Cc1ccc(C(=O)Nc2cccc(C(F)(F)F)c2)cc1[C@@H]1CCN(c2cncc(C(=O)N3CCC(F)(F)CC3)c2)C1] LC-MS (ESI): Method 3 $t_R$ = 5.0 m/z (M + 1) = 573.30 $^1$H NMR (MEOH-d4, 400 MHz) δ 8.08 (s, 1H), 8.03 (d, 1H, J = 2.4 Hz), 7.8-7.9 (m, 3H), 7.72 (dd, 1H, J = 1.8, 7.9 Hz), 7.51 (t, 1H, J = 8.0 Hz), 7.3-7.4 (m, 2H), 7.05 (br s, 1H), 3.7-3.9 (m, 4H), 3.4-3.6 (m, 5H), 2.42-2.53 (m, 4H), 2.46 (br d, 1H, J = 4.4 Hz), 2.2-2.4 (m, 1H), 1.9-2.1 (m, 4H) Intermediate 22: 56 mg (1.0 eq.) Intermediate 17: 85 mg (1 eq.); FCC/SCX-2 | 20 mg (19%) |
| 33 | 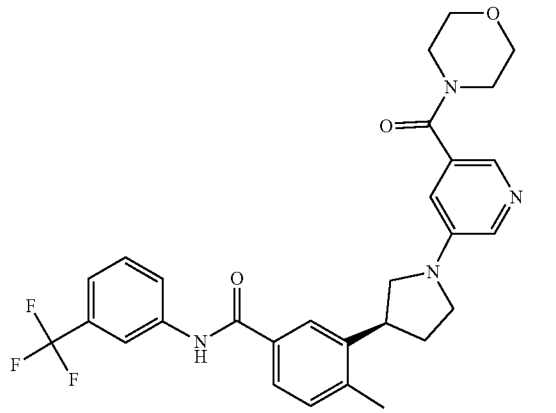 [SMILES: Cc1ccc(C(=O)Nc2cccc(C(F)(F)F)c2)cc1[C@@H]1CCN(c2cncc(C(=O)N3CCOCC3)c2)C1] LC-MS (ESI): Method 4 $t_R$ = 6.6 m/z (M + 1) = 539.30 $^1$H NMR (MEOH-d4, 400 MHz) δ 8.42 (s, 1H), 8.09 (s, 1H), 8.02 (d, 1H, J = 2.6 Hz), 7.8-7.9 (m, 3H), 7.73 (d, 1H, J = 7.9 Hz), 7.51 (t, 1H, J = 8.0 Hz), 7.3-7.4 (m, 2H), 7.03 (s, 1H), 3.37-3.98 (m, 13H), 3.4-3.7 (m, 7H), 2.39-2,54 (m, 4H), 2.46 (br d, 1H, J = 4.6 Hz), 2.25 (br dd, 1H, J = 8.4, 12.2 Hz) (5-bromopyridin-3-yl)(morpholino)methanone: 62 mg (1.0 eq.) Intermediate 17: 85 mg (1 eq.); FCC/SCX-2 | 20 mg (20%) |

-continued

| Example No | Structure<br>Analytical Data/Amount reagents/Purification | Product Amount (Yield) |
|---|---|---|
| 34 | 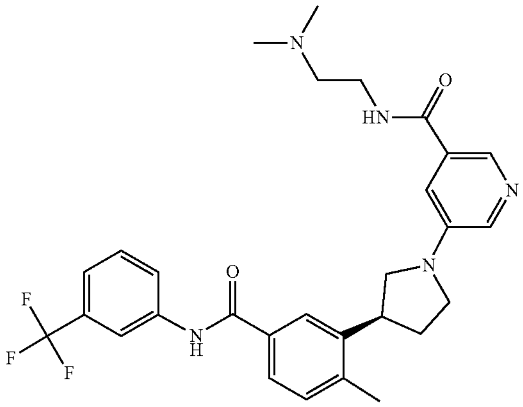 [SMILES: Cc1ccc(C(=O)Nc2cccc(C(F)(F)F)c2)cc1[C@@H]1CCN(c2cncc(C(=O)NCCN(C)C)c2)C1]<br>LC-MS (ESI): Method 4 $t_R$ = 5.6 m/z (M + 1) = 540.40<br>$^1$H NMR (MEOH-d4, 400 MHz) δ 8.23 (s, 1H), 8.08 (s, 1H), 8.04 (d, 1H, J = 2.6 Hz), 7.88 (br s, 2H), 7.7-7.8 (m, 1H), 7.50 (br t, 1H, J = 8.0 Hz), 7.3-7.4 (m, 3H), 3.8-3.9 (m, 2H), 3.6-3.7 (m, 1H), 3.5-3.6 (m, 4H), 2.59 (t, 2H, J = 6.7 Hz), 2.50 (s, 3H), 2.31 (s, 6H), 2.2-2.3 (m, 2H)<br>Intermediate 3: 94 mg (1.5 eq.) Intermediate 17: 80 mg (1 eq.); FCC/SCX-2 | 15 mg (12%) |
| 35 | 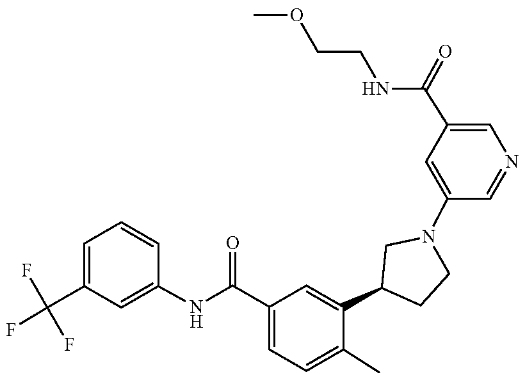 [SMILES: COCCNC(=O)c1cncc(N2CC[C@@H](c3cc(C(=O)Nc4cccc(C(F)(F)F)c4)ccc3C)C2)c1]<br>LC-MS (ESI): Method 4 $t_R$ = 7.1 m/z (M + 1) = 527.30<br>$^1$H NMR (MEOH-d4, 400 MHz) δ 8.21 (br s, 1H), 8.08 (s, 1H), 8.05 (br s, 1H), 7.8-7.9 (m, 2H), 7.73 (dd, 1H, J = 1.5, 7.9 Hz), 7.51 (t, 1H, J = 8.0 Hz), 7.3-7.4 (m, 3H), 3.8-3.9 (m, 2H), 3.44-3.71 (m, 7H), 3.35 (s, 3H), 2.42-2.56 (m, 4H), 2.2-2.4 (m, 1H)<br>Intermediate 4: 59 mg (1 eq.) Intermediate 17: 80 mg (1 eq.); FCC/SCX-2 | 14 mg (12%) |

-continued

| Example No | Structure Analytical Data/Amount reagents/Purification | Product Amount (Yield) |
|---|---|---|
| 36 | 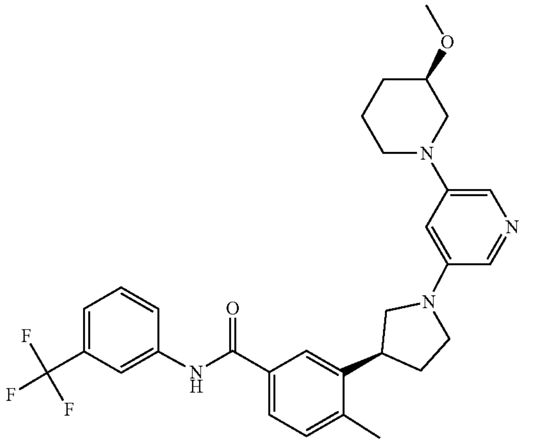 [SMILES: CO[C@@H]1CCCN(c2cncc(N3CC[C@@H](c4cc(C(=O)Nc5cccc(C(F)(F)F)c5)ccc4C)C3)c2)C1]<br>LC-MS (ESI): Method 4 $t_R$ = 7.0 m/z (M + 1) = 539.40<br>$^1$H NMR (MEOH-d4, 400 MHz) δ 8.09 (s, 1H), 7.8-7.9 (m, 2H), 7.71 (dd, 1H, J = 1.4, 8.0 Hz), 7.5-7.6 (m, 2H), 7.3-7.4 (m, 3H), 6.51 (s, 1H), 3.7-3.9 (m, 2H), 3.56 (br dd, 2H, J = 4.2, 9.9 Hz), 3.3-3.5 (m, 7H), 2.8-3.0 (m, 2H), 2.49 (s, 3H), 2.4-2.5 (m, 1H), 2.21 (qd, 1H, J = 8.4, 12.1 Hz), 1.9-2.0 (m, 1H), 1.8-1.9 (m, 1H), 1.4-1.7 (m, 2H)<br>(S)-3-bromo-5-(3-methoxypiperidin-1-yl)pyridine Intermediate 25: 50 mg (1.0 eq.) Intermediate 17: 85 mg (1 eq.); FCC/SCX-2 | 20 mg (20%) |
| 37 | 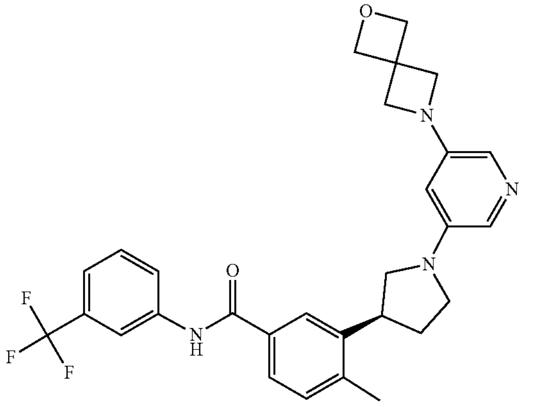 [SMILES: Cc1ccc(C(=O)Nc2cccc(C(F)(F)F)c2)cc1[C@@H]1CCN(c2cncc(N3CC4(COC4)C3)c2)C1]<br>LC-MS (ESI): Method 4 $t_R$ = 6.2 m/z (M + 1) = 523.30<br>$^1$H NMR (MEOH-d4, 400 MHz) δ 8.08 (s, 1H), 7.8-7.9 (m, 2H), 7.6-7.8 (m, 1H), 7.51 (t, 1H, J = 8.0 Hz), 7.3-7.4 (m, 3H), 7.12 (d, 1H, J = 2.0 Hz), 6.05 (s, 1H), 4.81 (s, 4H), 4.03 (s, 4H), 3.8-3.9 (m, 1H), 3.7-3.8 (m, 1H), 3.54 (br d, 1H, J = 3.9 Hz), 3.4-3.5 (m, 2H), 2.34-2.58 (m, 4H), 2.22 (br d, 1H, J = 8.6 Hz)<br>6-(5-bromopyridin-3-yl)-2-oxa-6-azaspiro[3.3]heptane Intermediate 26: 47 mg (1.0 eq.) Intermediate 17: 85 mg (1 eq.); FCC/SCX-2 | 9 mg (9%) |
| 38 | 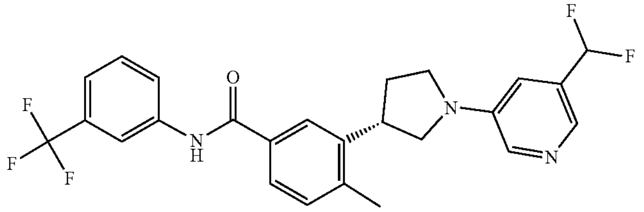 [SMILES: Cc1ccc(C(=O)Nc2cccc(C(F)(F)F)c2)cc1[C@@H]1CCN(c2cncc(C(F)F)c2)C1]<br>LC-MS (ESI): Method 3 $t_R$ = 5.4 m/z (M + 1) = 476.30<br>$^1$H NMR (ACN-d3, 400 MHz) δ 8.89 (br s, 1H), 8.14 (s, 2H), 8.03 (s, 1H), 7.91 (d, 1H, J = 8.3 Hz), 7.8-7.9 (m, 1H), 7.73 (dd, 1H, J = 1.8, 7.9 Hz), 7.54 (t, 1H, J = 8.0 Hz), 7.43 (d, 1H, J = 7.7 Hz), 7.37 (d, 1H, J = 8.1 Hz), 6.79 (t, 1H, J = 60.0 Hz), 3.8-3.9 (m, 2H), 3.60 (dd, 1H, J = 3.5, 8.6 Hz), | 47 mg (43%) |

-continued

| Example No | Structure Analytical Data/Amount reagents/Purification | Product Amount (Yield) |
|---|---|---|
| | 3.4-3.5 (m, 2H), 2.49 (s, 3H), 2.4-2.5 (m, 1H), 2.26 (dd, 1H, J = 8.7, 12.2 Hz)<br>3-bromo-5-(difluoromethyl)pyridine: 72 mg (1.5 eq.) Intermediate 17: 80 mg (1 eq.); FCC/SCX-2 | |
| 39 | 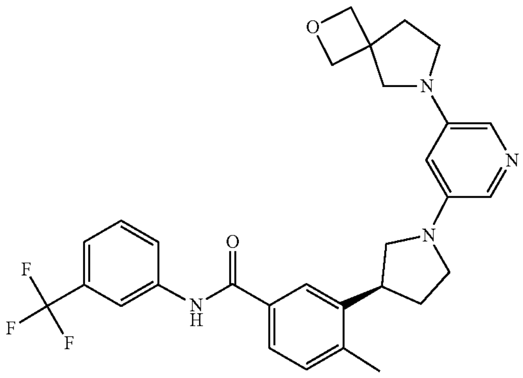 [SMILES: Cc1ccc(C(=O)Nc2cccc(C(F)(F)F)c2)cc1[C@@H]1CCN(c2cncc(N3CCC4(COC4)C3)c2)C1]<br>LC-MS (ESI): Method 4 $t_R$ = 6.8 m/z (M + 1) = 537.40<br>$^{1}$H NMR (MeOH-d4, 400 MHz) δ 8.09 (s, 1H), 7.8-7.9 (m, 2H), 7.72 (dd, 1H, J = 1.8, 7.9 Hz), 7.50 (t, 1H, J = 8.0 Hz), 7.21-7.43 (m, 4H), 6.18 (s, 1H), 4.5-4.8 (m, 4H), 3.8-3.9 (m, 1H), 3.7-3.8 (m, 1H), 3.4-3.6 (m, 5H), 3.3-3.3 (m, 2H), 2.49 (s, 3H), 2.37-2.44 (m, 2H), 2.2-2.4 (m, 2H)<br>6-(5-bromopyridin-3-yl)-2-oxa-6-azaspiro[3.4]octane Intermediate 27: 50 mg (1.0 eq.) Intermediate 17: 85 mg (1 eq.); FCC/SCX-2 | 9 mg (9%) |
| 40 | 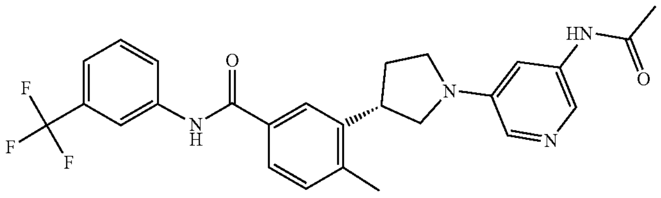 [SMILES: CC(=O)Nc1cncc(N2CC[C@@H](c3cc(C(=O)Nc4cccc(C(F)(F)F)c4)ccc3C)C2)c1]<br>LC-MS (ESI): Method 4 $t_R$ = 5.9 m/z (M + 1) = 483.30<br>$^{1}$H NMR (DMSO-d6, 400 MHz) δ 10.38 (s, 1H), 10.05 (br s, 1H), 8.17 (s, 1H), 8.05 (s, 1H), 7.99 (br d, 1H, J = 8.3 Hz), 7.8-7.9 (m, 1H), 7.7-7.8 (m, 2H), 7.55 (t, 1H, J = 8.0 Hz), 7.3-7.4 (m, 3H), 3.6-3.8 (m, 2H), 3.4-3.5 (m, 1H), 3.3-3.4 (m, 2H), 2.43 (s, 3H), 2.3-2.4 (m, 1H), 2.1-2.3 (m, 1H), 2.02 (s, 3H)<br>N-(5-bromopyridin-3-yl)acetamide Intermediate 28: 65 mg (1.5 eq.) Intermediate 17: 70 mg (1 eq.); FCC/SCX-2 | 21 mg (22%) |
| 41 | 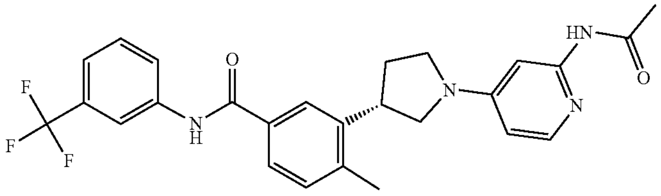 [SMILES: CC(=O)Nc1cc(N2CC[C@@H](c3cc(C(=O)Nc4cccc(C(F)(F)F)c4)ccc3C)C2)ccn1]<br>LC-MS (ESI): Method 4 $t_R$ = 5.8 m/z (M + 1) = 483.40<br>$^{1}$H NMR (DMSO-d6, 400 MHz) δ 10.38 (s, 1H), 10.07 (br s, 1H), 8.16 (s, 1H), 8.00 (br d, 1H, J = 8.1 Hz), 7.83 (d, 1H, J = 5.7 Hz), 7.76 (dd, 1H, J = 1.5, 7.9 Hz), 7.55 (t, 1H, J = 8.0 Hz), 7.41 (d, 1H, J = 7.9 Hz), 7.3-7.4 (m, 2H), 6.3-6.3 (m, 1H), 3.7-3.8 (m, 2H), 3.5-3.6 (m, 1H), 3.3-3.4 (m, 2H), 2.43 (s, 3H), 2.3-2.4 (m, 1H), 2.18 (br dd, 1H, J = 9.0, 11.8 Hz), 2.01 (s, 3H)<br>N-(4-bromopyridin-2-yl)acetamide: 65 mg (1.5 eq.) Intermediate 17: 70 mg (1 eq.); FCC/SCX-2 | 15 mg (15%) |

-continued

| Example No | Structure<br>Analytical Data/Amount reagents/Purification | Product Amount (Yield) |
|---|---|---|
| 42 | 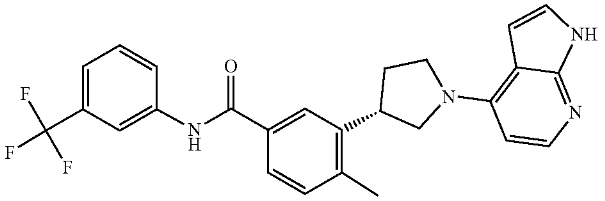 [SMILES: Cc1ccc(C(=O)Nc2cccc(C(F)(F)F)c2)cc1[C@@H]1CCN(c2ccnc3[nH]ccc23)C1]<br>LC-MS (ESI): Method 4 $t_R$ = 6.3 m/z (M + 1) = 465.30<br>$^1$H NMR (ACN-d3, 400 MHz) δ 9.47 and 9.65 (br s, 2H), 8.20 (s, 1H), 7.9-8.0 (m, 2H), 7.89 (d, 1H, J = 5.7 Hz), 7.78 (dd, 1H, J = 2.0, 7.9 Hz), 7.53 (t, 1H, J = 7.9 Hz), 7.3-7.5 (m, 2H), 7.04 (d, 1H, J = 3.7 Hz), 6.67 (d, 1H, J = 3.5 Hz), 6.09 (d, 1H, J = 5.7 Hz), 4.0-4.1 (m, 1H), 3.7-3.9 (m, 3H), 3.4-3.6 (m, 1H), 2.48 (s, 3H), 2.3-2.4 (m, 2H)<br>4-bromo-1H-pyrrolo[2,3-b]pyridine: 85 mg (1.5 eq.) Intermediate 17: 100 mg (1 eq.); FCC/SCX-2 | 37 mg (28%) |
| 43 | 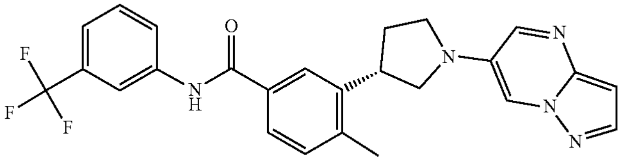 [SMILES: Cc1ccc(C(=O)Nc2cccc(C(F)(F)F)c2)cc1[C@@H]1CCN(c2cnc3ccnn3c2)C1]<br>LC-MS (ESI): Method 4 $t_R$ = 6.5 m/z (M + 1) = 466.30<br>$^1$H NMR (ACN-d3, 400 MHz) δ 8.94 (br s, 1H), 8.15 (s, 1H), 8.06 (d, 1H, J = 5.3 Hz), 7.90-7.94 (m, 3H), 7.75 (dd, 1H, J = 2.0, 7.9 Hz), 7.55 (t, 1H, J = 8.0 Hz), 7.3-7.5 (m, 2H), 6.33 (d, 1H, J = 2.2 Hz), 5.91 (d, 1H, J = 5.3 Hz), 4.47 (br dd, 1H, J = 8.0, 10.4 Hz), 4.2-4.3 (m, 1H), 4.0-4.1 (m, 2H), 3.8-3.9 (m, 1H), 2.49 (s, 3H), 2.43 (dtd, 1H, J = 3.4, 6.5, 12.4 Hz), 2.27 (ddd, 2H, J = 9.5, 12.1, 17.8 Hz)<br>6-bromopyrazolo[1,5-a]pyrimidine: 85 mg (1.5 eq.) Intermediate 17: 100 mg (1 eq.); FCC/SCX-2 | 34 mg (26%) |
| 44 | 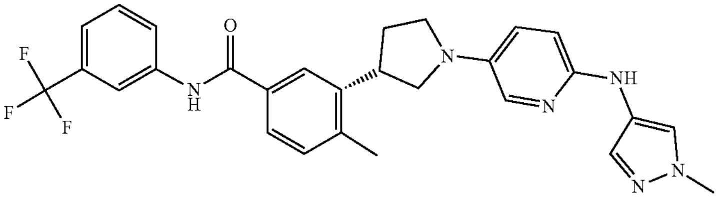<br>LC-MS (ESI): Method 4 $t_R$ = 6.4 m/z (M + 1) = 521.20<br>$^1$H NMR (acetone, 400 MHz) δ 9.72 (br s, 1H), 8.25 (s, 1H), 8.0-8.0 (m, 2H), 7.87 (s, 1H), 7.80 (dd, 1H, J = 1.8, 7.9 Hz), 7.62 (d, 1H, J = 2.9 Hz), 7.54 (t, 1H, J = 8.0 Hz), 7.2-7.4 (m, 4H), 7.0-7.0 (m, 1H), 6.64 (d, 1H, J = 8.8 Hz), 3.8-3.9 (m, 1H), 3.79 (s, 3H), 3.6-3.7 (m, 1H), 3.51 (dt, 1H, J = 3.5, 8.6 Hz), 3.3-3.4 (m, 2H), 2.50 (s, 3H), 2.43 (br dd, 1H, J = 3.5, 12.1 Hz), 2.1-2.3 (m, 1H)<br>1-methylpyrazol-4-amine: 16 mg (1.5 eq.); Example 61: 54 mg (1 eq.); FCC | 11 mg (20%) |

-continued

| Example No | Structure<br>Analytical Data/Amount reagents/Purification | Product Amount (Yield) |
|---|---|---|
| 45 | 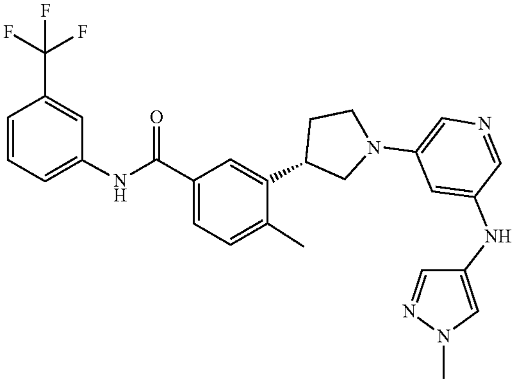 [SMILES: Cc1ccc(C(=O)Nc2cccc(C(F)(F)F)c2)cc1[C@@H]1CCN(c2cncc(Nc3cnn(C)c3)c2)C1]<br>LC-MS (ESI): Method 4 $t_R$ = 6.1 m/z (M + 1) = 521.30<br>$^1$H NMR (acetone, 400 MHz) δ 9.76 (br s, 1H), 8.26 (s, 1H), 8.0-8.1 (m, 2H), 7.82 (dd, 1H, J = 2.0, 7.9 Hz), 7.5-7.6 (m, 3H), 7.4-7.5 (m, 2H), 7.37 (d, 1H, J = 7.9 Hz), 7.32 (s, 1H), 6.71 (s, 1H), 6.38 (t, 1H, J = 2.3 Hz), 3.8-3.9 (m, 1H), 3.82 (s, 3H), 3.7-3.8 (m, 1H), 3.55 (dt, 1H, J = 3.3, 8.8 Hz), 3.3-3.5 (m, 2H), 2.51 (s, 3H), 2.4-2.5 (m, 1H), 2.2-2.3 (m, 1H)<br>1-methylpyrazol-4-amine: 12 mg (1.5 eq.) Example 62: 40 mg (1 eq.); | 16 mg (39%) |
| 46 | 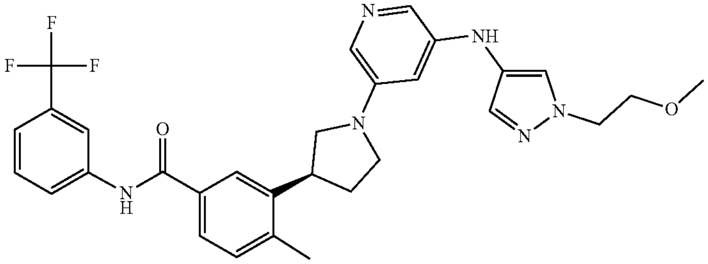 [SMILES: COCCn1cc(Nc2cncc(N3CC[C@@H](c4cc(C(=O)Nc5cccc(C(F)(F)F)c5)ccc4C)C3)c2)cn1]<br>LC-MS (ESI): Method 4 $t_R$ = 6.2 m/z (M + 1) = 565.30<br>$^1$H NMR (acetone, 400 MHz) δ 9.76 (br s, 1H), 8.26 (s, 1H), 8.0-8.1 (m, 2H), 7.82 (dd, 1H, J = 1.8, 7.9 Hz), 7.60 (s, 1H), 7.5-7.6 (m, 2H), 7.4-7.5 (m, 2H), 7.3-7.4 (m, 2H), 6.71 (s, 1H), 6.38 (t, 1H, J = 2.3 Hz), 4.22 (t, 2H, J = 5.4 Hz), 3.8-3.9 (m, 1H), 3.6-3.8 (m, 3H), 3.5-3.6 (m, 1H), 3.4-3.5 (m, 1H), 3.2-3.3 (m, 4H), 2.51 (s, 3H), 2.4-2.5 (m, 1H), 2.2-2.3 (m, 1H)<br>1-(2-methoxyethyl)pyrazol-4-amine: 17 mg (1.5 eq.)<br>(S)-3-(1-(5-bromopyridin-3-yl)pyrrolidin-3-yl)-4-methyl-N-(3-(trifluoromethyl)phenyl)benzamide: 40 mg (1 eq.); FCC | 7 mg (16%) |

The following intermediates and/or Examples were prepared as described in Example 5, step 6.

| Compound No | Structure<br>Analytical Data/Amount reagents/Purification | Product Amount (Yield) |
|---|---|---|
| Intermediate 18/ Example 63 | 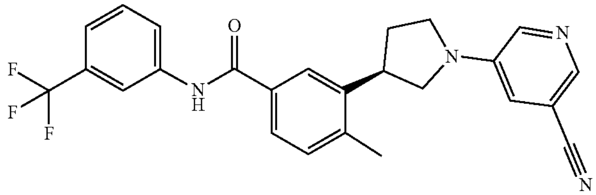 [SMILES: Cc1ccc(C(=O)Nc2cccc(C(F)(F)F)c2)cc1[C@H]1CCN(c2cncc(C#N)c2)C1]<br>(R)-3-(1-(5-cyanopyridin-3-yl)pyrrolidin-3-yl)-4-methyl-N-(3-(trifluoromethyl)phenyl)benzamide<br>LC-MS (ESI): method 1 $t_R$ = 1.29 min; m/z (M + 1) = 451.27<br>$^1$H NMR (acetone, 400 MHz) δ 9.75 (br s, 1H), 8.24 (br s, 2 H), 8.12 (br s, 1 H), 7.97-8.05 (m, 2 H), 7.81 (br d, J = 7.89 Hz, 1 H), 7.55 (br | 33 mg (28%) |

-continued

| Compound No | Structure Analytical Data/Amount reagents/Purification | Product Amount (Yield) |
|---|---|---|
| | t, J = 7.89 Hz, 1 H), 7.39-7.20 (m, 3 H), 3.23-4.2 (m, 5H), 2.53 (s, 3H), 2.3-2.4 (m, 1H), 0.76-1.54 (m, 1H).<br>5-bromo nicotinonitrile: 71 mg (1.5 eq.) Intermediate 16: 100 mg (1 eq.); FCC/SCX-2 | |
| Intermediate 19/ Example 64 | 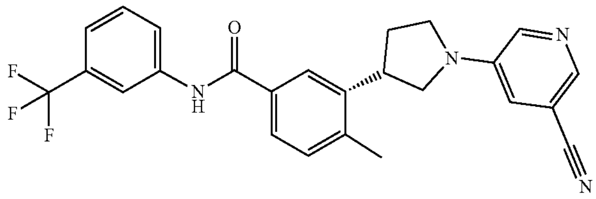<br>(S)-3-(1-(5-cyanopyridin-3-yl)pyrrolidin-3-yl)-4-methyl-N-(3-(trifluoromethyl)phenyl)benzamide<br>LC-MS (ESI): method 1 $t_R$ = 1.29 min; m/z (M + 1) = 451.27<br>$^1$H NMR (acetone, 400 MHz) δ 9.75 (br s, 1H), 8.24 (br s, 2 H), 8.12 (br s, 1 H), 7.97-8.05 (m, 2 H), 7.81 (br d, J = 7.89 Hz, 1 H), 7.55 (br t, J = 7.89 Hz, 1 H), 7.39-7.20 (m, 3 H), 3.23-4.2 (m, 5H), 2.53 (s, 3H), 2.3-2.4 (m, 1H), 0.76-1.54 (m, 1H).<br>5-bromo nicotinonitrile: 59 mg (1.5 eq.) Intermediate 17: 100 mg (1 eq.); FCC/SCX-2 | 90 mg (92%) |
| Intermediate 39 | 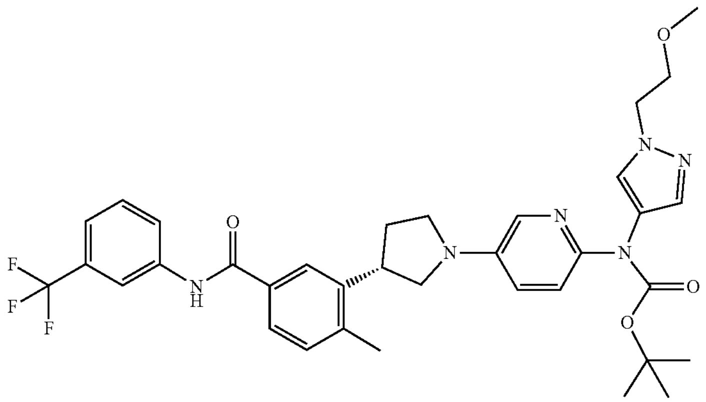 [SMILES: COCCn1cc(N(C(=O)OC(C)(C)C)c2ccc(N3CC[C@@H](c4cc(C(=O)Nc5cccc(C(F)(F)F)c5)ccc4C)C3)cn2)cn1]<br>LC-MS (ESI): method 1 $t_R$ = 1.33 min; m/z (M + 1) = 665.48<br>Intermediate 31: 65 mg (1.5 eq.): Intermediate 17: 57 mg (1 eq.); FCC/SCX-2 | 53 mg (49%) |

-continued

| Compound No | Structure Analytical Data/Amount reagents/Purification | Product Amount (Yield) |
|---|---|---|
| Intermediate 40 | 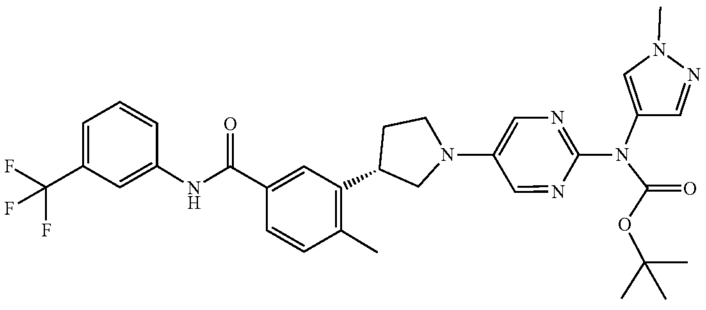 [SMILES: Cc1ccc(C(=O)Nc2cccc(C(F)(F)F)c2)cc1[C@@H]1CCN(c2cnc(N(C(=O)OC(C)(C)C)c3cnn(C)c3)nc2)C1] LC-MS (ESI): method 1 $t_R$ = 1.26 min; m/z (M + 1) = 622.16 Intermediate 30: 65 mg (1.5 eq.): Intermediate 17: 100 mg (1 eq.); FCC | 60 mg (34%) |
| Intermediate 41 | 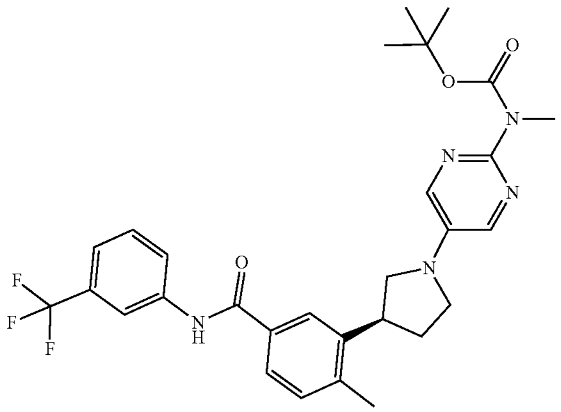 LC-MS (ESI): method 1 $t_R$ = 1.26 min; m/z (M + 1) = 566.09 Intermediate 32: 0.124 g (1.5 eq.) Intermediate 17: 100 mg (1 eq.); FCC/SCX-2 | 60 mg (38%) |

Example 17: preparation of 5-(3-(2-methyl-5-((3-(trifluoromethyl)phenyl)carbamoyl)phenyl)pyrrolidin-1-yl)nicotinamide

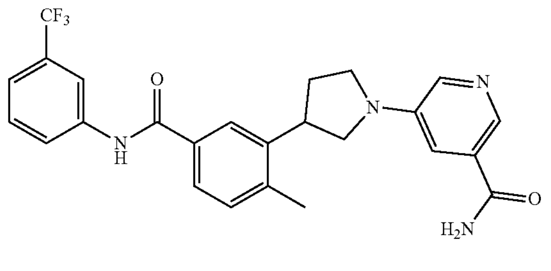 [SMILES: Cc1ccc(C(=O)Nc2cccc(C(F)(F)F)c2)cc1C1CCN(c2cncc(C(N)=O)c2)C1]

Example 17

Step 1; 5-(3-(2-methyl-5-((3-(trifluoromethyl) phenyl) carbamoyl)phenyl) pyrrolidin-1-yl)nicotinamide Round bottom flask was charged with Example 4 (30 mg, 0.067 mmol) and $K_2CO_3$ (33.5 mg, 0.243 mmol), then flushed with argon. DMSO (0.50 ml) was added, followed by dropwise addition of $H_2O_2$ 30 wt % in water (8.99 μl, 0.088 mmol). Reaction mixture was stirred at rt for 2 h. Water (10 mL) and AcOEt (15 mL) were added and reaction was stirred for 15 min., layers were separated and aqueous layer was extracted again with AcOEt (2×10 mL). The organics were combined, dried over $Na_2SO_4$ and concentrated. The crude material was purified via FCC on a silica gel (DCM/MeOH from 100:7 to 10:1) to provide the title product that was purified again on FCC (NH column 28 g, DCM/MeOH 95:5) to give title compound (9 mg, 0.019 mmol, 28.8% yield).

$^1H$ NMR (acetone, 400 MHz) δ 9.83 (br s, 1H), 8.41 (br s, 1H), 8.27 (s, 1H), 8.0-8.2 (m, 3H), 7.83 (dd, J=1.8, 7.9 Hz, 1H), 7.52-7.60 (m, 2H), 7.3-7.5 (m, 3H), 6.72 (br s, 1H), 3.8-3.9 (m, 2H), 3.66 (dt, J=3.1, 8.8 Hz, 1H), 3.5-3.6 (m, 1H), 3.43 (t, J=8.7 Hz, 1H), 2.52 (s, 3H), 2.48 (ddd, J=3.1, 6.1, 12.5 Hz, 1H), 2.2-2.4 (m, 1H).

LC-MS ESI): method 4 $t_R$=6.08 min; m/z (M+1)=469.2

The following compounds were prepared as described for Example 17, step 1, applying the corresponding Intermediate, as single enantiomer or racemic mixture; such procedures may involve minor variations, for example reaction temperature, reagent/solvent amount, reaction time, work-up and chromatographic purification conditions (eg. Only SCX).

| Example No | Structure<br>Analytical Data/Amount reagents/Purification | Product Amount (Yield) |
|---|---|---|
| 18 | 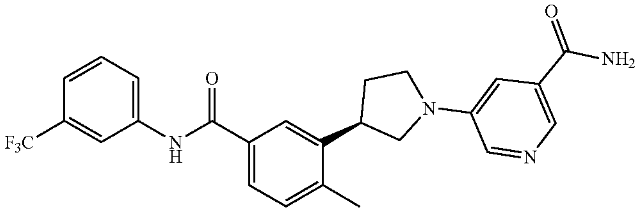 [SMILES: Cc1ccc(C(=O)Nc2cccc(C(F)(F)F)c2)cc1[C@H]1CCN(c2cncc(C(N)=O)c2)C1]<br>LC-MS (ESI): method 3 $t_R$ = 3.88 min; m/z (M + 1) = 469.10<br>$^1$H NMR (ACN-d3, 400 MHz) δ 8.93 (br s, 1H), 8.2-8.3 (m, 1H), 8.1-8.2 (m, 2H), 7.91 (br d, J = 8.1 Hz, 1H), 7.8-7.9 (m, 1H), 7.73 (dd, J = 1.5, 7.9 Hz, 1H), 7.54 (t, J = 8.0 Hz, 1H), 7.43 (br d, J = 7.9 Hz, 1H), 7.37 (d, J = 7.9 Hz, 1H), 7.28 (t, J = 2.0 Hz, 1H), 6.81 (br s, 1H), 6.02 (br s, 1H), 3.8-3.9 (m, 2H), 3.4-3.7 (m, 3H), 2.50 (s, 3H), 2.2-2.3 (m, 1H), 2.1-2.1 (m, 1H).<br>Intermediate 18: 33 mg; SCX | 27 mg (77%) |
| 19 | 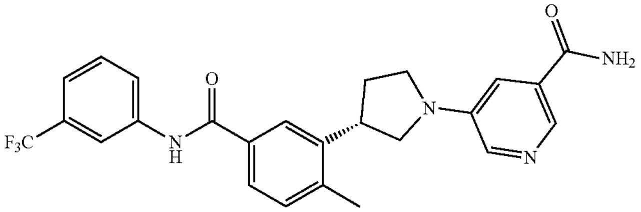 [SMILES: Cc1ccc(C(=O)Nc2cccc(C(F)(F)F)c2)cc1[C@@H]1CCN(c2cncc(C(N)=O)c2)C1]<br>LC-MS (ESI): method 3 $t_R$ = 3.88 min; m/z (M + 1) = 469.10<br>$^1$H NMR (ACN-d3, 400 MHz) δ 8.93 (br s, 1H), 8.2-8.3 (m, 1H), 8.1-8.2 (m, 2H), 7.91 (br d, J = 8.1 Hz, 1H), 7.8-7.9 (m, 1H), 7.73 (dd, J = 1.5, 7.9 Hz, 1H), 7.54 (t, J = 8.0 Hz, 1H), 7.43 (br d, J = 7.9 Hz, 1H), 7.37 (d, J = 7.9 Hz, 1H), 7.28 (t, J = 2.0 Hz, 1H), 6.81 (br s, 1H), 6.02 (br s, 1H), 3.8-3.9 (m, 2H), 3.4-3.7 (m, 3H), 2.50 (s, 3H), 2.2-2.3 (m, 1H), 2.1-2.1 (m, 1H).<br>Intermediate 19: 57 mg; Precipitation from water | 21 mg (36%) |
| 53 | 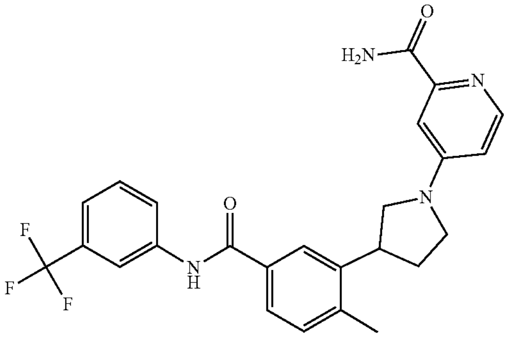 [SMILES: Cc1ccc(C(=O)Nc2cccc(C(F)(F)F)c2)cc1C1CCN(c2ccnc(C(N)=O)c2)C1]<br>LC-MS (ESI): method 4 $t_R$ = 5.50 min; m/z (M + 1) = 469.20<br>$^1$H NMR (MeOH-d4, 400 MHz) δ 8.30 (br s, 1H), 8.09-8.13 (m, 2H), 7.8-7.9 (m, 2H), 7.74 (br d, 1H, J = 7.9 Hz), 7.51 (t, 1H, J = 7.9 Hz), 7.3-7.4 (m, 3H), 6.74 (br s, 1H), 3.90 (br s, 2H), 3.72 (br s, 1H), 3.5-3.7 (m, 2H), 2.42-2.55 (m, 4H), 2.2-2.4 (m, 1H)<br>Example 24: 80 mg; FCC | 10 mg (12%) |

Example 47: preparation of (S)-3-(1-(6-((1-(2-methoxyethyl)-1H-pyrazol-4-yl)amino)pyridin-3-yl)pyrrolidin-3-yl)-4-methyl-N-(3-(trifluoromethyl)phenyl)benzamide

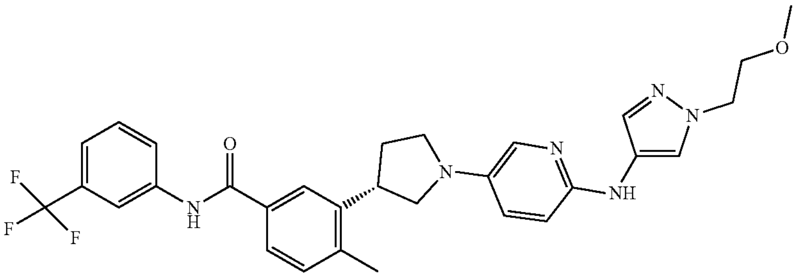 [SMILES: COCCn1cc(Nc2ccc(N3CC[C@@H](c4cc(C(=O)Nc5cccc(C(F)(F)F)c5)ccc4C)C3)cn2)cn1]

Example 47

Intermediate 39 (53 mg, 0.080 mmol) was dissolved in trifluoroacetic acid (1 ml, 12.98 mmol) and mixture was stirred for 1 h at rt. NaOH 2M (7.5 mL) and DCM were added. Organic layer was separated and dried over $Na_2SO_4$. After evaporation the title compound was obtained (33 mg, 0.06 mol, 73% yield).

$^1$H NMR (DMSO-d6, 400 MHz) δ 10.38 (s, 1H), 8.18 (s, 1H), 8.12 (s, 1H), 8.00 (br d, 1H, J=8.1 Hz), 7.90 (d, 1H, J=1.5 Hz), 7.84 (s, 1H), 7.75 (dd, 1H, J=1.8, 7.9 Hz), 7.5-7.6 (m, 2H), 7.40 (d, 1H, J=7.7 Hz), 7.3-7.4 (m, 2H), 6.99 (dd, 1H, J=2.8, 9.0 Hz), 6.59 (d, 1H, J=8.8 Hz), 4.14 (t, 1H, J=5.4 Hz), 3.6-3.7 (m, 1H), 3.6-3.6 (m, 3H), 3.38-3.48 (m, 1H), 3.30-3.35 (m, 1H), 3.2-3.3 (m, 1H), 3.19 (s, 3H), 2.43 (s, 3H), 2.3-2.4 (m, 1H), 2.0-2.2 (m, 1H)

LC-MS (ESI): method 4 $t_R$=6.59 min; m/z (M+1)=565.3

The following compounds were prepared following the procedure of Example 47 by starting from the corresponding protected intermediate.

Example 49: preparation of (S)-4-methyl-3-(1-(2-(methylamino)pyrimidin-5-yl)pyrrolidin-3-yl)-N-(3-(trifluoromethyl)phenyl)benzamide

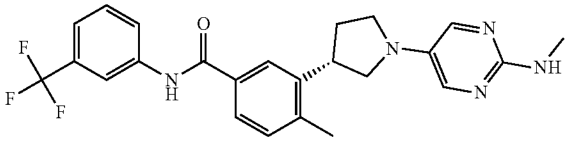

Example 49

Intermediate 41 (60 mg, 0.108 mmol) was dissolved in 1 mL of HCl 4M in dioxane and stirred on at rt.

The crude was evaporated until dryness, dissolved in 1 mL of MeOH (+20% DMSO) and purified by preparative HPLC. The relevant fractions were collected and charged

| Example No | Structure<br>Analytical Data/Amount reagents | Product Amount (Yield) |
|---|---|---|
| 48 | 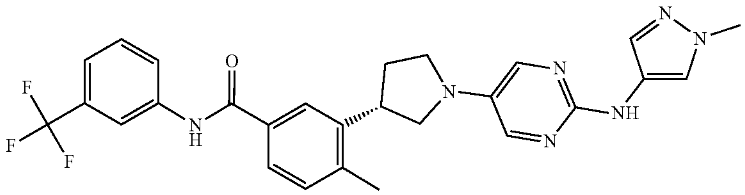 [SMILES: Cc1ccc(C(=O)Nc2cccc(C(F)(F)F)c2)cc1[C@@H]1CCN(c2cnc(Nc3cnn(C)c3)nc2)C1]<br>LC-MS (ESI): Method 4 $t_R$ = 7.7 m/z (M + 1) = 522.30<br>$^1$H NMR (acetone, 400 MHz) δ 9.74 (br s, 1H), 8.27 (s, 1H), 8.0-8.1 (m, 2H), 7.98 (s, 2H), 7.89 (s, 2H), 7.82 (dd, 1H, J = 1.8, 7.9 Hz), 7.56 (t, 1H, J = 8.0 Hz), 7.46 (s, 1H), 7.42 (d, 1H, J = 7.9 Hz), 7.37 (d, 1H, J = 7.9 Hz), 3.88 (dd, 1H, J = 7.6, 9.1 Hz), 3.81 (s, 3H), 3.72 (t, 1H, J = 8.3 Hz), 3.57 (dt, 1H, J = 3.5, 8.6 Hz), 3.3-3.5 (m, 2H), 2.51 (s, 3H), 2.48 (ddd, 1H, J = 3.6, 7.1, 8.6 Hz), 2.2-2.3 (m, 1H)<br>Intermediate 40: 60 mg (1.0 eq.) TFA: 0.0037 mL (5 eq.) | 21 mg (42%) |

over SCX column, washed with MeOH and the product was eluted with methanolic ammonia. The solution was dried to afford the desired product (13.2 mg, 0.029 mmol, 10.1% yield).

$^1$H NMR (ACN-d3, 400 MHz) δ 8.88 (br s, 1H), 8.16 (s, 1H), 7.9-7.9 (m, 3H), 7.84 (d, 1H, J=2.0 Hz), 7.71 (dd, 1H, J=2.0, 7.9 Hz), 7.55 (t, 1H, J=8.0 Hz), 7.43 (d, 1H, J=7.7 Hz), 7.35 (d, 1H, J=7.9 Hz), 5.00 (br d, 1H, J=4.2 Hz), 3.8-3.9 (m, 1H), 3.6-3.7 (m, 1H), 3.3-3.5 (m, 3H), 2.84 (d, 3H, J=5.0 Hz), 2.48 (s, 3H), 2.4-2.5 (m, 1H), 2.1-2.2 (m, 1H).

LC-MS ESI): method 4 $t_R$=7.36 min; m/z (M+1)=456.3

Example 50: preparation of (S)-3-(1-(6-aminopyridin-3-yl)pyrrolidin-3-yl)-4-methyl-N-(3-(trifluoromethyl)phenyl)benzamide

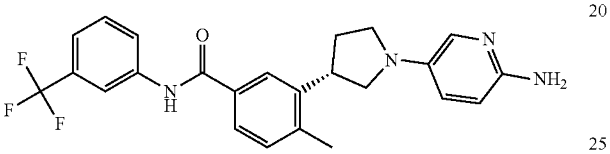

Example 50

Intermediate 38 (89 mg, 0.189 mmol), ammonium chloride (364 mg, 6.81 mmol) and iron (127 mg, 2.270 mmol) were dissolved in 2-propanol (2 mL) and water (1.0 mL). Reaction mixture was stirred for 1 h at 80° C. Then it was diluted in EtOAc and washed with $NaHCO_3$ sat. solution. Organic phase was evaporated under vacuum. Purification by FCC Reversed phase gave desired product (24 mg, 0.054 mmol, 29%).

$^1$H NMR (acetone, 400 MHz) δ 9.72 (br s, 1H), 8.25 (s, 1H), 8.0-8.0 (m, 2H), 7.79 (br d, 1H, J=8.1 Hz), 7.55 (t, 1H, J=8.0 Hz), 7.47 (d, 1H, J=2.4 Hz), 7.40 (br d, 1H, J=7.7 Hz), 7.34 (d, 1H, J=7.9 Hz), 6.91 (dd, 1H, J=2.7, 8.9 Hz), 6.50 (d, 1H, J=8.8 Hz), 4.59 (br s, 1H), 3.8-3.9 (m, 1H), 3.61 (t, 1H, J=8.2 Hz), 3.47 (dt, 1H, J=3.4, 8.5 Hz), 3.3-3.4 (m, 1H), 3.27 (t, 1H, J=8.3 Hz), 2.49 (s, 3H), 2.4-2.5 (m, 1H), 2.1-2.2 (m, 1H).

LC-MS ESI): method 4 $t_R$=6.0 min; m/z (M+1)=441.3

Example 51: Preparation of (S)-3-(1-(2-acetamidopyrimidin-5-yl)pyrrolidin-3-yl)-4-methyl-N-(3-(trifluoromethyl)phenyl)benzamide

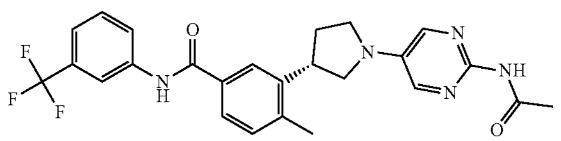 [SMILES: CC(=O)Nc1ncc(N2CC[C@@H](c3cc(C(=O)Nc4cccc(C(F)(F)F)c4)ccc3C)C2)cn1]

Example 51

Example 50 (40 mg, 0.091 mmol) was dissolved in DCM (3 ml) then DIPEA (0.047 ml, 0.272 mmol) and acetyl chloride (7.11 mg, 0.091 mmol) were added. The mixture was stirred at rt overnight.

The solution was washed with sat sol $NH_4Cl$, sat sol. of $NaHCO_3$ and brine. The organic layer was dried over $Na_2SO_4$, filtered and evaporated under vacuum. The crude product was purified by reverse phase FCC, then the relevant fractions were basified until pH 8-9 and the product was extracted with DCM to afford title compound (11.1 mg, 0.023 mmol, 25.3% yield).

$^1$H NMR (ACN-d3, 400 MHz) δ 8.90 (br s, 1H), 8.33 (br s, 1H), 8.16 (s, 1H), 8.04 (s, 2H), 7.91 (br d, 1H, J=8.1 Hz), 7.84 (s, 1H), 7.73 (br d, 1H, J=7.7 Hz), 7.55 (t, 1H, J=8.0 Hz), 7.3-7.5 (m, 2H), 3.3-3.9 (m, 5H), 2.49 (s, 3H), 2.4-2.5 (m, 1H), 2.2-2.3 (m, 1H), 2.14 (s, 3H)

LC-MS ESI): method 4 $t_R$=6.6 min; m/z (M+1)=484.3

Example 52: preparation of (S)-4-methyl-3-(1-(5-(1-methyl-1H-pyrazol-4-yl)pyridin-3-yl)pyrrolidin-3-yl)-N-(3-(trifluoromethyl)phenyl)benzamide

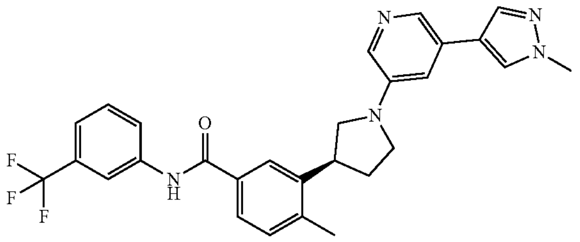 [SMILES: Cc1ccc(C(=O)Nc2cccc(C(F)(F)F)c2)cc1[C@@H]1CCN(c2cncc(-c3cnn(C)c3)c2)C1]

Example 52

A vial was loaded with $K_3PO_4$ (211 mg, 0.993 mmol), Example 62 (167 mg, 0.331 mmol), 1-methyl-4-(4,4,5,5-tetramethyl-1,3,2-dioxaborolan-2-yl)-1H-pyrazole (152 mg, 0.73 mmol), Pd-170 (11.15 mg, 0.017 mmol), THE (2 ml) and water (2.0 ml). Solution was backfilled with Ar and then solution was stirred for 1 h at 50° C. The solution was filtered, diluted with EtOAc and washed with $NaHCO_3$ sat solution.

$^1$H NMR (DMSO-d6, 400 MHz) δ 10.38 (s, 1H), 8.1-8.2 (m, 2H), 8.07 (d, 1H, J=1.8 Hz), 8.00 (d, 1H, J=8.6 Hz), 7.93 (d, 1H, J=1.8 Hz), 7.89 (s, 1H), 7.81 (d, 1H, J=2.9 Hz), 7.77 (dd, 1H, J=1.8, 7.9 Hz), 7.55 (t, 1H, J=8.0 Hz), 7.40 (d, 1H, J=7.7 Hz), 7.35 (d, 1H, J=8.1 Hz), 7.07 (t, 1H, J=2.2 Hz), 3.82 (s, 3H), 3.7-3.8 (m, 2H), 3.5-3.6 (m, 1H), 3.4-3.5 (m, 1H), 3.3-3.4 (m, 1H), 2.45 (s, 3H), 2.3-2.4 (m, 1H), 2.2-2.3 (m, 1H)

LC-MS ESI): method 4 $t_R$=6.4 min; m/z (M+1)=506.4

Example 54 and Example 55: preparation of 4-(3-(2-methyl-5-((3-(trifluoromethyl)phenyl)carbamoyl)phenyl)pyrrolidin-1-yl)picolinamide—first eluting and second eluting isomers Example 54

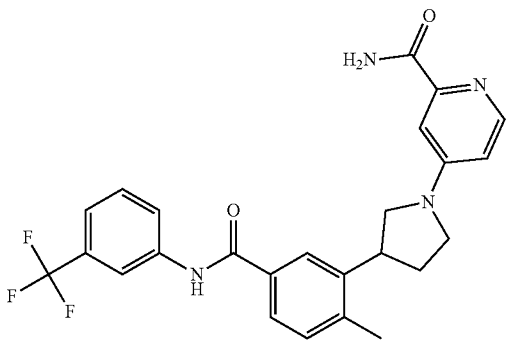

(First eluting)

Example 55

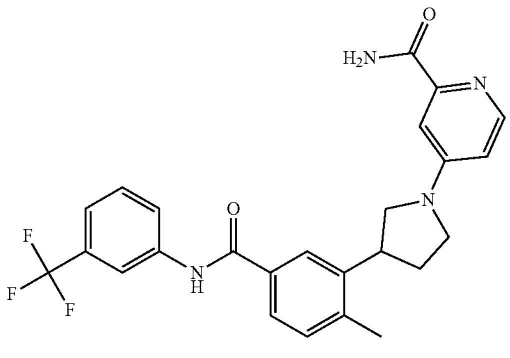

(Second eluting)

The isomers of racemic mixture of Example 53 (10 mg) were separated by chiral SFC. Combined fractions of single enantiomer were then evaporated to near dryness using a rotary evaporator, then in a vacuum oven, to afford the two single enantiomers.

Example 54

First eluting isomer (1.0 mg, 2.10 μmol, 10%).

LC-MS (ESI): Method 8 $t_R$=4.95 min; m/z (M+1)=469.4

Chiral analysis (SFC Method 10): $t_R$ 2.36 min, ee 100%

$^1$H NMR (400 MHz, DMSO) δ 10.41 (s, 1H), 8.19 (s, 1H), 8.15 (d, J=5.8 Hz, 1H), 8.03 (d, J=8.6 Hz, 1H), 7.97 (d, J=3.3 Hz, 1H), 7.93 (d, J=1.5 Hz, 1H), 7.79 (dd, J=1.8, 7.8 Hz, 1H), 7.58 (t, J=7.8 Hz, 1H), 7.49-7.42 (m, 2H), 7.38 (d, J=8.1 Hz, 1H), 7.21 (d, J=2.5 Hz, 1H), 6.68 (dd, J=2.5, 5.8 Hz, 1H), 3.86-3.78 (m, 2H), 3.65-3.60 (m, 1H), 3.53-3.42 (m, 2H), 2.47 (s, 3H), 2.45-2.37 (m, 1H), 2.26-2.19 (m, 1H).

Example 55

Second eluting isomer (1.0 mg, 2.10 μmol, 10%).

LC-MS (ESI): Method 9 $t_R$=3.80 min; m/z (M+1)=469.5

Chiral analysis (SFC Method 10): $t_R$ 3.61 min, ee 99.78%

$^1$H NMR (400 MHz, DMSO) δ 10.41 (s, 1H), 8.19 (s, 1H), 8.15 (d, J=5.6 Hz, 1H), 8.02 (d, J=8.3 Hz, 1H), 7.97 (d, J=2.8 Hz, 1H), 7.93 (d, J=1.5 Hz, 1H), 7.79 (dd, J=1.6, 7.7 Hz, 1H), 7.59 (t, J=8.0 Hz, 1H), 7.49-7.42 (m, 2H), 7.38 (d, J=7.8 Hz, 1H), 7.21 (d, J=2.5 Hz, 1H), 6.67 (dd, J=2.4, 5.7 Hz, 1H), 3.87-3.78 (m, 2H), 3.68-3.40 (m, 3H), 2.47 (s, 3H), 2.45-2.35 (m, 1H), 2.26-2.19 (m, 1H).

Example 56: preparation of (S)-5-(3-(2-methyl-5-((4-(morpholinomethyl)-3-(trifluoromethyl)phenyl)carbamoyl)phenyl)pyrrolidin-1-yl)nicotinamide

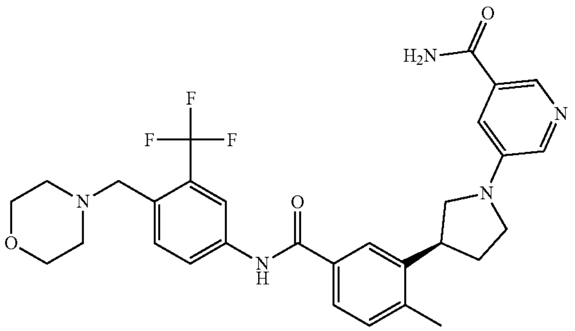 [SMILES: Cc1ccc(C(=O)Nc2ccc(CN3CCOCC3)c(C(F)(F)F)c2)cc1[C@@H]1CCN(c2cncc(C(N)=O)c2)C1]

Example 56

Step 1; Ethyl 4-methyl-3-vinylbenzoate (Intermediate 42)

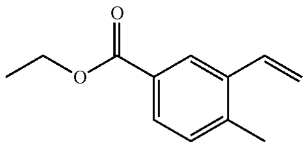

Intermediate 42 was prepared following the procedure of Intermediate 10, starting from ethyl 3-bromo-4-methylbenzoate (100 g, 411 mmol). After purification via FCC on silica gel, the title compound was obtained (61.5 g, 323 mmol, 79% yield) LC-MS (ESI): (Method 2) $t_R$=2.23 min; m/z (M+1)=190.9

$^1$H NMR (CHLOROFORM-d, 400 MHz) δ 8.15 (s, 1H), 7.84 (dd, 1H, J=1.5, 7.9 Hz), 7.22 (d, 1H, J=7.9 Hz), 6.94 (dd, 1H, J=11.0, 17.5 Hz), 5.7-5.8 (m, 1H), 5.38 (dd, 1H, J=0.9, 11.0 Hz), 4.39 (q, 2H, J=7.0 Hz), 2.40 (s, 3H), 1.41 (t, 3H, J=7.1 Hz)

Step 2; Ethyl 3-(1-benzylpyrrolidin-3-yl)-4-methylbenzoate (Intermediate 43)

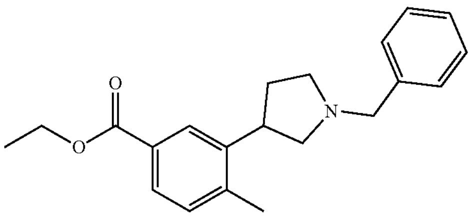 [SMILES: CCOC(=O)c1ccc(C)c(C2CCN(Cc3ccccc3)C2)c1]

Intermediate 43 was prepared following the procedure of Intermediate 11, starting from Intermediate 42 (78.4 μg, 412 μmmol) and N-benzyl-1-methoxy-N-((trimethylsilyl) methyl)methanamine (73.4 g, 309 mmol). The solvent was removed under vacuum and the crude was used in the next step without further purification.

LC-MS (ESI): (Method 2) $t_R$=1.07 min; m/z (M+1)=324.0

Step 3; Ethyl 4-methyl-3-(pyrrolidin-3-yl)benzoate (Intermediate 44)

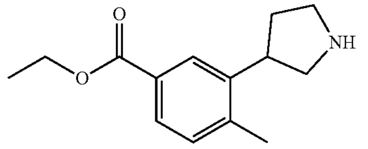 [SMILES: CCOC(=O)c1ccc(C)c(C2CCNC2)c1]

A 1 L reactor was purged with nitrogen and charged with palladium/C 10 (50% wet) (21.88 g, 10.28 mmol). The system was purged once more with nitrogen and placed under vacuum. A solution of Intermediate 43 (133 g, 411 mmol) in EtOH (500 ml) was then charged. The solution was then placed under an atmosphere of hydrogen (4 bar) and warmed to 60° C. and stirred for 8 h. The reaction mixture was filtered through celite and concentrated, then the crude was dissolved in $Et_2O$ and extracted with HCL 1N in quantitative yield.

LC-MS (ESI): (Method 2) $t_R$=0.69 min; m/z (M+1)=233.9

$^1$H NMR (CHLOROFORM-d, 400 MHz) δ 7.91 (s, 1H), 7.79 (dd, 1H, J=1.5, 7.9 Hz), 7.22 (d, 1H, J=7.6 Hz), 4.37 (q, 2H, J=7.0 Hz), 3.4-3.5 (m, 1H), 3.4-3.4 (m, 1H), 3.31 (ddd, 2H, J=4.6, 8.6, 11.0 Hz), 3.17 (td, 1H, J=7.6, 11.0 Hz), 2.93 (dd, 1H, J=8.1, 10.7 Hz), 2.42 (s, 3H), 2.2-2.3 (m, 1H), 1.9-2.0 (m, 1H), 1.40 (t, 3H, J=7.1 Hz)

Step 4; tert-butyl 3-(5-(ethoxycarbonyl)-2-methylphenyl)pyrrolidine-1-carboxylate (Intermediate 45)

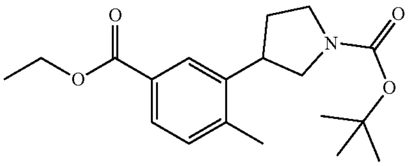 [SMILES: CCOC(=O)c1ccc(C)c(C2CCN(C(=O)OC(C)(C)C)C2)c1]

Intermediate 45 was prepared following the procedure of Intermediate 13, starting from Intermediate 44 (20.35 g, 87 mmol). After purification via silica gel FCC the title compound was obtained (24.5 g, 73.5 mmol, 84% yield).

LC-MS (ESI): (Method 1) $t_R$=1.35 min; m/z (M+1-tBu): 277.9

Step 5; tert-butyl (R)-3-(5-(ethoxycarbonyl)-2-methylphenyl)pyrrolidine-1-carboxylate (Intermediate 46a) and tert-butyl (S)-3-(5-(ethoxycarbonyl)-2-methylphenyl)pyrrolidine-1-carboxylate (Intermediate 46b)

Intermediate 45 as racemic mixture (20.1 g, 0.060 mol) was dissolved to 90 mg/mL in MeOH and was then purified by SFC, following Method 11. Combined fractions of each of first eluting (Intermediate 46a) and second eluting (Intermediate 46b) were then evaporated to near dryness using a rotary evaporator. The resultant solids were then transferred into final vessels with DCM which was removed under a stream of compressed air at 35° C. before being stored in a vacuum oven at 35° C. and 5 mbar until constant weight.

First Eluting Enantiomer (Intermediate 46a)

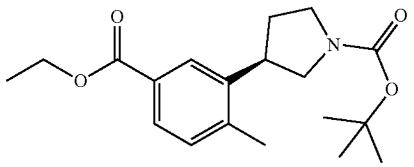 [SMILES: CCOC(=O)c1ccc(C)c([C@H]2CCN(C(=O)OC(C)(C)C)C2)c1]

Amount: 9.6 g PGP116,$C_1$

Chiral analysis (SFC Method 12): $t_R$ 1.238 min, ee 100%

LC-MS (ESI): Method 7 $t_R$=1.723 min; m/z (M+1-tBu)=278.2

Second Eluting Enantiomer (Intermediate 46b)

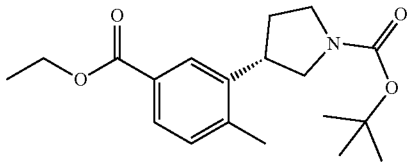 [SMILES: CCOC(=O)c1ccc(C)c([C@@H]2CCN(C(=O)OC(C)(C)C)C2)c1]

Amount: 9.2 g

Chiral analysis (SFC Method 12): $t_R$ 1.562 min, ee 100%

LC-MS (ESI): Method 7 $t_R$=1.722 min; m/z (M+1-tBu) =278.2

Intermediates 14 and 15 were synthesized starting from Intermediate 46a and 46b, respectively, under no racemizing conditions. Absolute configurations of Intermediates 14 and 15 were determined by IR and VCD Spectroscopy (see Example 15 and 16), therefore absolute configurations of Intermediates 46a and 46b were distinctively assigned.

Step 5; ethyl (S)-4-methyl-3-(pyrrolidin-3-yl)benzoate (Intermediate 47)

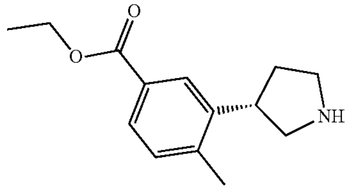 [SMILES: CCOC(=O)c1ccc(C)c([C@@H]2CCNC2)c1]

Intermediate 47 was prepared following the procedure of Intermediate 16, starting from Intermediate 46b (4.800 g, 14.40 mmol) to give desired product (3.40 g, 14.57 mmol, 100% yield).

LC-MS (ESI): Method 1 $t_R$=0.5 min; m/z (M+1)=234.1

Step 6; ethyl (S)-3-(1-(5-cyanopyridin-3-yl)pyrrolidin-3-yl)-4-methylbenzoate (Intermediate 48)

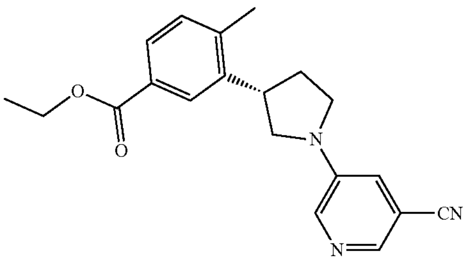 [SMILES: CCOC(=O)c1ccc(C)c([C@@H]2CCN(c3cncc(C#N)c3)C2)c1]

Intermediate 48 was prepared by following the procedure of Example 5, step 6 starting from Intermediate 47 (3.4 g, 14.57 mmol) and 5-bromonicotinonitrile (4.00 g, 21.86 mmol). Purification by FCC (0-40% EtOAc in Heptane) provided title compound (3.3 g, 9.84 mmol, 68% yield).

LC-MS (ESI): Method 1 $t_R$=1.2 min; m/z (M+1)=336.0

Step 7; ethyl (S)-3-(1-(5-carbamoylpyridin-3-yl) pyrrolidin-3-yl)-4-methylbenzoate (Intermediate 49)

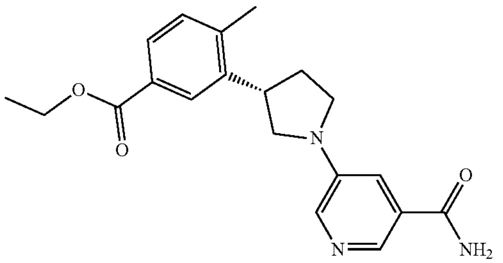 [SMILES: CCOC(=O)c1ccc(C)c([C@@H]2CCN(c3cncc(C(N)=O)c3)C2)c1]

Intermediate 49 was prepared by following the procedure of Example 17 starting from Intermediate 48 (2 g, 5.96 mmol). The reaction was quenched with water then the precipitated white solid was filtered, washed with water and dried overnight to obtain desired product (2.14 g, 6.06 mmol, 100% yield).

$^1$H NMR (400 MHz, DMSO-d6) δ ppm 1.23 (t, J=7.13 Hz, 3H) 2.04-2.17 (m, 1H) 2.36-2.44 (m, 1H) 2.46 (s, 3H) 3.34 (br d, J=2.41 Hz, 1H) 3.41-3.55 (m, 2H) 3.73-3.82 (m, 2H) 4.24 (q, J=7.09 Hz, 2H) 7.33-7.35 (m, 1H) 7.37 (s, 1H) 7.45 (br s, 1H) 7.73 (dd, J=7.89, 1.75 Hz, 1H) 7.81 (d, J=1.53 Hz, 1H) 8.03 (br s, 1H) 8.10 (d, J=2.85 Hz, 1H) 8.32 (d, J=1.53 Hz, 1H) LC-MS (ESI): Method 1 $t_R$=0.69 min; m/z (M+1)=354.3

Step 8; (S)-5-(3-(2-methyl-5-((4-(morpholinomethyl)-3-(trifluoromethyl) phenyl)carbamoyl)phenyl) pyrrolidin-1-yl)nicotinamide (Example 56) 4-(morpholin-4-ylmethyl)-3-(trifluoromethyl)aniline (184 mg, 0.7 mmol) was dissolved in dry THE (5 ml) under nitrogen, the mixture was stirred at −78° C. for 15 min, then butyllithium 2.5M in hexanes (0.191 ml, 0.478 mmol) was added dropwise in 5 min and the reaction was stirred for 1 h at −78° C.

A solution of Intermediate 49 (50 mg, 0.14 mmol) in THE (5 ml) was added dropwise for 10 min, the temperature was increased at rt and the reaction was stirred for 1 h. Water was added to quench the reaction and the solvent was evaporated by reduced pressure. Solid was dissolved in EtOAc and washed with $NH_4Cl$ sat solution. Organic phase was evaporated under vacuum. After purification by FCC the relevant fractions were combined and loaded onto an Isolute SCX-2 cartridge, washed with MeOH and the product was eluted with 2N methanolic ammonia. The residue was concentrated in vacuo to afford title compound (16 mg, 0.028 mmol, 20% yield).

$^1$H NMR (DMSO-d6, 400 MHz) δ 10.35 (s, 1H), 8.3-8.3 (m, 1H), 8.13 (d, 1H, J=2.0 Hz), 8.07 (d, 1H, J=2.6 Hz), 7.9-8.0 (m, 2H), 7.90 (s, 1H), 7.74-7.78 (m, 1H), 7.68 (d, 1H, J=8.6 Hz), 7.42 (s, 1H), 7.3-7.4 (m, 2H), 3.7-3.8 (m, 2H), 3.3-3.6 (m, 13H), 2.1-2.4 (m, 5H)

LC-MS (ESI): Method 4 $t_R$=4.28 min; m/z (M+1)=568.3

The following compound was prepared following the procedure of Example 56, step 8, starting from corresponding amine.

| Example No | Structure<br>Analytical Data/Amount reagents/Purification | Product Amount (Yield) |
|---|---|---|
| 57 | 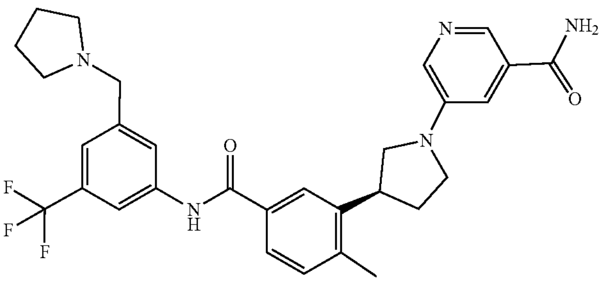 [SMILES: Cc1ccc(C(=O)Nc2cc(CN3CCCC3)cc(C(F)(F)F)c2)cc1[C@@H]1CCN(c2cncc(C(N)=O)c2)C1]<br>LC-MS (ESI): Method 4 $t_R$ = 4.6 m/z (M + 1) = 552.40<br>$^1$H NMR (DMSO-d6, 400 MHz) δ 10.36 (s, 1H), 8.28 (s, 1H), 8.1-8.2 (m, 1H), 8.08 (d, 1H, J = 2.6 Hz), 8.0-8.0 (m, 1H), 7.9-8.0 (m, 2H), 7.77 (d, 1H, J = 7.9 Hz), 7.43 (s, 1H), 7.35 (d, 1H, J = 8.1 Hz), 7.31 (bs, 2H), 3.7-3.8 (m, 2H), 3.2-3.7 (m, 5H), 2.2-2.5 (m, 7H), 1.67 (br s, 4H)<br>Intermediate 33: 156 mg (4.5 eq.) Intermediate 49: 50 mg (1.0 eq.);<br>FCC/SCX-2 | 40 mg (51%) |

Example 58: preparation of (S)-5-(3-(5-((4-((dimethylamino)methyl)-3-(trifluoromethyl)phenyl)carbamoyl)-2-methylphenyl)pyrrolidin-1-yl)nicotinamide

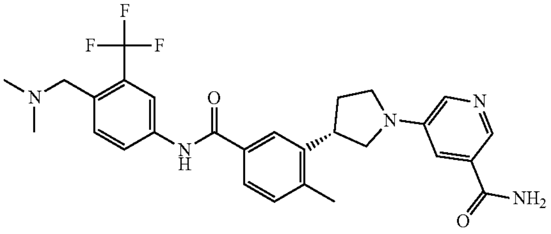 [SMILES: Cc1ccc(C(=O)Nc2ccc(CN(C)C)c(C(F)(F)F)c2)cc1[C@@H]1CCN(c2cncc(C(N)=O)c2)C1]

Example 58

Step 1; (S)-3-(1-(5-cyanopyridin-3-yl)pyrrolidin-3-yl)-N-(4-((dimethylamino) methyl)-3-(trifluoromethyl)phenyl)-4-methylbenzamide (Intermediate 50/Example 65)

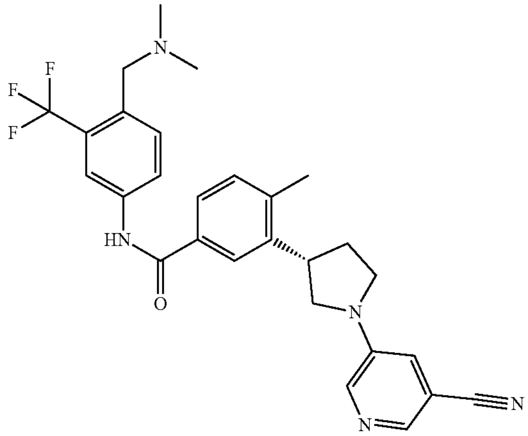 [SMILES: Cc1ccc(C(=O)Nc2ccc(CN(C)C)c(C(F)(F)F)c2)cc1[C@@H]1CCN(c2cncc(C#N)c2)C1]

4-[(dimethylamino)methyl]-3-(trifluoromethyl)aniline (195 mg, 0.89 mmol) was dissolved in dry THE (2 ml). The vial was purged and backfilled with argon. A solution of LiHMDS (1.118 ml, 1.118 mmol) was then added and the mixture stirred at rt for 6 h. Then Intermediate 48 (150 mg, 0.447 mmol) was dissolved in THE (2 ml) and added to the solution. Resulting solution was stirred on at rt. Solvent was evaporated and resulting solid was dissolved in EtOAc and washed with $H_2O$ or $NaHCO_3$ sat. solution. Purification on FCC gave desired product (126 mg, 0.25 mmol, 55% yield).

LC-MS (ESI): Method 1 $t_R$=0.75 min; m/z (M+1)=508.4

Step 2; (S)-5-(3-(5-((4-((dimethylamino)methyl)-3-(trifluoromethyl)phenyl) carbamoyl)-2-methylphenyl)pyrrolidin-1-yl)nicotinamide (Example 58)

Example 58 was prepared following the procedure of Intermediate 49 starting from Intermediate 50 (126 mg, 0.25 mmol). After precipitation from water and washing with ethyl ether, the desired product was obtained (77 mg, 0.147 mmol, 59% yield).

$^1$H NMR (DMSO-d6, 400 MHz) δ 10.35 (s, 1H), 8.28 (s, 1H), 8.13 (s, 1H), 8.07 (d, 1H, J=2.4 Hz), 8.0-8.0 (m, 2H), 7.91 (s, 1H), 7.76 (d, 1H, J=7.9 Hz), 7.65 (d, 1H, J=8.3 Hz), 7.43 (br s, 1H), 7.34 (d, 1H, J=7.9 Hz), 7.31 (br s, 1H), 3.76 (br d, 2H, J=4.4 Hz), 3.5-3.6 (m, 1H), 3.3-3.5 (m, 4H), 2.44 (s, 3H), 2.4-2.4 (m, 1H), 2.2-2.2 (m, 1H), 2.14 (s, 6H)

LC-MS (ESI): Method 4 $t_R$=4.57 min; m/z (M+1)=526.3

Example 59: Preparation of (S)-3-(1-(5-acetamidonicotinoyl)pyrrolidin-3-yl)-4-methyl-N-(3-(trifluoromethyl)phenyl)benzamide

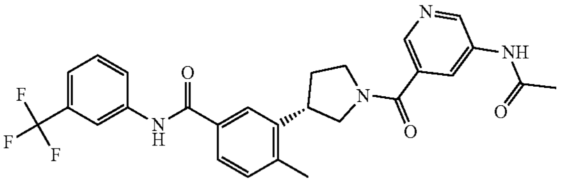 [SMILES: CC(=O)Nc1cncc(C(=O)N2CC[C@@H](c3cc(C(=O)Nc4cccc(C(F)(F)F)c4)ccc3C)C2)c1]

Example 59

Example 59 was prepared following procedure of Intermediate 3 starting from Intermediate 17 (100 mg, 0.287 mmol) and 5-acetamidonicotinic acid (130 mg, 0.722 mmol). The residue was purified via reverse phase FCC and charged over SCX column, washed with MeOH and eluted with methanolic ammonia to give the desired product (29.2 mg, 0.057 mmol, 20% yield).

$^1$H NMR (ACN-d3, 600 MHz) δ 8.8-8.9 (m, 2H), 8.59 (dd, 2H, J=2.1, 8.2 Hz), 8.47 (br s, 2H), 8.36 (s, 2H), 8.17 (s, 1H), 8.15 (s, 1H), 8.10 (br s, 2H), 7.87 (br d, 2H, J=8.2 Hz), 7.79 (s, 1H), 7.74 (s, 1H), 7.65 (d, 1H, J=7.8 Hz), 7.61 (d, 1H, J=8.0 Hz), 7.48 (dt, 2H, J=4.4, 7.9 Hz), 7.3-7.4 (m, 2H), 7.28 (d, 1H, J=7.6 Hz), 7.22 (d, 1H, J=7.9 Hz), 3.96 (dd, 1H, J=7.6, 12.0 Hz), 3.7-3.8 (m, 3H), 3.5-3.6 (m, 6H), 2.40 (s, 3H), 2.29 (s, 3H), 2.2-2.3 (m, 4H), 1.98 (s, 3H), 2.01 (s, 3H)

LC-MS (ESI): Method 4 $t_R$=6.25 min; m/z (M+1)=511.2

The following compound was prepared by following the procedure of Example 59 starting from the corresponding carboxylic acid.

| Example No | Structure Analytical Data/Amount reagents | Product Amount (Yield) |
|---|---|---|
| 60 | 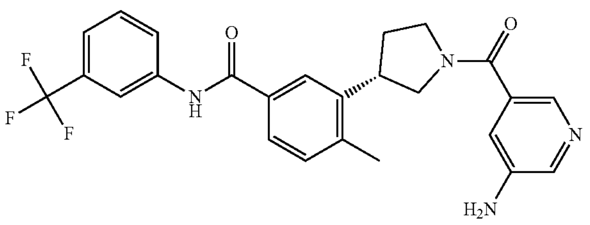 [SMILES: Cc1ccc(C(=O)Nc2cccc(C(F)(F)F)c2)cc1[C@@H]1CCN(C(=O)c2cncc(N)c2)C1] (S)-3-(1-(5-aminonicotinoyl)pyrrolidin-3-yl)-4-methyl-N-(3-(trifluoromethyl)phenyl)benzamide LC-MS (ESI): Method 4 $t_R$ = 5.68 min; m/z (M + 1) = 469.3 $^1$H NMR (ACN-d3, 400 MHz) δ 8.95 (br d, 2H, J = 8.3 Hz), 8.19 (s, 2H), 8.0-8.1 (m, 4H), 7.96 (d, 2H, J = 8.1 Hz), 7.87 (s, 1H), 7.81 (s, 1H), 7.7-7.8 (m, 2H), 7.57 (t, 2H, J = 7.9 Hz), 7.45 (br d, 2H, J = 7.9 Hz), 7.37 (d, 1H, J = 7.9 Hz), 7.32 (d, 1H, J = 7.9 Hz), 7.10 (t, 2H, J = 2.2 Hz), 4.01 (dd, 1H, J = 7.6, 11.7 Hz), 3.8-3.8 (m, 3H), 3.6-3.7 (m, 6H), 2.48 (s, 3H), 2.39 (s, 3H), 2.2-2.4 (m, 2H), 2.1-2.2 (m, 2H) 5-aminonicotinic acid: 48 mg (1.2 eq.) Intermediate 17: 100 mg (1.0 eq.) | 15 mg (11%) |

Comparative newly synthesized compounds, characterized by having an aziridinyl in place of a pyrrolidinyl ring (C1) or a —$CH_2$— linker between the pyrrolidinyl ring and group A (C2), were prepared as following:

Compound C1: Preparation of 4-methyl-3-(1-(pyridin-3-yl)aziridin-2-yl)-N-(3-(trifluoromethyl)phenyl)benzamide

C1

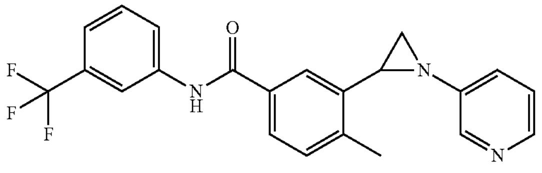

Step 1; 3-formyl-4-methyl-N-(3-(trifluoromethyl) phenyl)benzamide (Intermediate 20)

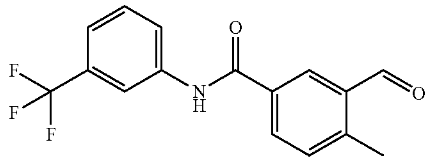 [SMILES: Cc1ccc(C(=O)Nc2cccc(C(F)(F)F)c2)cc1C=O]

Intermediate 10 (4.00 g, 13.10 mmol) was dissolved in EtOH (50 ml) then ozone (0.629 g, 13.10 mmol) was introduced at −78° C. ° C. After disappearance of SM in LC-MS, AcOH (3.23 ml, 56.3 mmol) and zinc (0.857 g, 13.10 mmol) were added, the reaction mixture was warmed to rt, and stirred for 1 h. After filtration and removal of the solvent, DCM and $H_2O$ were added. The organic layer was separated, dried over $Na_2SO_4$, and evaporated. Crude product was purified by FCC (gradient A:B from 100:0 to 50:50, eluent A:n-Heptane eluent B:Acetone) to afford title compound (2.3 g, 7.49 mmol, 57.1% yield).

Step 2; (E)-4-methyl-3-((pyridin-3-ylimino)methyl)-N-(3-(trifluoromethyl) phenyl)benzamide (Intermediate 21)

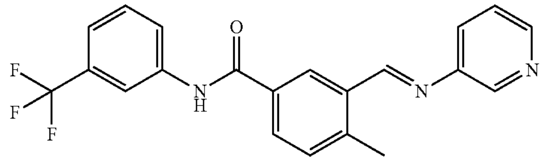 [SMILES: Cc1ccc(C(=O)Nc2cccc(C(F)(F)F)c2)cc1/C=N/c1cccnc1]

3-aminopyridine and Intermediate 20 (50 mg, 0.163 mmol) were dissolved in dry DCM (2.0 ml) and 2 drops of acetic acid (0.00 mmol) were added. Then Molecular sieves 4A were added and the reaction was stirred at 80° C. for 48 h. The crude was filtered and the solvent was evaporated under vacuum to afford title compound that was used in the next without further purification.

Step 3; 4-methyl-3-(1-(pyridin-3-yl)aziridin-2-yl)-N-(3-(trifluoromethyl) phenyl) benzamide (Compound C1)

A solution of the ylide was prepared under nitrogen from trimethylsulfoxonium iodide (48.1 mg, 0.219 mmol), sodium hydride (5.24 mg, 0.219 mmol), and dry DMSO (3 ml). With stirring, a solution of Intermediate 21 (69.8 mg, 0.182 mmol) in dry DMSO (3 ml) was added at RT, then the solution was stirred at rt for 1 h. and at 60° C. for 2 h. The crude was purified by direct phase FCC (gradient A:B from 100:0 to 60:40, eluent A:n-Heptane eluent B:Acetone) to afford title compound (58 mg, 0.146 mmol, 42.6%).

$^1$H NMR (CAN-d3, 400 MHz) δ 8.95 (br s, 1H), 8.44 (d, J=2.6 Hz, 1H), 8.23 (dd, J=1.3, 4.8 Hz, 1H), 8.16 (s, 1H), 7.98 (d, J=1.5 Hz, 1H), 7.93 (br d, J=8.1 Hz, 1H), 7.80 (dd, J=1.8, 7.9 Hz, 1H), 7.55 (t, J=8.0 Hz, 1H), 7.4-7.5 (m, 2H), 7.37 (d, J=7.9 Hz, 1H), 7.25 (dd, J=4.6, 8.1 Hz, 1H), 3.41 (dd, J=3.3, 6.6 Hz, 1H), 2.6-2.6 (m, 1H), 2.51 (s, 3H), 2.37 (dd, J=0.7, 3.3 Hz, 1H)

LC-MS (ESI): method 3 $t_R$=7.65 min; m/z (M+1)=398.2

Compound C2: 4-methyl-3-(1-(pyridin-3-ylmethyl)pyrrolidin-3-yl)-N-(3-(trifluoromethyl)phenyl)benzamide

C2

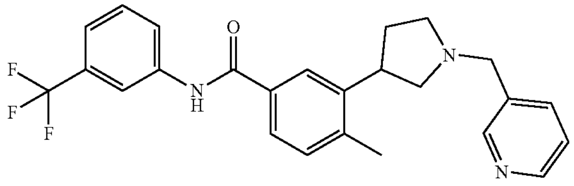

Intermediate 12 (50 mg, 0.144 mmol) was dissolved in DMF (1 ml) then 3-(bromo methyl)pyridine hydrobromide (37.0 mg, 0.215 mmol) and TEA (0.080 ml, 0.574 mmol) were added. The reaction was stirred at rt for 4 h. The crude was purified directly on reverse phase FCC (gradient A:B from 100:0 to 0:100. eluent A: $H_2O$:ACN:HCOOH 95:5:0.1 eluent B:$H_2O$:ACN:HCOOH 5:95:0.1). The relevant fractions were combined and loaded onto an Isolute SCX-2 cartridge, washed with MeOH and the product was eluted with 2N methanolic ammonia. The residue was concentrated in vacuo to afford the title compound (13 mg, 0.030 mmol, 20.6% yield).

$^1$H NMR (acetone, 400 MHz) δ 7.21-8.69 (m, 12H), 3.7-4.3 (m, 3H), 2.99-3.33 (m, 4H), 2.4-2.5 (m, 2H), 2.40 (s, 3H).

LC-MS (ESI): method 3 $t_R$=5.25 min; m/z (M+1)=440.2

Pharmacological Activity of the Compounds of the Invention

In vitro Assays

Binding Assays

DDR1 and DDR2 binding assays were performed using Life Technologies LanthaScreen™ Europium Kinase Binding assay. The compounds were incubated with 5 nM DDR1 (Carna Biosciences) or 5 nM DDR2 (Life Technologies) for 1 hour at rt in white 384-well OptiPlate (PerkinElmer), containing 20 nM or 10 nM Kinase Tracer 178 respectively and 2 nM Europium labelled anti-GST antibody (Life Technologies) in assay buffer (50 mM HEPES pH 7.5, 10 mM MgCI2, 1 mM EGTA and 0.01% BRIJ35). The ratio of fluorescence emission 665 nm/615 nm after excitation at 340 nm was obtained using the Tecan Spark 20M plate reader. IC50 values were determined in GraphPad Prism 7.0 software, using 4 parameter model: log(inhibitor) vs. response. IC50 values were converted in Ki using the Cheng-Prusoff equation (Ki=IC50/(1+[Tracer]/Kd).

The results for individual compounds are provided below in Table 5, wherein the compounds are classified in term of potency (nM) in binding with respect to their inhibitory activity on DDR1 and DDR2:

TABLE 5

| Example No. | Ki DDR1 | Ki DDR2 |
|---|---|---|
| 1 | +++ | +++ |
| 2 | +++ | +++ |
| 3 | +++ | +++ |
| 4 | ++ | + |
| 5 | +++ | + |
| 6 | +++ | +++ |
| 7 | +++ | +++ |
| 8 | +++ | + |
| 9 | +++ | ++ |
| 10 | +++ | ++ |
| 11 | +++ | ++ |
| 12 | +++ | ++ |
| 13 | ++ | + |
| 14 | +++ | +++ |
| 15 | ++ | + |
| 16 | +++ | +++ |
| 17 | +++ | ++ |
| 18 | +++ | ++ |
| 19 | +++ | +++ |
| 20 | +++ | +++ |
| 21 | +++ | + |
| 22 | +++ | ++ |
| 23 | +++ | +++ |
| 24 | + | − |
| 25 | +++ | +++ |
| 26 | +++ | +++ |
| 27 | +++ | + |
| 28 | +++ | ++ |
| 30 | +++ | ++ |
| 31 | +++ | − |
| 32 | + | − |
| 33 | +++ | ++ |
| 34 | +++ | +++ |
| 35 | +++ | +++ |
| 36 | +++ | + |
| 37 | +++ | ++ |
| 38 | +++ | ++ |
| 39 | ++ | − |
| 40 | +++ | +++ |
| 41 | +++ | +++ |
| 42 | ++ | + |
| 43 | + | + |
| 44 | ++ | + |
| 45 | +++ | ++ |
| 46 | +++ | ++ |
| 47 | ++ | + |
| 48 | +++ | +++ |
| 49 | +++ | ++ |
| 50 | +++ | + |
| 51 | +++ | ++ |
| 52 | +++ | +++ |
| 53 | +++ | +++ |
| 54 | +++ | +++ |
| 55 | ++ | + |
| 56 | +++ | ++ |
| 57 | +++ | +++ |
| 58 | +++ | ++ |

−: Ki higher than 60 nM
+: Ki between 25 and 60 nM
++: Ki between 25 nM and 10 nM
+++: Ki lower than 10 nM As it can be appreciated, the compounds of Table 5, i.e. the compounds of the invention, show a good activity as antagonist of DDR1 and DDR2. Accordingly, the compounds of the invention can be effectively used for treating disease, disorder or condition associated with DDR receptors, such as fibrosis, e.g. pulmonary fibrosis, idiopathic pulmonary fibrosis (IPF), hepatic fibrosis, renal fibrosis, ocular fibrosis, cardiac fibrosis, arterial fibrosis and systemic sclerosis.

Comparative Compounds

Compounds C1 and C2 were tested in the same binding assay described above.

TABLE 6

| Example No | DDR1 Ki (nM) | DDR2 Ki (nM) |
|---|---|---|
| C1 | 174 | 305 |
| C2 | 571 | 764 |

The compounds of the present invention, as shown in Table 5, have a binding affinity for DDR1 and DDR2 receptors expressed as Ki lower than 60 nM, and for most of the compounds lower than 25 nM or even lower than 10 nM, whereas comparative Compound C1 has a binding affinity higher than 170 nM on DDR1 receptor, even of 571 for C2, and higher than 300 on DDR2 receptor for C1, even of 764 for C2.

These data demonstrate that, conversely to the comparative Compound C1 characterized by having an aziridinyl in place of a pyrrolidinyl ring, the presence in the compounds of the present invention of a pyrrolidinyl ring, unexpectedly and remarkably determines a relevant increase in the inhibitory activity on the DDR1 and DDR2 receptors.

As a further evidence, conversely to comparative Compound C2, characterized by a —$CH_2$ linker between the pyrrolidinyl ring and group A, the absence of such linker in the present invention compounds, unexpectedly and noteworthy determines a relevant increase in the inhibitory activity against the DDR1 and DDR2 receptors.

The invention claimed is:

1. A compound of formula (I)

(I)

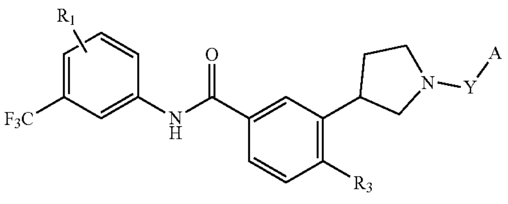

wherein

Y is absent or is —C(O)—;

$R_1$ is —($C_1$-$C_6$)alkylene-$NR_AR_B$ or hydrogen;

$R_3$ is —($C_1$-$C_4$)alkyl;

A is selected from the group consisting of A1, A2, A3

A1

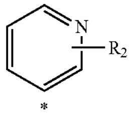

A2

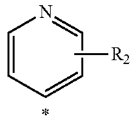

A3

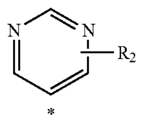

and bicyclic heteroaryl B, wherein * indicates the point of attachment to Y and B is substituted by $R_2$; wherein $R_2$ is H or selected from the group consisting of halogen, cyano, —$NR_AR_B$, —C(O)$NR_AR_B$, —C(O)$NR_C$—($C_1$-$C_6$)alkylene-$NR_AR_B$, —C(O)$NR_C$—($C_1$-$C_6$)alkylene-$OR_A$, —$NR_A$C(O)$R_B$, —$OR_A$, —$NR_C$—($C_1$-$C_6$)alkylene-$OR_A$, —$NR_C$—($C_1$-$C_6$) alkylene-$NR_AR_B$, —C(O)$NR_A$-heterocycloalkyl, heterocycloalkyl, —$NR_A$-heteroaryl, —($C_1$-$C_6$)alkylene-heterocycloalkyl, —($C_1$-$C_6$)alkylene-$OR_A$, —O—($C_1$-$C_6$)alkylene-$NR_AR_B$, —O—($C_1$-$C_6$)alkylene-$OR_A$, —O—($C_1$-$C_6$)alkylene-heterocycloalkyl, —($C_1$-$C_6$) haloalkyl and —($C_1$-$C_6$)alkyl;

$R_A$, $R_B$ and $R_C$ are independently —($C_1$-$C_6$)alkyl or hydrogen;

or $R_A$ and $R_B$ taken together with the nitrogen they are attached to may form a heterocycloalkyl;

and wherein each heterocycloalkyl or heteroaryl of $R_2$ is substituted by one or more substituents independently selected from the group consisting of hydrogen, halogen, —($C_1$-$C_6$)alkyl, —($C_1$-$C_6$) haloalkyl, —($C_1$-$C_6$)alkylene-$OR_A$, —$OR_A$, —O—($C_1$-$C_6$)alkylene-$NR_AR_B$ and —O—($C_1$-$C_6$)alkylene-$OR_A$;

or a pharmaceutically acceptable salt of said compound.

2. The compound of formula (I) or pharmaceutically acceptable salt thereof according to claim 1, wherein $R_1$ is hydrogen and $R_3$ is methyl, represented by formula (I)'

(I)

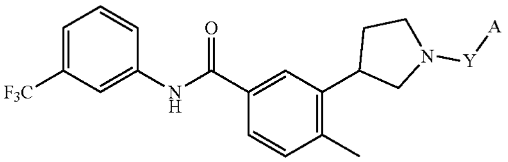

wherein

Y is absent or is —C(O)—;

A is selected from the group consisting of A1, A2 and A3

A1

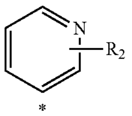

A2

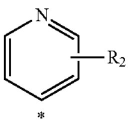

A3

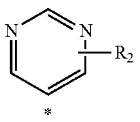

wherein * indicates the point of attachment to Y; and wherein $R_2$ is H or selected from the group consisting of halogen atoms, cyano, —C(O)$NH_2$, —C(O)NH—($C_1$-$C_6$)alkyl, —C(O)NH—($C_1$-$C_6$)alkylene-$NR_AR_B$, —C(O)NH—($C_1$-$C_6$)alkylene-$OR_A$, —NHC(O)$R_B$, —O—($C_1$-$C_6$) alkyl, —NH—($C_1$-$C_6$)alkylene-$OR_A$, —C(O)NH-heterocycloalkyl, heterocycloalkyl, —($C_1$-$C_6$)alkylene-heterocycloalkyl and —O—($C_1$-$C_6$)alkylene-heterocycloalkyl, wherein each of said heterocycloalkyl is optionally substituted by one or more-($C_1$-$C_6$)alkyl;

$R_A$ is —($C_1$-$C_6$)alkyl; and $R_B$ is —($C_1$-$C_6$)alkyl.

3. The compound of formula (I) or pharmaceutically acceptable salt thereof according to claim 1, wherein Y is absent and A is A1

A1

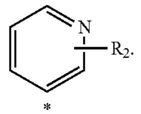

4. The compound of formula (I) or pharmaceutically acceptable salt thereof according to claim 1, wherein Y is —C(O)—and A is A1

A1

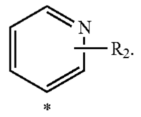

5. The compound of formula (I) or pharmaceutically acceptable salt thereof according to claim 1, wherein Y is absent and A is A2

A2

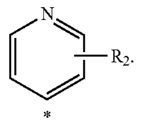

6. The compound of formula (I) or pharmaceutically acceptable salt thereof according to claim 1, wherein Y is absent and A is A3

A3

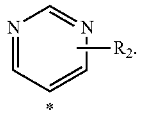

7. The compound of formula (I) or pharmaceutically acceptable salt thereof according to claim 1, wherein Y is absent and A is bicyclic heteroaryl B substituted by $R_2$.

8. The compound of formula (I) or pharmaceutically acceptable salt thereof according to claim 1, wherein the compound is selected from the group consisting of:

N-methyl-4-(3-(2-methyl-5-((3-(trifluoromethyl)phenyl) carbamoyl)phenyl) pyrrolidin-1-yl)picolinamide;

4-methyl-3-(1-(pyridin-3-yl)pyrrolidin-3-yl)-N-(3-(trifluoromethyl)phenyl) benzamide;

3-(1-(5-methoxypyridin-3-yl)pyrrolidin-3-yl)-4-methyl-N-(3-(trifluoromethyl)phenyl)benzamide;

3-(1-(5-cyanopyridin-3-yl)pyrrolidin-3-yl)-4-methyl-N-(3-(trifluoromethyl) phenyl)benzamide;

4-methyl-3-(1-(5-(2-morpholinoethoxy)pyridin-3-yl)pyrrolidin-3-yl)-N-(3-(trifluoromethyl)phenyl)benzamide;

4-methyl-3-(1-(5-(2-(4-methylpiperazin-1-yl)ethoxy) pyridin-3-yl)pyrrolidin-3-yl)-N-(3-(trifluoromethyl) phenyl)benzamide;

N-(2-(dimethylamino) ethyl)-5-(3-(2-methyl-5-((3-(trifluoromethyl) phenyl)carbamoyl)phenyl)pyrrolidin-1-yl)nicotinamide;

4-methyl-3-(1-(5-morpholinopyridin-3-yl)pyrrolidin-3-yl)-N-(3-(trifluoromethyl)phenyl)benzamide;

N-(2-methoxyethyl)-5-(3-(2-methyl-5-((3-(trifluoromethyl)phenyl) carbamoyl)phenyl)pyrrolidin-1-yl)nicotinamide;

N-methyl-5-(3-(2-methyl-5-((3-(trifluoromethyl)phenyl) carbamoyl) phenyl)pyrrolidin-1-yl)nicotinamide;

4-methyl-3-(1-(5-(morpholinomethyl)pyridin-3-yl)pyrrolidin-3-yl)-N-(3-(trifluoromethyl)phenyl)benzamide;

4-methyl-3-(1-(5-(4-methylpiperazin-1-yl)pyridin-3-yl) pyrrolidin-3-yl)-N-(3-(trifluoromethyl)phenyl)benzamide;

3-(1-(5-bromopyridin-3-yl)pyrrolidin-3-yl)-4-methyl-N-(3-(trifluoromethyl) phenyl)benzamide;

4-methyl-3-(1-nicotinoylpyrrolidin-3-yl)-N-(3-(trifluoromethyl)phenyl)benzamide;

(R)-4-methyl-3-(1-(pyridin-3-yl)pyrrolidin-3-yl)-N-(3-(trifluoromethyl) phenyl)benzamide;

(S)-4-methyl-3-(1-(pyridin-3-yl)pyrrolidin-3-yl)-N-(3-(trifluoromethyl) phenyl)benzamide;

5-(3-(2-methyl-5-((3-(trifluoromethyl)phenyl)carbamoyl) phenyl)pyrrolidin-1-yl)nicotinamide;

(R)-5-(3-(2-methyl-5-((3-(trifluoromethyl)phenyl)carbamoyl)phenyl)pyrrolidin-1-yl)nicotinamide;

(S)-5-(3-(2-methyl-5-((3-(trifluoromethyl)phenyl)carbamoyl)phenyl)pyrrolidin-1-yl)nicotinamide;

(S)-4-methyl-3-(1-(pyrimidin-5-yl)pyrrolidin-3-yl)-N-(3-(trifluoromethyl) phenyl)benzamide;

3-(1-(5-((2-(dimethylamino) ethyl) amino)pyridin-3-yl) pyrrolidin-3-yl)-4-methyl-N-(3-(trifluoromethyl)phenyl)benzamide;

4-methyl-3-(1-(5-((2-morpholinoethyl) amino)pyridin-3-yl)pyrrolidin-3-yl)-N-(3-(trifluoromethyl)phenyl)benzamide;

3-(1-(5-(2-(dimethylamino) ethoxy)pyridin-3-yl)pyrrolidin-3-yl)-4-methyl-N-(3-(trifluoromethyl)phenyl)benzamide;

3-(1-(2-cyanopyridin-4-yl)pyrrolidin-3-yl)-4-methyl-N-(3-(trifluoromethyl) phenyl)benzamide;

(S)—N-methyl-4-(3-(2-methyl-5-((3-(trifluoromethyl) phenyl)carbamoyl) phenyl)pyrrolidin-1-yl)picolinamide;

(S)—N-methyl-5-(3-(2-methyl-5-((3-(trifluoromethyl) phenyl)carbamoyl) phenyl)pyrrolidin-1-yl)nicotinamide;

(R)—N-methyl-4-(3-(2-methyl-5-((3-(trifluoromethyl) phenyl)carbamoyl) phenyl)pyrrolidin-1-yl)picolinamide;

(R)—N-methyl-5-(3-(2-methyl-5-((3-(trifluoromethyl) phenyl)carbamoyl) phenyl)pyrrolidin-1-yl)nicotinamide;

(S)-3-(1-(5-(2-methoxyethoxy)pyridin-3-yl)pyrrolidin-3-yl)-4-methyl-N-(3-(trifluoromethyl)phenyl)benzamide;

(S)-3-(1-(5-(4,4-difluoropiperidin-1-yl)pyridin-3-yl)pyrrolidin-3-yl)-4-methyl-N-(3-(trifluoromethyl)phenyl) benzamide;

(S)-3-(1-(5-(4,4-difluoropiperidine-1-carbonyl)pyridin-3-yl)pyrrolidin-3-yl)-4-methyl-N-(3-(trifluoromethyl) phenyl)benzamide;

(S)-4-methyl-3-(1-(5-(morpholine-4-carbonyl)pyridin-3-yl)pyrrolidin-3-yl)-N-(3-(trifluoromethyl)phenyl)benzamide;

(S)—N-(2-(dimethylamino) ethyl)-5-(3-(2-methyl-5-((3-(trifluoromethyl) phenyl)carbamoyl)phenyl)pyrrolidin-1-yl)nicotinamide;

(S)—N-(2-methoxyethyl)-5-(3-(2-methyl-5-((3-(trifluoromethyl) phenyl)carbamoyl)phenyl)pyrrolidin-1-yl) nicotinamide;

3-((S)-1-(5-((R)-3-methoxypiperidin-1-yl)pyridin-3-yl) pyrrolidin-3-yl)-4-methyl-N-(3-(trifluoromethyl)phenyl)benzamide;

(S)-3-(1-(5-(2-oxa-6-azaspiro[3.3]heptan-6-yl)pyridin-3-yl)pyrrolidin-3-yl)-4-methyl-N-(3-(trifluoromethyl) phenyl)benzamide;

(S)-3-(1-(5-(difluoromethyl)pyridin-3-yl)pyrrolidin-3-yl)-4-methyl-N-(3-(trifluoromethyl)phenyl)benzamide;

(S)-3-(1-(5-(2-oxa-6-azaspiro[3.4]octan-6-yl)pyridin-3-yl)pyrrolidin-3-yl)-4-methyl-N-(3-(trifluoromethyl) phenyl)benzamide;

(S)-3-(1-(5-acetamidopyridin-3-yl)pyrrolidin-3-yl)-4-methyl-N-(3-(trifluoromethyl)phenyl)benzamide;

(S)-3-(1-(2-acetamidopyridin-4-yl)pyrrolidin-3-yl)-4-methyl-N-(3-(trifluoromethyl)phenyl)benzamide;

(S)-3-(1-(1H-pyrrolo[2,3-b]pyridin-4-yl)pyrrolidin-3-yl)-4-methyl-N-(3-(trifluoromethyl)phenyl)benzamide;

(S)-4-methyl-3-(1-(pyrazolo[1,5-a]pyrimidin-6-yl)pyrrolidin-3-yl)-N-(3-(trifluoromethyl)phenyl)benzamide;

(S)-4-methyl-3-(1-(6-((1-methyl-1H-pyrazol-4-yl) amino)pyridin-3-yl)pyrrolidin-3-yl)-N-(3-(trifluoromethyl)phenyl)benzamide;

(S)-4-methyl-3-(1-(5-((1-methyl-1H-pyrazol-4-yl) amino)pyridin-3-yl)pyrrolidin-3-yl)-N-(3-(trifluoromethyl)phenyl)benzamide;

(S)-3-(1-(5-((1-(2-methoxyethyl)-1H-pyrazol-4-yl) amino)pyridin-3-yl)pyrrolidin-3-yl)-4-methyl-N-(3-(trifluoromethyl)phenyl)benzamide;

(S)-3-(1-(6-((1-(2-methoxyethyl)-1H-pyrazol-4-yl) amino)pyridin-3-yl)pyrrolidin-3-yl)-4-methyl-N-(3-(trifluoromethyl)phenyl)benzamide;

(S)-4-methyl-3-(1-(2-((1-methyl-1H-pyrazol-4-yl) amino) pyrimidin-5-yl)pyrrolidin-3-yl)-N-(3-(trifluoromethyl)phenyl)benzamide;

(S)-4-methyl-3-(1-(2-(methylamino) pyrimidin-5-yl)pyrrolidin-3-yl)-N-(3-(trifluoromethyl)phenyl)benzamide;

(S)-3-(1-(6-aminopyridin-3-yl)pyrrolidin-3-yl)-4-methyl-N-(3-(trifluoromethyl)phenyl)benzamide;

(S)-3-(1-(2-acetamidopyrimidin-5-yl)pyrrolidin-3-yl)-4-methyl-N-(3-(trifluoromethyl)phenyl)benzamide;

(S)-4-methyl-3-(1-(5-(1-methyl-1H-pyrazol-4-yl)pyridin-3-yl)pyrrolidin-3-yl)-N-(3-(trifluoromethyl)phenyl) benzamide;

4-(3-(2-methyl-5-((3-(trifluoromethyl)phenyl)carbamoyl) phenyl)pyrrolidin-1-yl)picolinamide;

(S)-5-(3-(2-methyl-5-((4-(morpholinomethyl)-3-(trifluoromethyl)phenyl) carbamoyl)phenyl)pyrrolidin-1-yl) nicotinamide;

(S)-5-(3-(2-methyl-5-((3-(pyrrolidin-1-ylmethyl)-5-(trifluoromethyl)phenyl) carbamoyl)phenyl)pyrrolidin-1-yl)nicotinamide; and (S)-5-(3-(5-((4-((dimethylamino)methyl)-3-(trifluoromethyl)phenyl)carbamoyl)-2-methylphenyl)pyrrolidin-1-yl)nicotinamide.

9. A pharmaceutical composition comprising the compound of formula (I) or pharmaceutically acceptable salt thereof according to claim 1, in admixture with one or more pharmaceutically acceptable carriers or excipients.

10. The pharmaceutical composition according to claim 9, which is suitable for administration by inhalation.

11. A method of treating a disease, disorder or condition associated with dysregulation of DDR, comprising administering the pharmaceutical composition according to claim 9 to a subject in need thereof.

12. The method of claim 11, wherein the disease, disorder or condition associated with dysregulation of DDR is a fibrosis and/or a disease, disorder or condition that involves fibrosis.

13. The method of claim 12, wherein the fibrosis is at least one selected from the group consisting of pulmonary fibrosis, idiopathic pulmonary fibrosis (IPF), hepatic fibrosis, renal fibrosis, ocular fibrosis, cardiac fibrosis, arterial fibrosis and systemic sclerosis.

14. The method of claim 13, wherein the fibrosis is idiopathic pulmonary fibrosis (IPF).

15. A compound selected from the group consisting of the compound of formula (VI)

(VI)

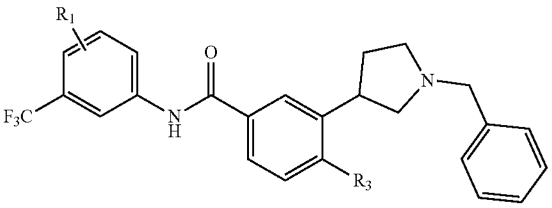

and the compound of formula (VII)

(VII)

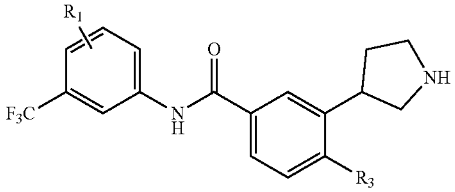

wherein $R_1$ is —$(C_1-C_6)$alkylene-$NR_AR_B$ or hydrogen;

$R_3$ is —$(C_1-C_4)$alkyl;

$R_A$, and $R_B$ are independently —$(C_1-C_6)$alkyl or hydrogen;

or $R_A$ and $R_B$ taken together with the nitrogen they are attached to may form a heterocycloalkyl.

16. A process for the preparation of the compound of formula (I), or pharmaceutically acceptable salt thereof, according to claim 1, comprising:

a) reacting a compound of formula (V)

(V)

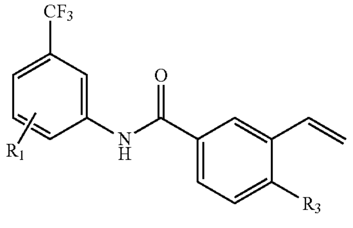

with N-benzyl-1-methoxy-N-((trimethylsilyl)methyl) methanamine

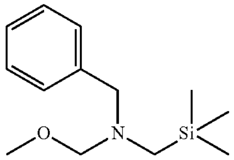 [SMILES: COCN(Cc1ccccc1)C[Si](C)(C)C]

under acid catalysis in the presence of a solvent to obtain a compound of formula (VI)

(VI)

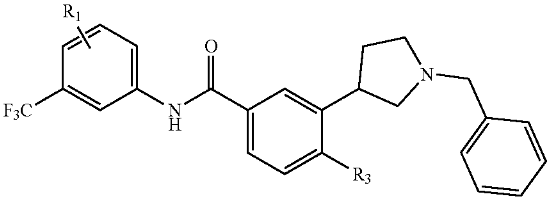

wherein R1 and R3 are as defined in claim 1, and converting the compound of formula (VI) into the compound of formula (I).

17. The process according to claim 16, further comprising the steps of:

b) cleaving the benzyl group of the compound of formula (VI) such as to obtain a compound of formula (VII):

(VII)

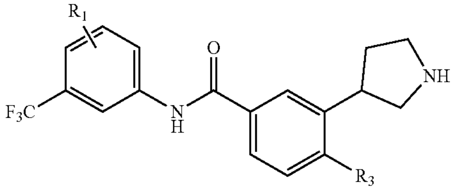

by reduction under hydrogen atmosphere in the presence of a Pd catalyst; and c) reacting the compound of formula (VII) with a carboxylic acid compound of formula (VIII) or a fluoride compound of formula (IX) or a bromide compound of formula (X)

(VIII)

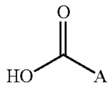

-continued (IX)

(X)

wherein A is selected from the group consisting of A1, A2, A3

A1

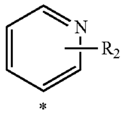

A2

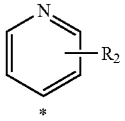

A3

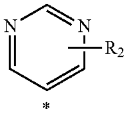

and bicyclic heteroaryl B, wherein * indicates the point of attachment to the COOH in formula (VIII) or the F in formula (IX) or the Br in formula (X); and B is substituted by $R_2$; wherein $R_2$ is H or selected from the group consisting of halogen, cyano, —$NR_AR_B$, —C(O)$NR_AR_B$, —C(O)$NR_C$—($C_1$-$C_6$)alkylene-$NR_AR_B$, —C(O)$NR_C$—($C_1$-$C_6$)alkylene-$OR_A$, —$NR_A$C(O)$R_B$, —$OR_A$, —$NR_C$—($C_1$-$C_6$)alkylene-$OR_A$, —$NR_C$—($C_1$-$C_6$)alkylene-$NR_AR_B$, —C(O)$NR_A$-heterocycloalkyl, heterocycloalkyl, —$NR_A$-heteroaryl, —($C_1$-$C_6$)alkylene-heterocycloalkyl, —($C_1$-$C_6$)alkylene-$OR_A$, —O—($C_1$-$C_6$)alkylene-$NR_AR_B$, —O—($C_1$-$C_6$)alkylene-$OR_A$, —O—($C_1$-$C_6$)alkylene-heterocycloalkyl, —($C_1$-$C_6$) haloalkyl and —($C_1$-$C_6$)alkyl;

$R_A$, $R_B$ and $R_C$ are independently —($C_1$-$C_6$)alkyl or hydrogen;

or $R_A$ and $R_B$ taken together with the nitrogen they are attached to may form a heterocycloalkyl;

and wherein each heterocycloalkyl or heteroaryl of $R_2$ is substituted by one or more substituents independently selected from the group consisting of hydrogen, halogen, —($C_1$-$C_6$)alkyl, —($C_1$-$C_6$) haloalkyl, —($C_1$-$C_6$)alkylene-$OR_A$, —$OR_A$, —O—($C_1$-$C_6$)alkylene-$NR_AR_B$ and —O—($C_1$-$C_6$)alkylene-$OR_A$;

to obtain the compound of formula (I).

* * * * *